US011881287B2

(12) United States Patent
Gardner et al.

(10) Patent No.: US 11,881,287 B2
(45) Date of Patent: Jan. 23, 2024

(54) CONTROL APPARATUS AND METHOD FOR PROCESSING DATA INPUTS IN COMPUTING DEVICES THEREFORE

(71) Applicant: PRECISIONLIFE LTD, Oxon (GB)

(72) Inventors: Stephen Philip Gardner, Kidlington (GB); Gert Lykke Sørensen Moller, Horsholm (DK)

(73) Assignee: PRECISIONLIFE LTD, Oxon (GB)

( * ) Notice: Subject to any disclaimer, the term of this patent is extended or adjusted under 35 U.S.C. 154(b) by 324 days.

(21) Appl. No.: 17/161,870

(22) Filed: Jan. 29, 2021

(65) Prior Publication Data

US 2021/0210170 A1 Jul. 8, 2021

Related U.S. Application Data

(63) Continuation-in-part of application No. 16/348,995, filed as application No. PCT/EP2017/025333 on Nov. 10, 2017, now Pat. No. 10,948,887.

(Continued)

(30) Foreign Application Priority Data

Nov. 10, 2016 (GB) .................................... 1619039
May 11, 2017 (GB) .................................... 1707588

(51) Int. Cl.
*G16B 40/20* (2019.01)
*G16H 10/40* (2018.01)
(Continued)

(52) U.S. Cl.
CPC .............. *G16B 40/20* (2019.02); *G06N 5/01* (2023.01); *G06N 5/022* (2013.01); *G16B 30/00* (2019.02);
(Continued)

(58) Field of Classification Search
CPC ........ G16B 40/20; G16B 30/00; G16B 20/20; G06N 5/01; G06N 5/022; G06N 20/00;
(Continued)

(56) References Cited

U.S. PATENT DOCUMENTS 6,633,863 B1 * 10/2003 Sørensen Møller .... G06F 30/00
10,565,329 B2 2/2020 Greenwood
2017/0147722 A1 5/2017 Greenwood

FOREIGN PATENT DOCUMENTS

WO 2014142777 A2 9/2014
WO 2015148599 A1 10/2015

OTHER PUBLICATIONS

International Search Report and Written Opinion of the International Searching Authority, Application No. PCT/EP2017/025333, dated Mar. 14, 2018, 9 pages.
(Continued)

*Primary Examiner* — Charles R Kasenge
(74) *Attorney, Agent, or Firm* — ZIEGLER IP LAW GROUP, LLC

(57) ABSTRACT

There is provided a method for using a control apparatus to process one or more data inputs in a computing arrangement to provide one or more outputs comprising at least one of control outputs, analysis outputs, or recommendation outputs. The control apparatus is configured to execute real-time computing for a multi-dimensional system model spanned by state variables on one or more of finite domains or intervals. The one or more data inputs include one or more physical measurands of a system, and the one or more outputs provide a technical modification of the system. The method includes:
providing a system model in which all valid combinations and associated properties or object functions are stored as interconnected relations distributed on one or more computers; and
(Continued)

deducing one or more of:
(i) any sub-space, corresponding to an input statement of states or combinations spanned by one or more state variable or associated properties or object functions, by deriving consequences of the input statement by applying constraints defined by the input statement to the system model; or
(ii) any sub-space, corresponding to a query, of states or combinations spanned by one or more state variables or associated properties or object functions, by deriving consequences of the query by applying constraints defined by the query to the system model.

14 Claims, 55 Drawing Sheets

Related U.S. Application Data

(60) Provisional application No. 62/504,655, filed on May 11, 2017, provisional application No. 62/420,491, filed on Nov. 10, 2016.

(51) Int. Cl.
*G16H 20/00* (2018.01)
*G06N 5/00* (2023.01)
*G06N 5/02* (2023.01)
*G16B 30/00* (2019.01)
*G16H 50/30* (2018.01)
*G06N 5/022* (2023.01)
*G06N 5/01* (2023.01)

(52) U.S. Cl.
CPC ............. *G16H 10/40* (2018.01); *G16H 20/00* (2018.01); *G16H 50/30* (2018.01)

(58) Field of Classification Search
CPC ........ G06N 5/045; G16H 10/40; G16H 20/00; G16H 50/30; G16H 20/10; G16H 50/70; G16H 70/40; Y02A 90/10; G06F 17/11
See application file for complete search history.

(56) References Cited

OTHER PUBLICATIONS

International Preliminary Report on Patentability and Written Opinion of the International Searching Authority , Application No. PCT/EP2017/025333, dated Feb. 25, 2019, 6 pages.
United States Patent and Trademark Office, Non-Final Office Action, U.S. Appl. No. 16/348,995, dated Jun. 18, 2020, 10 pages.

* cited by examiner

| A | B | Link0 |
|---|---|---|
| 0 | 0 | 0 |
| 0 1 | 0 1 | 1 |
| 0 1 | 0 | 2 |
| 0 | 1 | 3 |

| C | D | Link0 | Link1 |
|---|---|---|---|
| 0 | 0 | 0 | 0 |
| 0 | 1 | 1 | 1 |
| 1 | 0 1 | 2 3 | 2 |

| E | F | Link1 |
|---|---|---|
| 0 | 1 | 0 |
| 1 | 0 | 0 1 2 |

2700

Taking Isocarboxazid with food and drink

You should NOT take alcohol (especially red wine) whilst you are taking Isocarboxazid tablets. This includes non-alcoholic beer or lager.

Isocarboxazid tablets stop the breakdown of a substance called tyramine which is found in large amounts of certain foods. If this substance is not broken down, it can cause very high blood pressure. So, while you are taking Isocarboxazid and for two weeks after the course of treatment has finished, you should avoid the following foods:

- Matured cheeses (e.g. cheddar or processed cheese made from mature cheese)

- Yeast extracts (e.g. Bovril or Marmite)

- Meat, fish or poultry which is not fresh or has been pickled

- Broad bean pods

- Over-ripe fruit

| Cluster states | | | | | V1 | V2 |
|---|---|---|---|---|---|---|
| EV967 0 | EV355 2 | EV60 5 | EV1764 1 | | 4 | 0 |
| EV355 2 | EV60 5 | EV1764 1 | EV863 2 | | 4 | 0 |
| EV967 0 | EV1764 1 | EV174 3 | | | 4 | 1 |
| EV1764 4 | EV174 1 | EV466 0 | EV1710 0 | EV1120 0 | 4 | 1 |

FIG. 29

| Event | Current state | New state | Actions |
|---|---|---|---|
| "PLAY" | CS1 | NS1 | Display XXX |
| "PLAY" | CS2 | NS2 | Display YYY |

Event → | Current state (pre-state) → | New state (post-state) →

| Event | Current state (pre-state) | New state (post-state) |
|---|---|---|
| PLAY | A2 C3 E7 G0 I6 | C1 F2 |
| PLAY | C3 D1 F5 G0 H8 J9 | D4 G5 H6 |
| PLAY | A1 E7 J8 | C5 J9 |
| PLAY | D4 E1 G6 J2 | D2 |

FIG. 32B

R0: (A and B) -> (C or D or E)
R1: (C or D or E) -> (F and G)

3400B

R0

| A | B | C | D | E |
|---|---|---|---|---|
| 0 1 | 0 | 0 | 0 | 0 |
| 0 1 | 0 1 | 0 1 | 0 1 | 1 |
| 0 1 | 0 1 | 0 1 | 1 | 0 |
| 0 1 | 0 1 | 1 | 0 | 0 |
| 0 | 1 | 0 | 0 | 0 |

R1

| C | D | E | F | G |
|---|---|---|---|---|
| 0 | 0 | 0 | 0 1 | 0 |
| 0 | 0 | 0 | 0 | 1 |
| 0 1 | 0 1 | 0 1 | 1 | 1 | join R0 R1

| A | B | C | D | E | F | G |
|---|---|---|---|---|---|---|
| 0 1 | 0 | 0 | 0 | 0 | 0 1 | 0 |
| 0 1 | 0 | 0 | 0 | 0 | 0 | 1 |
| 0 1 | 0 | 0 | 0 | 0 | 1 | 1 |
| 0 1 | 0 1 | 0 1 | 0 1 | 1 | 1 | 1 |
| 0 1 | 0 1 | 0 1 | 1 | 0 | 1 | 1 |
| 0 1 | 0 1 | 1 | 0 | 0 | 1 | 1 |
| 0 | 1 | 0 | 0 | 0 | 0 1 | 0 |
| 0 | 1 | 0 | 0 | 0 | 0 | 1 |
| 0 | 1 | 0 | 0 | 0 | 1 | 1 |

FIG. 34B

Step 1: Colligate one common variable at a time

Example: common variable C

```
    AP     (attributes of variable C)
   ┌─────────────┬───────┐
   │0 0 1 0 1 1 0│0 0 0 1│
   └─────────────┴───────┘

DAP    (unique attributes of variable C)
   ┌───────┬─────┐
   │0 0 1 1│0 0 1│
   └───────┴─────┘

GI←DAP⍳AP    (indices of AP in DAP)
   ┌───────────┬─────┐
   │0 1 1 2 0  │0 0 1│
   └───────────┴─────┘

JO←∘.∩/DAP   (intersection of DAP)
   ┌─────┐
   │ 0│ 0│
   ├─────┤
   │ 0│0 1│
   ├─────┤
   │     │ 1│
   └─────┘

BM0    (non-empty intersection of JO)
1 1
1 1
0 1

BM     (matching combinations of arguments in R0,R1)
1 1 1
1 1 1
1 1 1
0 0 1
1 1 1
```

FIG. 34C

| | Unbound SV | | Prestate SV | | Poststate SV D=2 |
|---|---|---|---|---|---|
| A | 0123456789 | A | 6 | A | 01234789 |
| B | 0123456789 | B | 2 | B | 0123456789 |
| C | 0123456789 | C | 2 | C | 0123456789 |
| D | 0123456789 | D | 4 | D | 2 |
| E | 0123456789 | E | 1 | E | 0123456789 |
| F | 0123456789 | F | 8 | F | 0123456789 |
| G | 0123456789 | G | 6 | G | 0123456789 |
| H | 0123456789 | H | 5 | H | 0123456789 |
| I | 0123456789 | I | 4 | I | 0123456789 |
| J | 0123456789 | J | 3 | J | 0123456789 |

| | | | | |
|---|---|---|---|---|
| A | 4 | | A | 4 |
| B | 01234567 | | B | 2 |
| C | 3 | | C | 3 |
| D | 2 | | D | 2 |
| E | 0123456789 | | E | 3456789 |
| F | 0123456789 | <> | F | 12345679 |
| G | 03456789 | | G | 03456789 |
| H | 0123456789 | | H | 0123456789 |
| I | 37 | | I | 37 |
| J | 0123456789 | | J | 0123456789 |

| SV1 | | SV2 |
|---|---|---|
| A | 4 | A | 4 |
| B | 2 | B | 2 |
| C | 3 | C | 3 |
| D | 2 | D | 2 |
| E | 9 | E | 9 |
| F | 12345679 | F | 12345679 |
| G | 03456789 | H | 03456789 |
| H | 0123456789 | H | 0123456789 |
| I | 37 | I | 37 |
| J | 8123456789 | J | 0123456789 |

| | | | | |
|---|---|---|---|---|
| A | 4 | | A | 4 |
| B | 2 | | B | 2 |
| C | 3 | | C | 3 |
| D | 2 | | D | 2 |
| E | 9 | | E | 9 |
| F | 7 | => | F | 7 |
| G | 03456789 | | G | 6 |
| H | 0123456789 | | H | 5 |
| I | 37 | | I | 37 |
| J | 0123456789 | | J | 0123456789 |

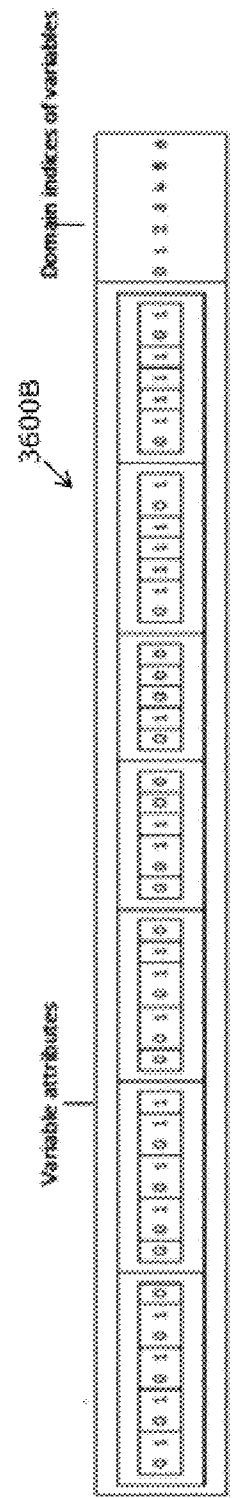
A) Matrix representation of relation
FIG. 36A
B) Internal binary representation using nested attributes
FIG. 36B
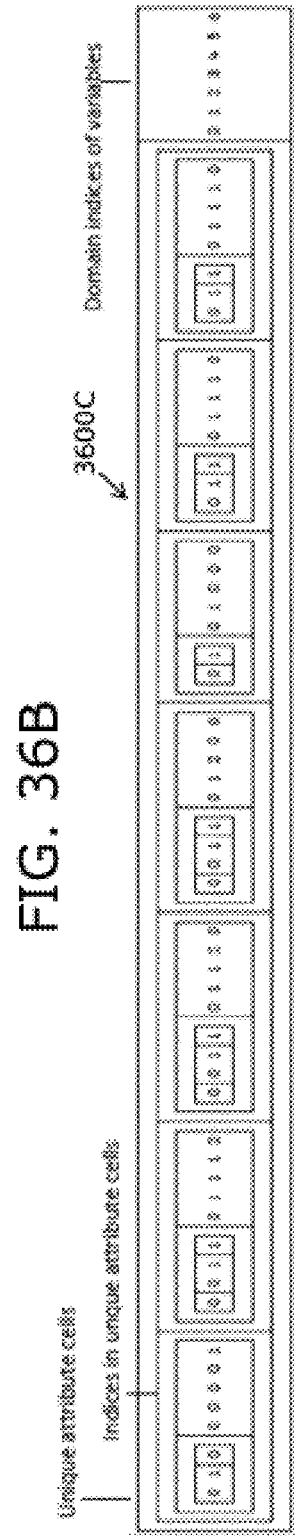
C) Internal binary representation using indexed attributes
FIG. 36C

| COLLECT ONE OR MORE PATHOGENS PRESENT IN FARMING ENVIRONMENT 4102 | GENOTYPE SEQUENCES THE ONE OR MORE PATHOGENS TO CHARACTERIZE THE ONE OR MORE PATHOGENS 4104 | EMPLOY CHARACTERIZATION OF THE ONE OR MORE PATHOGENS AS INPUT PARAMETER TO SOFTWARE PRODUCT 4106 |

MARKERS output (single validated n-state associated with high yield):

| 23722 | 1 | 31919 | 1 | 32295 | 1 | 64217 | 2 | 67173 | 0 | 74648 | 1 | 92817 | 0 | 98558 | 1 |

PACE relation (all possible n-states and associated yield):

| SNP#23722 | SNP#31819 | SNP#32295 | SNP#64217 | SNP#67173 | SNP#74648 | SNP#92817 | SNP#98558 | Yield |
|---|---|---|---|---|---|---|---|---|
| 1 | 1 | 0 | 1 | 0 | 0 | 1 | 1 | 1233 |
| 1 | 2 | 2 | 2 | 0 | 1 | 0 | 1 | 1025 |
| 1 | 1 | 1 | 2 | 0 | 1 | 0 | 0 | 959.1 |
| 1 | 1 | 1 | 2 | 0 | 1 | 0 | 1 | 914.6 |
| 1 | 1 | 1 | 2 | 0 | 1 | 0 | 1 | 911.1 |
| 1 | 0 | 1 | 2 | 0 | 0 | 0 | 1 | 888.1 |
| 1 | 0 | 1 | 2 | 0 | 0 | 0 | 0 | 860.1 |
| 1 | 1 | 1 | 2 | 0 | 1 | 0 | 1 | 860.1 |
| 1 | 1 | 1 | 2 | 0 | 1 | . | 1 | 853.1 |

FIG. 46

MARKERS output (single validated n-state):

| 261 | 1 | 434 | 2 | 438 | 0 |

PACE relation (all possible n-states with outcome derived from case-control phenotype):

| SNP#261 | SNP#434 | SNP#438 | sumCases | sumControls | OR |
|---|---|---|---|---|---|
| 1 | 2 | 0 | 16 | 1 | 35.72 |
| 2 | 2 | 0 | 1 | 0 | 22.32 |
| 2 | 1 | 2 | 5 | 4 | 2.79 |
| 0 | 2 | 2 | 7 | 10 | 1.563 |
| 2 | 1 | 0 | 9 | 15 | 1.339 |
| 1 | 0 | 0 | 51 | 91 | 1.251 |
| 2 | 1 | 1 | 12 | 23 | 1.165 |
| 0 | 2 | 0 | 10 | 20 | 1.116 |
| 0 | 0 | 1 | 98 | 197 | 1.11 |

FIG. 47

CONTROL APPARATUS AND METHOD FOR PROCESSING DATA INPUTS IN COMPUTING DEVICES THEREFORE

TECHNICAL FIELD

The present disclosure relates to control apparatus for processing input data in computing devices to generate corresponding control outputs; for example, the present disclosure relates to control apparatus for processing input data, for example derived from sensors, for performing real-time signal processing, for resolving constraints and for optimizing systems. Moreover, the present disclosure concerns methods for (namely, methods of) processing input data in the aforementioned control apparatus. Furthermore, the present disclosure relates to computer program products including computer-readable instructions, for example the computer readable instructions being stored on a non-transitory computer-readable storage medium, the computer-readable instructions being executable by a computerized device comprising processing hardware to execute aforementioned methods. The aforementioned control apparatus and methods are configured to provide real-time context-sensitive reasoning and decision support on, for example, mobile and wearable computing devices, when provided with multi-dimensional input data, for example real physical measurands. Moreover, the apparatus and methods are susceptible to being used in automotive and electronic control, in digital health care environments, in the Internet of Things ("IoT"), in mobile health provision ("mHealth") and for supporting implementations of precision medicine; however, the apparatus and methods are also susceptible to being used in many other use applications. The present disclosure also relates to welfare systems, namely to welfare systems that provide, when in operation, customized welfare support to individuals in assistive environments to enhance their comfort and physical condition; the welfare systems provide, for example, improved nutritional, therapeutic and targeted treatments for the individuals, for example by developing medicines for the individuals, and by repurposing medicines for the individuals. Moreover, the welfare systems provide for selective breeding through DNA analysis of blastocysts and embryos, to select embryos with preferred predicted phenotype characteristics, wherein selected embryos are implanted via IVF to provide individuals with enhanced properties, for example for providing more efficient conversion of nutrition provided (for example, *Bos Taurus* is much more food efficient and produces more milk in comparison to other breeds, but is less resistant to heat or drought than *Bos Indicus*). Moreover, the present disclosure also relates to methods of (namely methods for) operating aforesaid welfare systems. The present disclosure also relates to systems and methods for pharmaceutical drug discovery to provide various forms of targeted medical products; these systems and methods can therefore be regarded as a part of pharmaceutical drug manufacturing systems and methods.

BACKGROUND

Control apparatus are known for processing input data representative of real physical variables acquired by sensor arrangements and providing corresponding control outputs; such control apparatus beneficially uses, when in operation, computer-based decision support systems for generating consistent, context-sensitive recommendations in real-time and with a predictable low memory footprint on a wide range of computing platforms. Such control apparatus often use sensors and signal processing hardware, embedded control systems, wearable and mobile devices, graphical processing units (GPUs) and supercomputers. The control apparatus are operable to evaluate all consequences of highly-specific combinations of multi- or even hyper-dimensional input data to predict behaviors of complex environments, and are potentially enormously beneficial in a wide variety of technical fields of use. Such technical fields include, for example, exceptionally complex apparatus employed in healthcare environments, healthcare systems, railway interlocking systems, Internet of Things (IoT), smart-grids, robotics, autonomous vehicles, safety systems in nuclear powerplants, and consumer electronics.

Conventionally, complex decisions are routinely made at points of care in a given healthcare system; for example, complex decisions are often made when a clinician interacts with a patient and provides corresponding diagnoses, prescriptions and advice. The decisions are complex to make, because the patient is potentially within a huge range of genetic, phenotypic, clinical and environmental diversity. For example, each patient is unique and will react differently to a given treatment regimen at a given stage of their lives. Current best clinical practice follows generic clinical pathways, for example there is employed a hypothesis " . . . if you have this disease, then prescribe this set of drugs . . . ". However, such decisions are often made outside a range of specific companion diagnostic tests, and often takes minimal account of the given patient's personal factors. Similar considerations pertain when controlling other types of complex facilities or systems, for example in a case of a nuclear facility (such as at Fukushima Dai'ichi, Japan): "When a reactor core meltdown occurs at a nuclear plant, evacuate a 100 km zone around the nuclear plant, evacuating any large city nearby and start pumping in large quantities of water, ensuring that hydrogen gas is vented to avoid a hydrogen explosion within a burn hole generated by the reactor core meltdown". Similar considerations also pertain to configuring an optimal arrangement of chemical processes for treating nuclear waste to render it suitable for long-term deep geological repository storage for 500000 years.

In developed industrial societies having a high public welfare standard, there are presently employed in a range of 10% to 20% of gross domestic product (GDP) for healthcare related activities. Such a relatively high range results in parts from inefficient delivery of healthcare services; for example, clinicians often find it contemporarily hard to personalize care to find a best combination of therapies for a given patient that the clinicians are seeking to treat. Such inefficiency results in patients being prescribed medicines that will not work for them; for example, on average, cancer drugs are effective in only 35% of patients in practice. Prescribed medicines are often ineffective because it is difficult for a given patient to adhere to a prescribed therapeutic regimen set by the given patient's doctor, for example as a result of the therapeutic regimen not providing benefits expected by the given patient. For example, interactions between drugs cause side-effects that make patients feel more unwell; these interactions often arise from issues that were not envisaged by the given patient's doctor. Contemporarily, chronic diseases (such as cancer, cardiovascular disease, dementia and diabetes) exert huge social and financial burdens worldwide. In the United Kingdom (UK), chronic diseases are responsible for 85% of all human deaths, and the 30% of the UK population that has one or more chronic conditions consumes over 70% of the National Health Service (NHS) budget allocated for the UK. Much of this cost (for example, up to £8 billion (GBP) of a £10 billion (GBP) diabetes bill in the UK) is caused:
  (i) by patients who are unable to manage effectively their one or more diseases;
  (ii) by patients developing further complications arising from these diseases; and
  (iii) from avoidable hospitalizations due to inaccurate or unsafe prescriptions and/or adverse drug reactions.

Adverse drug reactions become common as a given patient takes more drugs (medicines). However, it will be appreciated that chronic diseases require long-term polypharmaceutical treatment regimens, wherein patients afflicted by such chronic diseases are often required to take in a range of 4 to 10 (or even more) prescription drugs on a daily basis; moreover, such chronic patients with these conditions have very high incidences of side effects and consequently exhibit a highest incidence of patient non-adherence (namely, failing to take prescribed medications). Patient non-adherence is, for example, routinely observed in a range of 40% to 50% in cases of diseases such as chronic obstructive pulmonary disease (COPD).

Aforementioned side effects are exacerbated in a situation where clinicians treat patients for one disease at a time, rather than taking a holistic approach. Such an exacerbation occurs, for example, when a given patient is referred to a plurality of specialist clinicians who prescribe new therapies for one given disease of a plurality of diseases afflicting the given patient, without due consideration of a combinatorial effect of those medications on the given patient's metabolism. Thus, it is beneficial for clinical teams to evaluate the combinatorial impact of the given patient's whole polypharmaceutical therapeutic regimen on the given patient's diseases; as a result, it is feasible, when taking into consideration the combinatorial impact, to implement more compatible selections of therapies. However, contemporarily, there are no effective tools for being able to implement more compatible selections in a systematic personalized basis across a whole patient population at a given point of care.

Contemporarily, it is a major strategic priority to provide precision or personalized medicine for healthcare systems, because such precision or personalized medicine is widely understood to offer more accurate and cost-effective ways of understanding earlier a given patient's individual disease risks, thereby enabling a delay in an onset of disease to be achieved, and also enabling a more accurate prescription of a best available treatment option to be made, thereby improving health of the given patient. Implementing precision medicine, for example by employing control apparatus to control a supply of medicine to a given patient, has contemporarily been found to be extremely difficult to achieve in practice, especially when considering a given patient's whole health burden and not just a single diagnosis pertaining to the given patient. In order to provide contextualized predictions that take into account all factors applying to a given healthcare system, it is necessary to take into consideration disease processes, genetic predispositions to disease risk and therapy responses, clinical assay results, drug pharmacology and systems biology.

Thus, in order to provide contextualized predictions, there arises a need for massively complex analyses to predict accurately individual risks and therapy responses for real example patients. When contemporarily seeking to provide truly personalizing diagnostic interpretations and prescription decisions for a specific patient, there is required an understanding of a disease for which the specific patient has been diagnosed, or a treatment for the disease, together with an understanding of the specific patient's genotypic, phenotypic, clinical history, co-morbidities, co-prescriptions, lifestyle, environmental, and potentially other factors, all of which will have an impact on the specific patient and the specific patient's response to therapeutic regimens. However, such conceptualized predictions are often beyond an intellectual capacity of many experienced doctors and surgeons. Known control apparatus for assisting aforesaid doctors and surgeons with decision support have been found to be too computationally demanding and/or to deliver control results insufficiently accurately or promptly.

From the foregoing, it will be appreciated that it is desirable to employ software programs, for example software applications, such as computer-based expert systems that can systematically personalize healthcare recommendations, such as improving an accuracy and safety of prescriptions that are prescribed for implementing complex therapeutic regimens, for providing accurate and safe advice to a given patient on their most beneficial diet and lifestyle, and for identifying a best clinical practice to employ (for example, in terms of costs, risks and outcomes); delivering such personalized healthcare recommendations in a more effective manner is paramount to achieving a cost-effective delivery of effective healthcare. Currently, however, there are no truly effective analytical solutions to such problems, due to a hyper-dimensionality and combinatorial complexity of analyses required when seeking to provide a more cost-effective delivery of effective healthcare; for such analyses to be generally useful, they need to be available in real-time to a given clinician at a point of care (for example, to aid in selecting a best available drug for a specific patient), or to a given patient in a course of his/her daily lives (for example, to provide actionable advice to help the given patient to modify his/her diet and lifestyle to optimize his/her health and chances of a successful outcome of administered treatment to the given patient).

Contemporarily, statistical and machine learning methods are occasionally used to attempt to identify correlations pertaining to interaction effects arising between a plurality of treatments when administered concurrently. However, it is found in practice that these methods include training bias and do not scale reliably when applied to multi- or hyper-dimensional data, nor do the methods cope well with integrating multiple types of input data into analyses employed in the methods. Moreover, the methods cannot, in some cases, accommodate missing or partially erroneous data (i.e. "dirty data"), and particularly cannot scale computationally to cope with a vast increase in a combinatorial problem space that is presented to the aforesaid methods when there are multiple variables, wherein each variable can have associated therewith a large range of potential values.

Contemporary analytical methods seek to cope with the aforementioned vast increase in the combinatorial problem space either by seeking to simplify the problem space to successive one-dimensional slices, or to classify or prune the combinatorial problem space to reduce its complexity.

The aforementioned methods of analyzing the combinatorial problem space are found in practice to be so computationally intensive that, without approximating the combinatorial problem space in ways as aforementioned, they cannot generate recommendations in real-time for individual patients, even when massively distributed server architectures such as Hadoop or IBM Watson are employed to execute computations for implementing the methods; "Hadoop" and "IBM Watson" are registered trademarks. Moreover, it will be appreciated that "Hadoop" and "IBM Watson" are respected as being leading-edge computing products and are highly respected within contemporary computing industries. Thus, the methods cannot be executed on relatively low-power mobile, wearable or embedded computing systems, and cannot therefore provide interactive answers to patients' questions and actionable advice outside a clinical setting, and particularly not on a wearable or mobile computing device that a given patient or carer is likely to carry around with them.

To provide detailed, useful and relevant advice to end-users, for example to clinicians and/or patients, there is therefore required that a combination of all diverse factors describing an individual patient, namely their "input state vector", can be analysed in real-time on a mobile computing device, for example a smartwatch, mobile telephone (USA: "cellphone") or tablet-like computing device, without a need for access external computing resources via a data communication network, for example the Internet or a remote server, and that a decision support system hosted on the mobile computing device to provide safe and consistent inferences in real-time, taking into account all input variables and constraints; for example, it is required that there are generated personalized recommendations for a given patient, wherein the personalized recommendations are of a quality and standard that is comparable to best clinical practice, taking into account all the given patient's multi-dimensional health factors as represented in a combinatorial problem space.

Contemporarily, many systems analysis tools have become available, for example as described in published patent applications WO90/09001 and U.S. Pat. No. 5,515, 524. However, there still exists an unmet demand for systems that are able to generate inferences in relation to larger and more complex problems, wherein the problems concern multiple variable types and there arise requirements for completeness and compactness and real-time deduction on a small computing device having relatively limited data memory. In this context, a term "completeness" indicates a mathematical requirement that all combinations in the aforementioned combinatorial problem space have been verified to ensure that a logical consistency is achieved when performing computations to find solutions in relation to the combinatorial problem space. When reacting to an emergency situation, for example to a blowout at a complex oil and gas production facility, accurate real-time deduction can be critical to saving lives of facility workers that are potentially affected by such a blowout.

Basic concepts of context-sensitive reasoning and decision support technology are described in published PCT patent applications WO 09948031A1 and WO 2001022278A1. A first generation of technology (herein referred to as "ADB 1.0") described in the aforementioned PCT patent applications has proven to be efficient for simple product configurations and similar kinds of problems, but the technology has not been found to scale satisfactorily to process very complex problems such as those described in the foregoing with reference to healthcare.

A scientific/mathematical discussion of principles of processing a complex combinatorial problem space is disclosed in a publication by Møller, Gert L: "*On the Technology of Array-based Logic*". Ph.D. thesis, Electric Power Engineering Department, Technical University of Denmark, January 1995.

It will be appreciated that intelligent control apparatus for industrial production facilities, agricultural facilities, building environmental control and so forth have been the subject matter of numerous granted EP and UK patents, over a period of many years, and is widely accepted as providing a technical effect (i.e. not excluded from patentability).

SUMMARY

The present disclosure seeks to provide an improved method for (namely, a method of) processing input data in computing devices, for example in control apparatus, to generate corresponding outputs; for example, the input data corresponds to real physical variables and processed results from the method are used for information and/or control purposes. Moreover, the present disclosure seeks to provide an improved control apparatus employing one or more methods for processing input data in computing devices; for example, the input data corresponds to real physical variables and processed results from the method are used for information and/or control purposes.

According to a first aspect, there is provided a method for using a control apparatus to process one or more data inputs in a computing arrangement to provide one or more outputs comprising at least one of control outputs, analysis outputs, or recommendation outputs, wherein the control apparatus is configured to execute real-time computing for a multi-dimensional system model spanned by state variables on one or more of finite domains or intervals, wherein the one or more data inputs include one or more physical measurands of a system, and the one or more outputs provide a technical modification of the system, the method comprising:

providing a system model in which all valid combinations and associated properties or object functions are stored as interconnected relations distributed on one or more computers; and deducing one or more of:

(i) any sub-space, corresponding to an input statement of states or combinations spanned by one or more state variable or associated properties or object functions, by deriving consequences of the input statement by applying constraints defined by the input statement to the system model; or (ii) any sub-space, corresponding to a query, of states or combinations spanned by one or more state variables or associated properties or object functions, by deriving consequences of the query by applying constraints defined by the query to the system model.

The method is of advantage in that the multi-dimensional system model can be implemented in devices of control apparatus having modest data processing performance and provide processed results more rapidly than known contemporary methods. By "technical modification" is meant a change in a physical configuration, a physical state or a physical parameter of a system.

Optionally, the method further comprises representing input state vectors (SV1) associated with one or more of asserted or measured states of each variable and each object function from an environment in the system model, and representing output state vectors (SV2) associated with one or more deduced consequences on each variable and each object function of the entire system model, when external constraints of the input state vectors (SV1) are colligated with the static constraints in the system model.

Optionally, the method includes clustering state vectors associated with known attributes.

Optionally, the method includes configuring the multidimensional system model to include static constraints, clusters or accumulated states, and dynamic rules which represent transitions between valid states.

Optionally, the method comprises operating the multi-dimensional system model to have a plurality of system model states, and to change state from a given preceding system model state in among the system model states to a subsequent system model state among the system model states, depending upon a computed solution to the given preceding system model state and operative input data applied to the multi-dimensional system model. More optionally, the method further comprises computing the state of the entire system model in real-time by consulting at least one of one or more sub-systems or relations at a time by deducing possible states of each variable and propagating one or more bound link variables to connected one or more relations until no further constraints can be added to the state vectors. Yet more optionally, the method comprises arranging for the sub-systems to be distributed on a plurality of computing devices and to interact by propagating a common core link variable on each subsystem.

The method is susceptible to being used (namely, employed), for example, in industrial control apparatus for controlling industrial production facilities, agricultural production facilities (for example, in greenhouses for tomato production; in farm machinery for responsive crop management; in hydroponics facilities for perishable fruit production; in animal husbandry, in selective breeding of animals or crops; to provide improved animal welfare), healthcare providing facilities, smart metering arrangements (for example, in smart energy meters, in smart water meters), autonomous vehicle driving arrangements (for example, autonomous and self-drive vehicles), in intelligent drones for surveillance use, in airborne radar systems, in intelligent apparatus for assisting medical surgery and/or treatment, in personal wearable devices and so forth. The method is susceptible to providing control outputs for controlling operation of aforesaid industrial production facilities and so forth, as well as receiving sensor signals from such aforesaid industrial production facilities and so forth. The method is capable of saving resources, for example reducing prescription of ineffective or inappropriate pharmaceutical drugs, reducing unnecessary medical interventions, reducing energy consumption, reducing the amount of chemical pesticides and fertilizers applied, reducing amounts of physical resources needed for given production in industry, reducing atmospheric carbon dioxide emissions (for example, "greenhouse gas emissions") and so forth. The method is also capable of providing improved patient treatment in cases of pandemics, for example SARS-related pandemics such as contemporary COVID-19 pandemic.

Optionally, in the method, data processing that is implemented includes at least one of: embedded constraint resolution, decision support, system control, machine learning. Optionally, in the method, the computing arrangement includes at least one of: a computing device, a distributed arrangement including a plurality of computing devices.

Optionally, the method includes representing an addressable solution space in respect of all external state variables by a plurality of relations sharing only internal link variables. More optionally, the method includes arranging for any given pair of relations to share no more than one link variable. More optionally, in the method, any given index of any link variable represents a unique single valid state or combination of a unique subset of the external state variables and associated properties or object functions. Optionally, the method includes minimizing the solution space for memory storage by splitting relations into a plurality of corresponding relations shared by link variables with a minimal possible number of indices.

Optionally, the method includes splitting and reducing, for example minimizing, relations sharing groups of external state variables and then executing colligation of each group of variables.

Optionally, the method includes splitting the system model into a plurality of sub-models by splitting a core relation into a plurality of corresponding relations sharing only a core variable with indices of Cartesian arguments of the core relation. More optionally, in the method, the sub-models are distributed over a plurality of computing devices that are mutually coupled together in operation via a data communication network.

According to a second aspect, there is provided a computer program product comprising a non-transitory computer-readable storage medium having computer-readable instructions stored thereon, the computer-readable instructions being executable by a computerized device comprising processing hardware to execute the method of the first aspect.

According to a third aspect, there is provided a control apparatus that is configured the use the method of the first aspect to process one or more data inputs in a computing arrangement to provide one or more outputs comprising at least one of control outputs, analysis outputs, or recommendation outputs,
  wherein the control apparatus is configured to execute real-time computing for a multi-dimensional system model spanned by state variables on one or more of finite domains or intervals,
  wherein the one or more data inputs include one or more physical measurands of a system, and the one or more outputs provide a technical modification of the system,
  wherein:
  the control apparatus comprises a system model in which all valid combinations and associated properties or object functions are stored as interconnected relations distributed on one or more computers; and
  the control apparatus is configured to deduce one or more of:
  (i) any sub-space, corresponding to an input statement of states or combinations spanned by one or more state variable or associated properties or object functions, by deriving consequences of the input statement by applying constraints defined by the input statement to the system model; or
  (ii) any sub-space, corresponding to a query, of states or combinations spanned by one or more state variables or associated properties or object functions, by deriving consequences of the query by applying constraints defined by the query to the system model.

By "technical modification" is meant a change in a physical configuration, a physical state or a physical parameter of a system.

Optionally, in the control apparatus, the system comprises one or more of:
  (i) an industrial production facility that is configured to be controlled using the control apparatus;
  (ii) an agricultural production facility that is configured to be controlled using the control apparatus;
  (iii) a healthcare providing facility that is configured to be controlled using the control apparatus;
  (iv) a drug discovery system that is configured to be controlled using the control apparatus;
  (v) a smart metering arrangement that is configured to be controlled using the control apparatus;

(vi) an autonomous and self-drive vehicle driving arrangement that is configured to be controlled using the control apparatus;
(vii) an intelligent drone for surveillance use, wherein the intelligent drone is configured to be controlled using the control apparatus;
(viii) an airborne radar system that is configured to be controlled using the control apparatus; and
(ix) an intelligent apparatus for assisting one or more of medical surgery or treatment, wherein the intelligent apparatus is configured to be controlled using the control apparatus.

More optionally, the control apparatus is configured to provide outputs for controlling operation of one or more of (i) to (ix), and to receive sensor signals from one or more of (i) to (ix).

The aforesaid method is susceptible to being employed, for example, in industrial control apparatus for controlling industrial production facilities, agricultural production facilities (for example, in greenhouses for tomato production; in farm machinery for responsive crop management; in hydroponics facilities for perishable fruit production; in animal husbandry, to provide improved animal welfare), in selective breeding of animals or crops, healthcare providing facilities, smart metering arrangements (for example, in smart energy meters), autonomous vehicle driving arrangements (for example, autonomous and self-drive vehicles), in intelligent drones for surveillance use, in airborne radar systems, in intelligent apparatus for assisting medical surgery and/or treatment, in personal wearable devices and so forth. The method is susceptible to providing control outputs for controlling operation of aforesaid industrial production facilities and so forth, as well as receiving sensor signals from such aforesaid industrial production facilities and so forth. The method is capable of saving resources, for example reducing energy consumption, reducing amounts of physical resources needed for given production in industry and so forth.

Optionally, the method includes representing input state vectors (SV1) associated with asserted and/or measured states of each variable and each object function from an environment in the system model, and representing output state vectors (SV2) associated with one or more deduced consequences on each variable and each object function of the entire system model, when external constraints of the input state vectors (SV1) are colligated with the static constraints in the system model. More optionally, the method includes computing the state of the entire system model in real-time by consulting one or more sub-systems and/or relations at a time by deducing possible states of each variable and propagating one or more bound link variables to connected one or more relations until no further constraints can be added to the state vectors. Yet more optionally, the method includes arranging for the sub-systems to be distributed on a plurality of computing devices and to interact by propagating a common core link variable on each sub-system.

Optionally, the method includes operating the multi-dimensional system model to have a plurality of system model states, and to change state from a given preceding system model state in among the system model states to a subsequent system model state among the system model states, depending upon a computed solution to the given preceding system model state and operative input data applied to the multi-dimensional system model.

According to a fourth aspect, there is provided a control apparatus for processing one or more data inputs in a computing arrangement to provide one or more control outputs and/or one or more analysis output and/or one or more recommendation outputs, characterized in that the control apparatus includes a user interface for interacting with a user of the system for controlling operation of the control apparatus, a data processing arrangement that is operable to receive the one or more data inputs and to output the one or more control outputs and/or one or more analysis output and/or one or more recommendation outputs, wherein the computing arrangement is operable to execute a software product for implementing the aforesaid methods, pursuant to the first and second aspects. The control apparatus is susceptible to being employed, for example, for controlling industrial production facilities, agricultural production facilities (for example, in greenhouses for tomato production; in hydroponics facilities for perishable fruit production; in animal husbandry, to provide improved animal welfare, in selective breeding of crops or animals), healthcare providing facilities, smart metering arrangements (for example, in smart energy meters), autonomous vehicle driving arrangements (for example, autonomous and self-drive vehicles), in intelligent drones for surveillance use, in airborne radar systems, in intelligent apparatus for assisting medical surgery and/or treatment, in personal wearable devices and so forth. The control apparatus is susceptible to providing control outputs for controlling operation of aforesaid industrial production facilities and so forth, as well as receiving sensor signals from such aforesaid industrial production facilities and so forth. The control apparatus is capable of saving resources, for example reducing energy consumption, reducing amounts of physical resources needed for given production in industry and so forth.

According to a fifth aspect, there is provided a welfare system that is configured to provide welfare support to one or more individuals in an assistive environment, wherein the welfare system includes the control apparatus of the third aspect (namely, implementing a PACE engine) that is configured to receive a plurality of measurands of a given individual within the assistive environment, wherein the control apparatus includes a decision support knowledge model including a plurality of treatment strategies and at least one of: drug characteristics, food supplement characteristics, husbandry strategies depending on individual health complications, disease characteristics of each individual, individual genotype data, and SNP data, wherein the control apparatus provides output signals for developing a personalized identification of one or more active drug and food combinations for the treatment or prevention of a given individual's specific disease, and wherein the control apparatus executes a software product that in execution performs a high-order combinatorial search within the decision support knowledge model based upon the plurality of measurands and generates the output signals, characterized in that:
(a) the welfare system is configured to use the given individual's SNP genotypes and/or one or more other features which synergistically affect disease status as a part of the measurands; and
(b) the software product is configured to perform a multi-dimensional solution search in the decision support knowledge model to identify high-order combinations of the given individual's SNP genotypes, using a computational engine (namely, implemented as the PACE engine) with combinatorial methodology for combinatorial feature analysis executed in the data processing arrangement, for each individual within the assistive environment; and (c) the software product is used to compute a welfare trajectory for an individualized welfare of each individual, wherein the welfare trajectory comprises a course of treatment to be prescribed to the given individual.

Optionally, the welfare system further comprises a sensor arrangement that is spatially distributed within the assistive environment, wherein the control apparatus receives sensor signals from the sensor arrangement that is configured to sense environmental conditions for each individual, including monitoring a behaviour and a food intake for each individual, and wherein the control apparatus executes the software product that analyses the sensor signals in respect of the decision support knowledge model by performing a multi-dimensional solution search in the decision support knowledge model based on at least a subset of the sensor signals and a genotype determination by DNA sequencing of each individual within the assistive environment.

Optionally, the welfare system is implemented, such that the control apparatus is configured to execute the high-order combinatorial search in a range of 3 to 20 orders, more optionally in a range of 10 to 20 orders, yet more optionally in a range of 15 to 20 orders, wherein the genomic data is associated with a given gene of the given individual.

Optionally, the welfare system is implemented, such that the control apparatus is configured to execute the high-order combinatorial search in a range of 5 to 13 orders, more optionally in a range of 10 to 20 orders, yet more optionally in a range of 15 to 20 orders, wherein the genomic data is associated with a given gene of the given individual.

Optionally the welfare system is implemented, such that the SNP data includes single nucleotide polymorphisms (SNPs) characterizing each individual, wherein the single nucleotide polymorphisms are determined by using microarrays, DNA sequencing, CRISPR or Polymerase Chain Reaction (PCR) to read genetic tissue samples derived for each individual.

Optionally, the welfare system is configured to collect one or more pathogens present and/or other microorganisms in the assistive environment, to genotype sequence the pathogens and/or other microorganisms to characterize the pathogens and/or other microorganisms, and to use the characterization of the pathogens and/or other microorganisms as an input parameter to the software product when executed in the control apparatus to use when performing its search for computing the welfare trajectory for the individualized welfare of each individual.

Optionally, the welfare system is implemented such that the output signals are used to control at least one of:
(i) type and/or quantity of food provided to the individuals;
(ii) a time when food is provided to the individuals;
(iii) additional food supplements and/or one or more drugs to be administered to the individuals;
(iv) changes to husbandry practices including selective heating or cooling to be supplied to the individuals; and
(v) pathogen reducing processes to be applied to the assistive environment.

Optionally, the welfare system is configured to analyse the given individual's entire genome including such structural variants, copy number variants, epigenetic and expression levels as may be present from the given individual's tumour biopsy provided as measurands to the control apparatus, to capture a tumour network pertaining to the given individual's entire genome and that of their tumour.

Optionally, the welfare system is implemented, such that the control apparatus is configured to find high-order combinations of SNP genotypes, clinical, epidemiological, phenotypic, environmental and other features which synergistically affect a disease status of the given individual represented in the input parameters. More optionally, the welfare system is configured to identify a treatment for the disease that is selected from a group including: metabolic, cancer, cardiovascular, immunological, neurodegenerative, neuropsychiatric and respiratory disease. More optionally, the welfare system is implemented such that the control apparatus data is configured to devise a course of treatment for the given individual, wherein the treatment is based upon the patient individual's SNP genotype and at least one non-genomic feature of the given individual.

According to a sixth aspect, there is provided a method for using a welfare system to provide welfare support to a plurality of individuals in an assistive environment, wherein the welfare system includes a control apparatus of the third aspect (that implements the aforesaid PACE engine) that is configured to receive a plurality of measurands of a given individual within the assistive environment, wherein the control apparatus includes a decision support knowledge model including a plurality of treatment strategies and at least one of: drug characteristics, food supplement characteristics, husbandry strategies depending on individual health complications, disease characteristics of each individual, individual genotype data, SNP data, clinical, epidemiological, phenotypic, and environmental data wherein the control apparatus is configured to provide output signals for developing a personalized identification of one or more active drug combinations for the treatment or prevention of a given individual's specific disease, and wherein the control apparatus is configured to execute a software product to perform a high-order combinatorial search within the decision support knowledge model based upon the plurality of measurands and to generate the output signals, characterized in that the method includes:
(a) employing the given individual's SNP genotypes and/or one or more other features which synergistically affect disease status as a part of the measurands;
(b) arranging for the software product to perform a multi-dimensional solution search in the decision support knowledge model to identify high-order combinations of the given individual's SNP genotypes, using a computational engine (namely implemented as the aforesaid PACE engine), with combinatorial methodology for combinatorial feature analysis executed in the control apparatus, for each individual within the assistive environment; and
(c) using the software product to compute a welfare trajectory for an individualized welfare of each individual, wherein the welfare trajectory comprises a course of treatment to be prescribed to the given individual.

Optionally, the welfare system further comprises a sensor arrangement that is spatially distributed within the assistive environment, wherein the method comprises arranging for the control apparatus to:
(a) receive sensor signals from the sensor arrangement that is configured to sense environmental conditions for each individual, including monitoring a food intake for each individual, and
(b) execute the software product that analyses the sensor signals in respect of the decision support knowledge model by performing a multi-dimensional solution search in the decision support knowledge model based on at least a subset of the sensor signals and a genotype determination by DNA sequencing of each individual hosted within the assistive environment.

Optionally, the method includes selecting the SNP genotypes from SNP genotypes present in non-coding regions of genes, in the intergenic regions or in coding regions of genes.

Optionally, the method includes arranging for the SNP data to include single nucleotide polymorphisms (SNPs) characterizing each individual, determined by using microarrays, DNA sequencing, CRISPR or Polymerase Chain Reaction (PCR) to read genetic tissue samples derived for each individual.

According to a seventh aspect, there is provided a computer program product comprising a non-transitory computer readable storage medium having computer-readable instructions stored thereon, the computer-readable instructions being executable by a computerized device comprising processing hardware to execute the method of the sixth aspect.

Additional aspects, advantages, features and objects of the present disclosure would be made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

DESCRIPTION OF THE DIAGRAMS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and apparatus disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
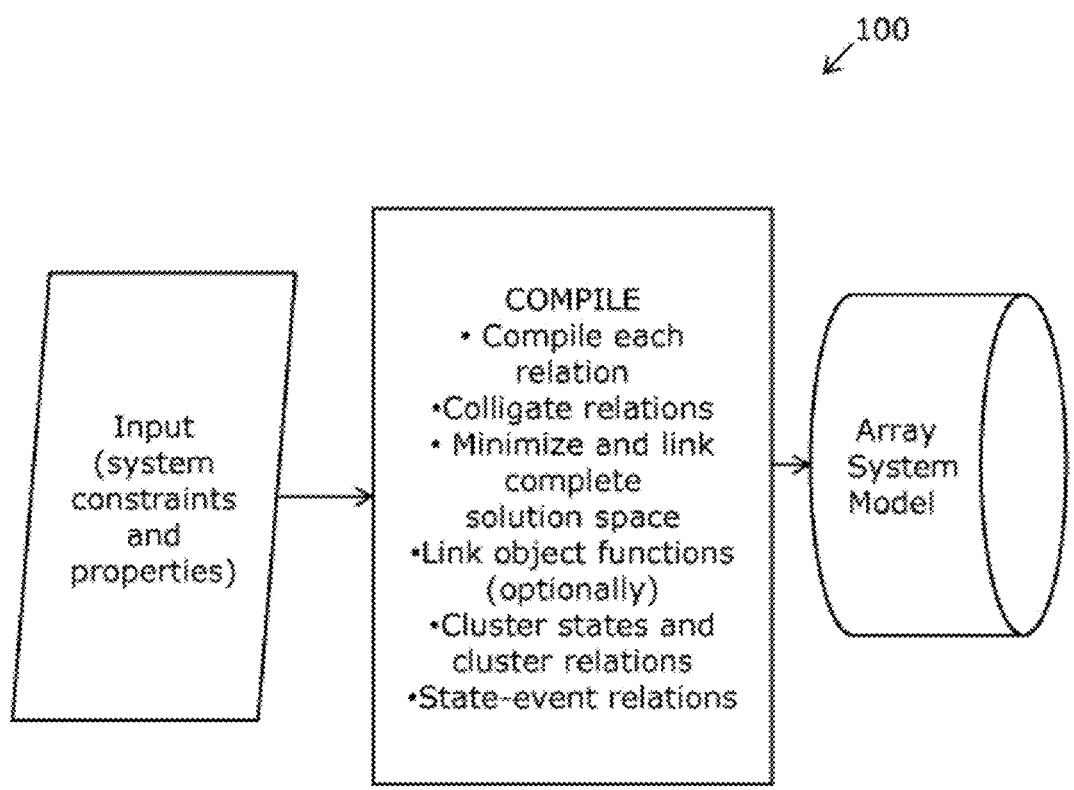
FIG. 1 is an illustration of an array system model, namely a multi-dimensional system model, employed in embodiments of the present disclosure.
Figure 6:
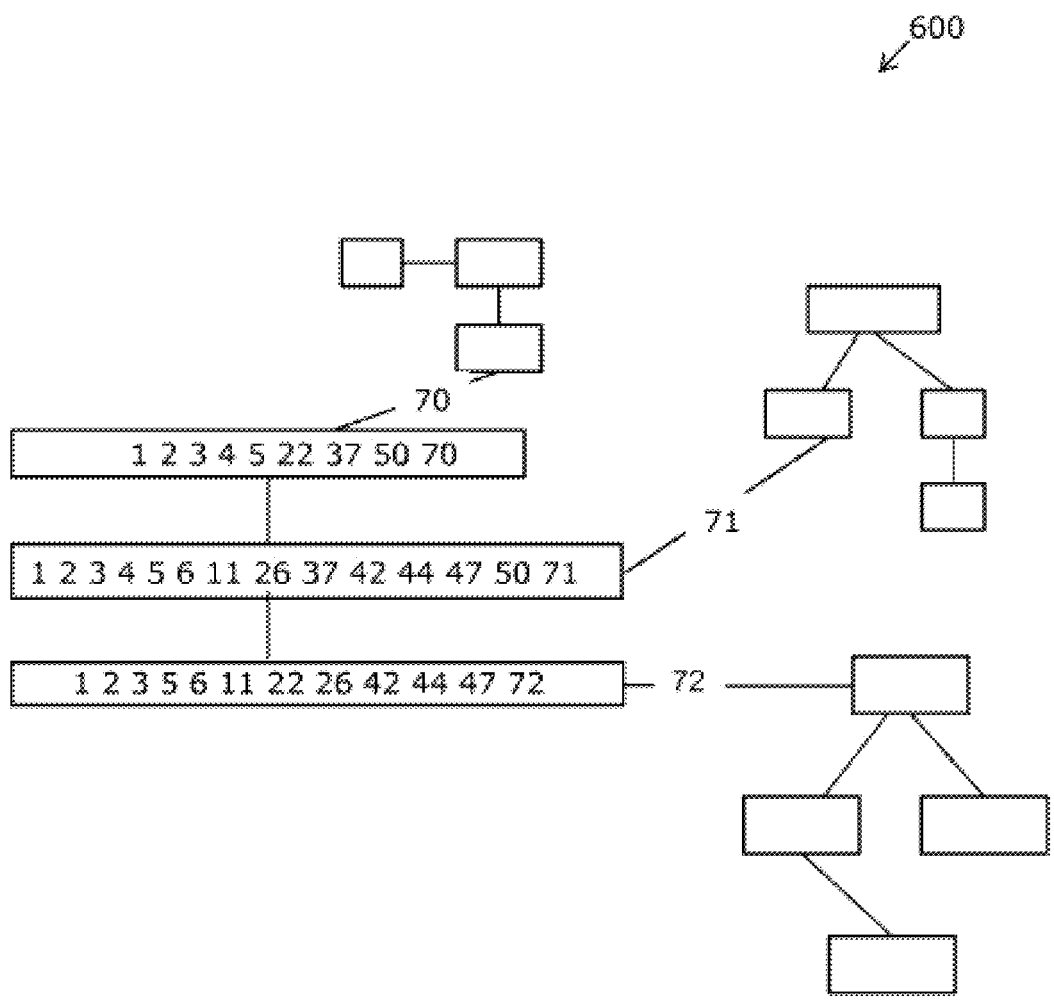
Figure 7:
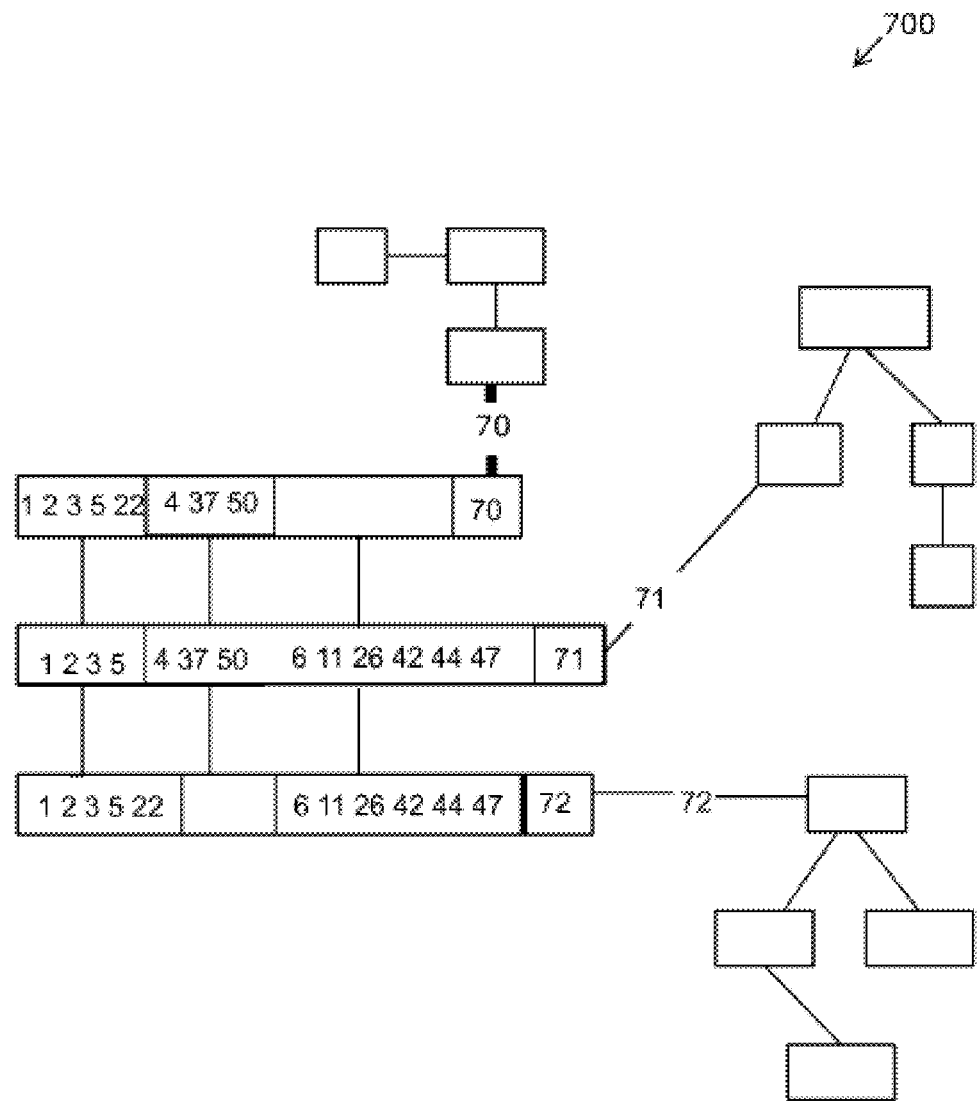
Figure 8:
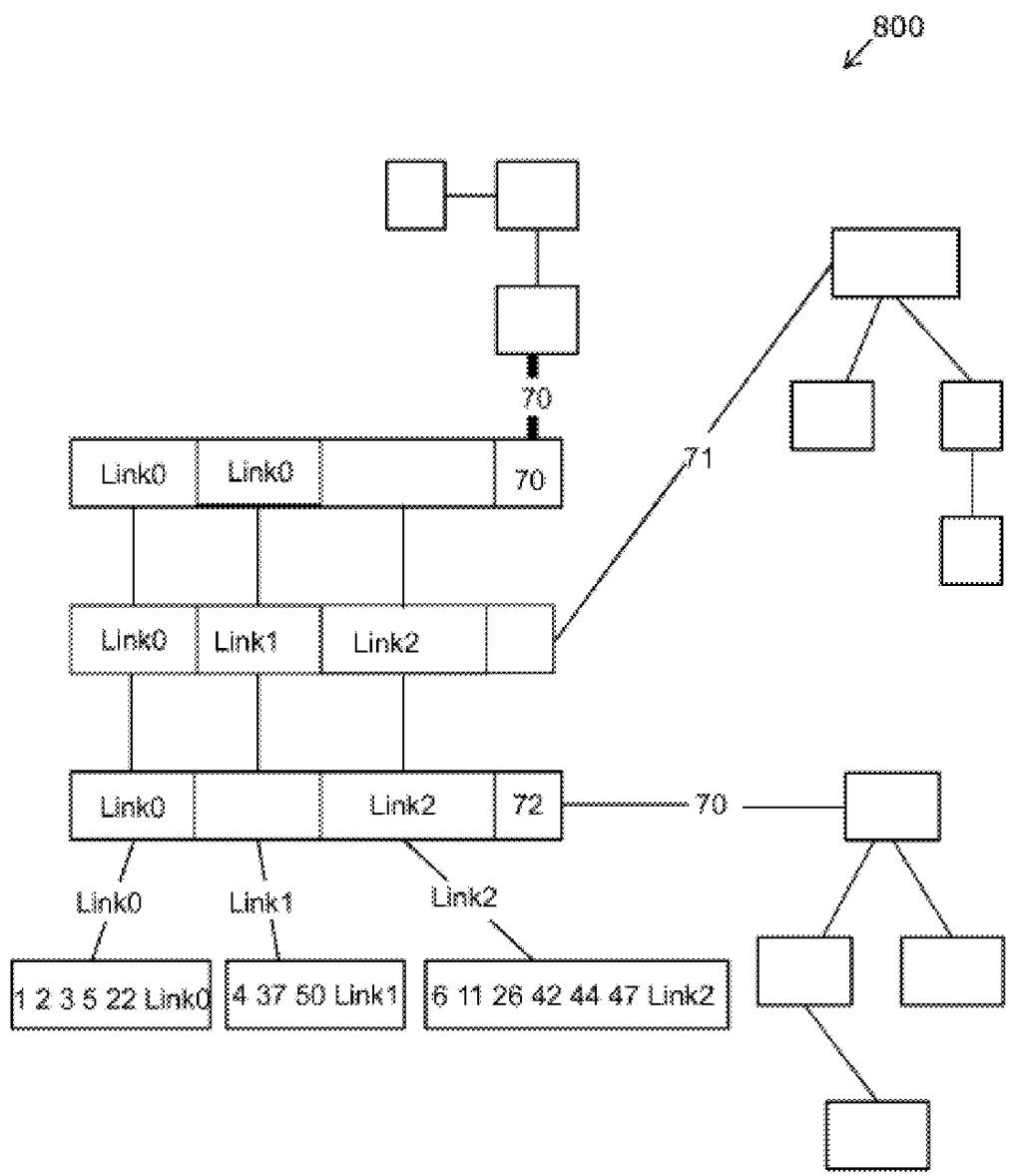
Figure 9:
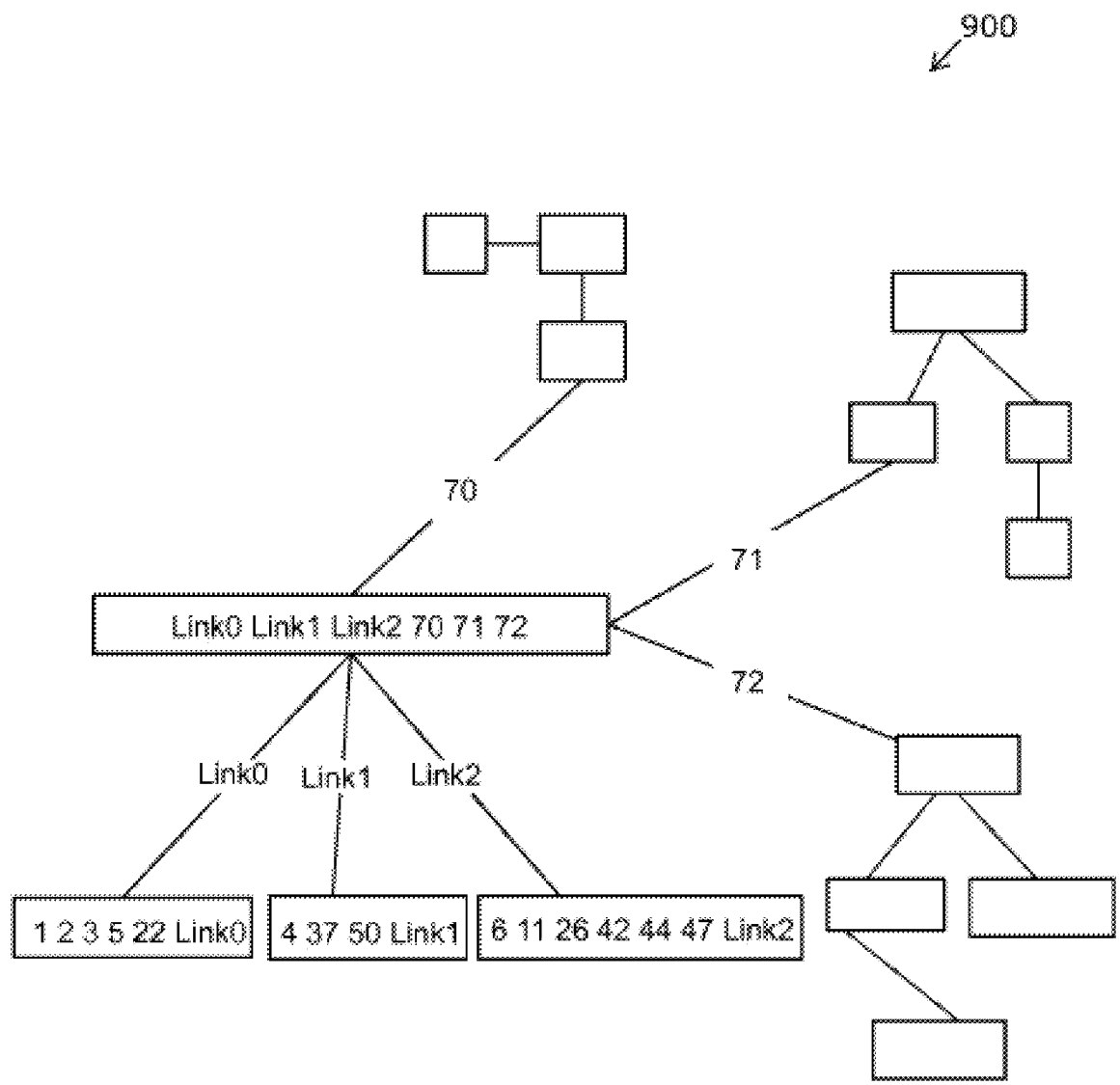
Figure 10:
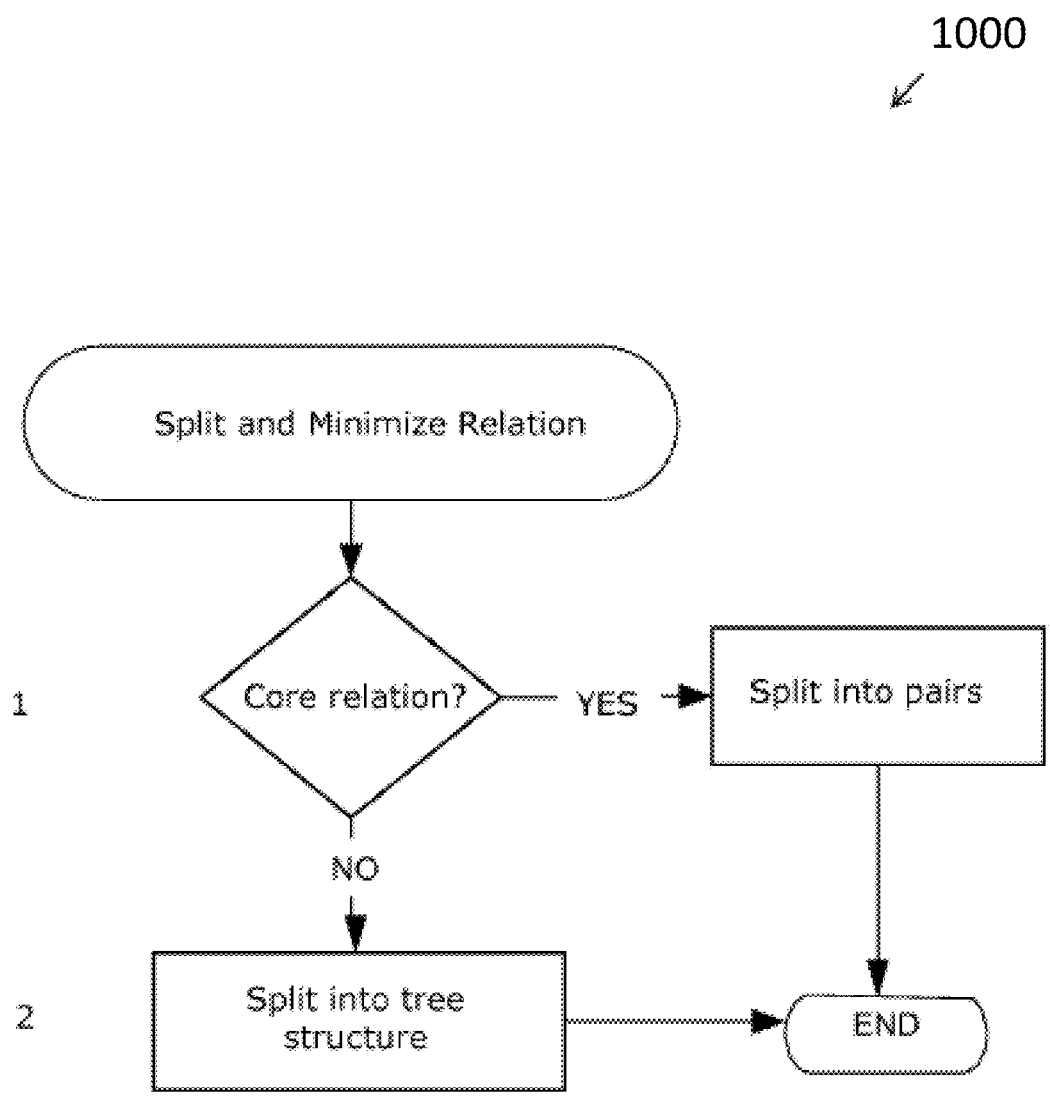
Figure 11:
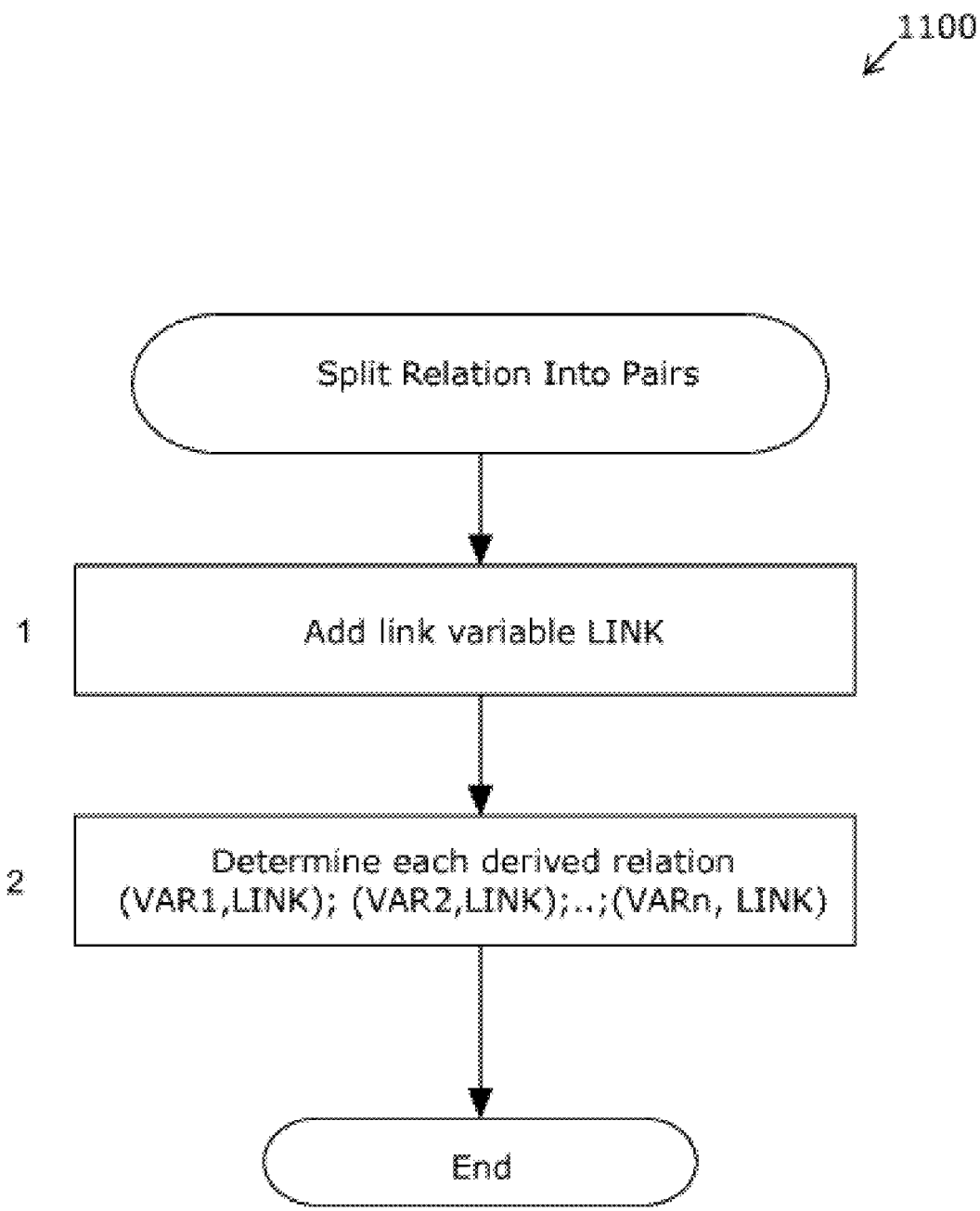
Figure 12:
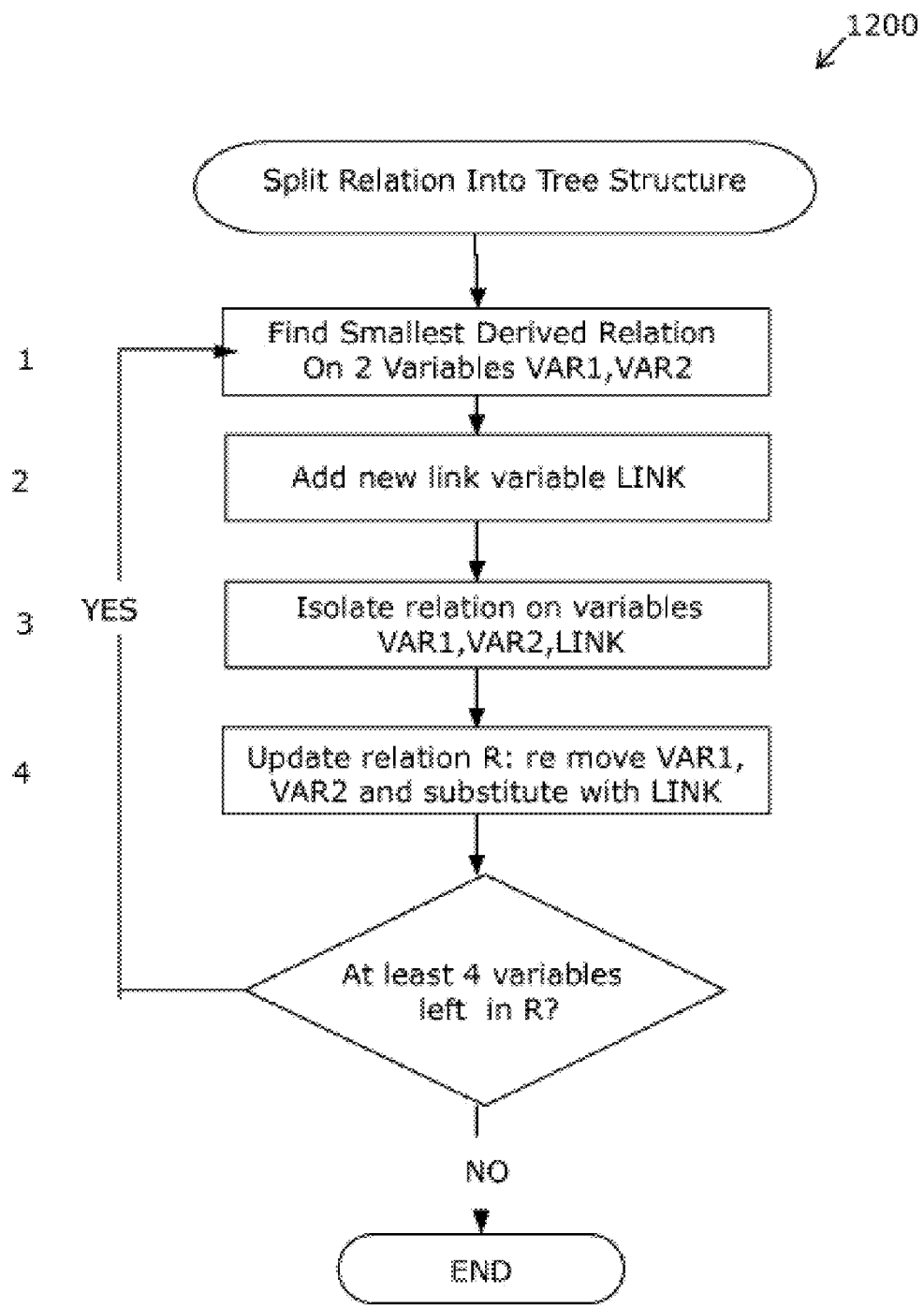
Figure 13:
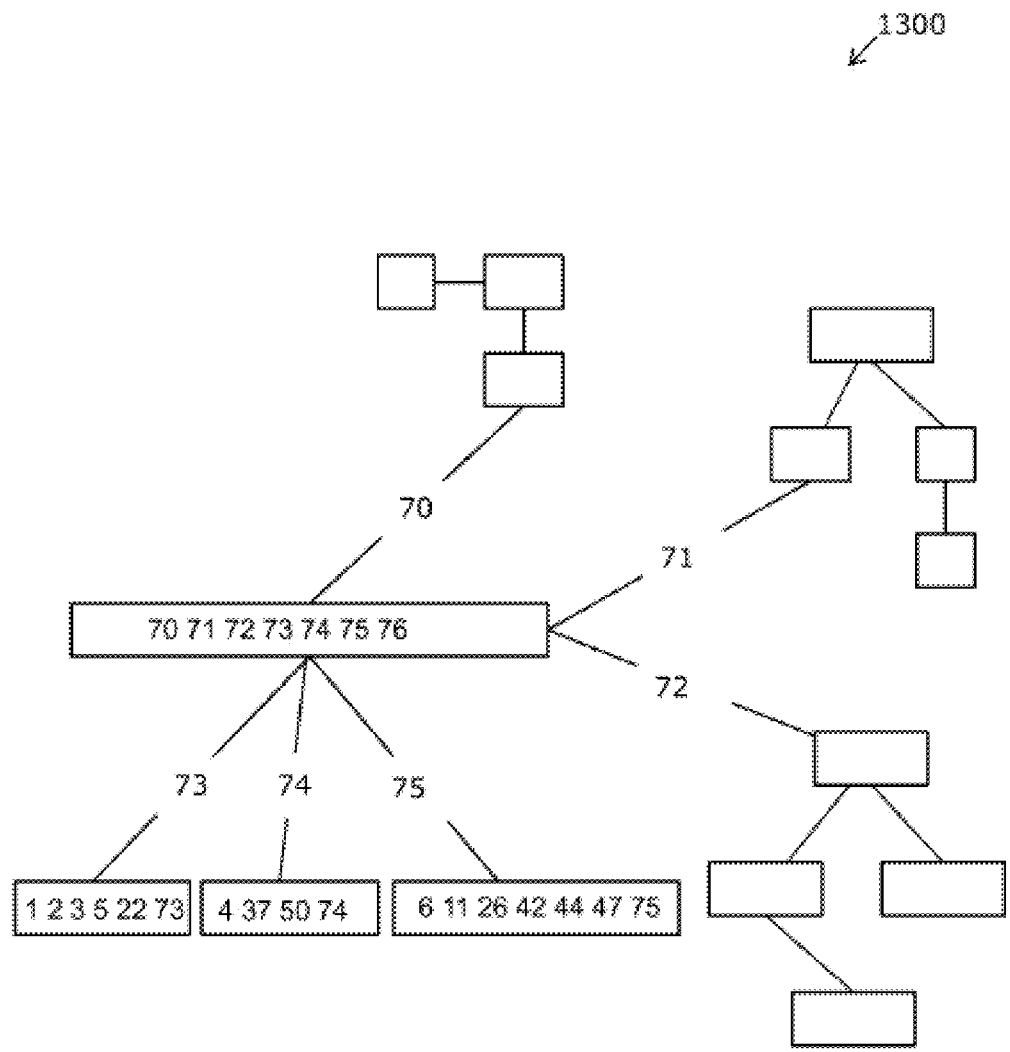
Figure 14:
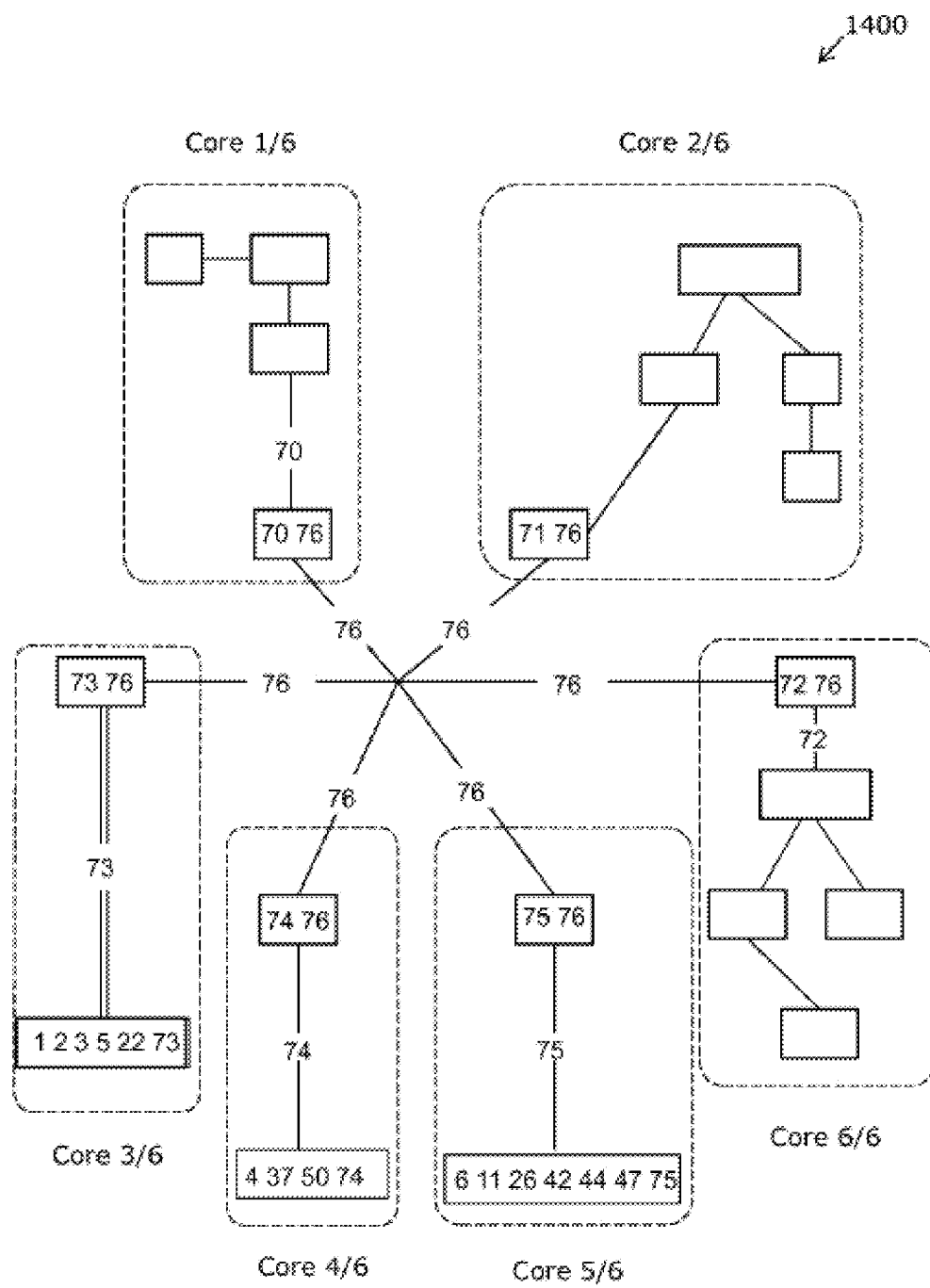
Figure 15:
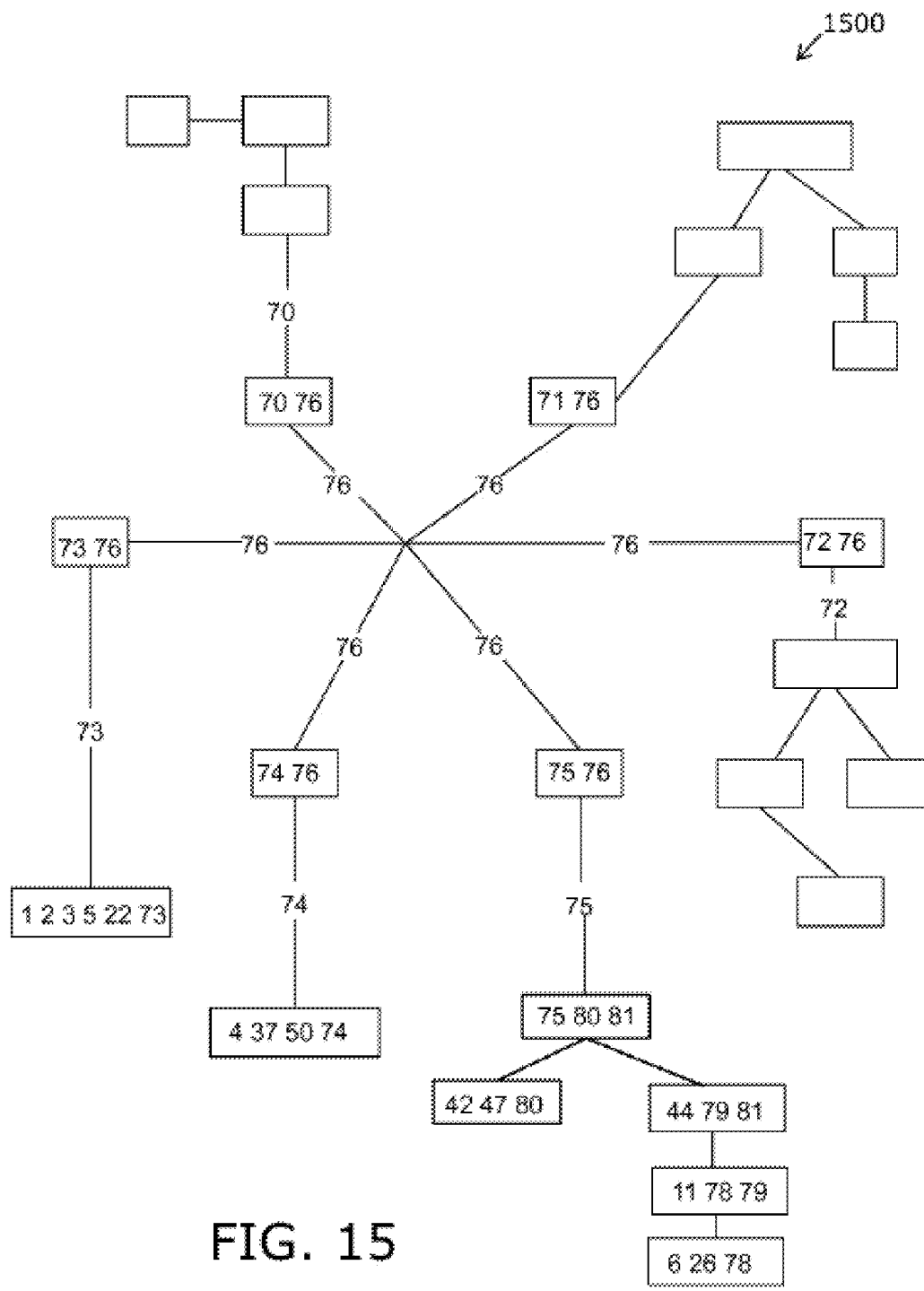
Figure 16:
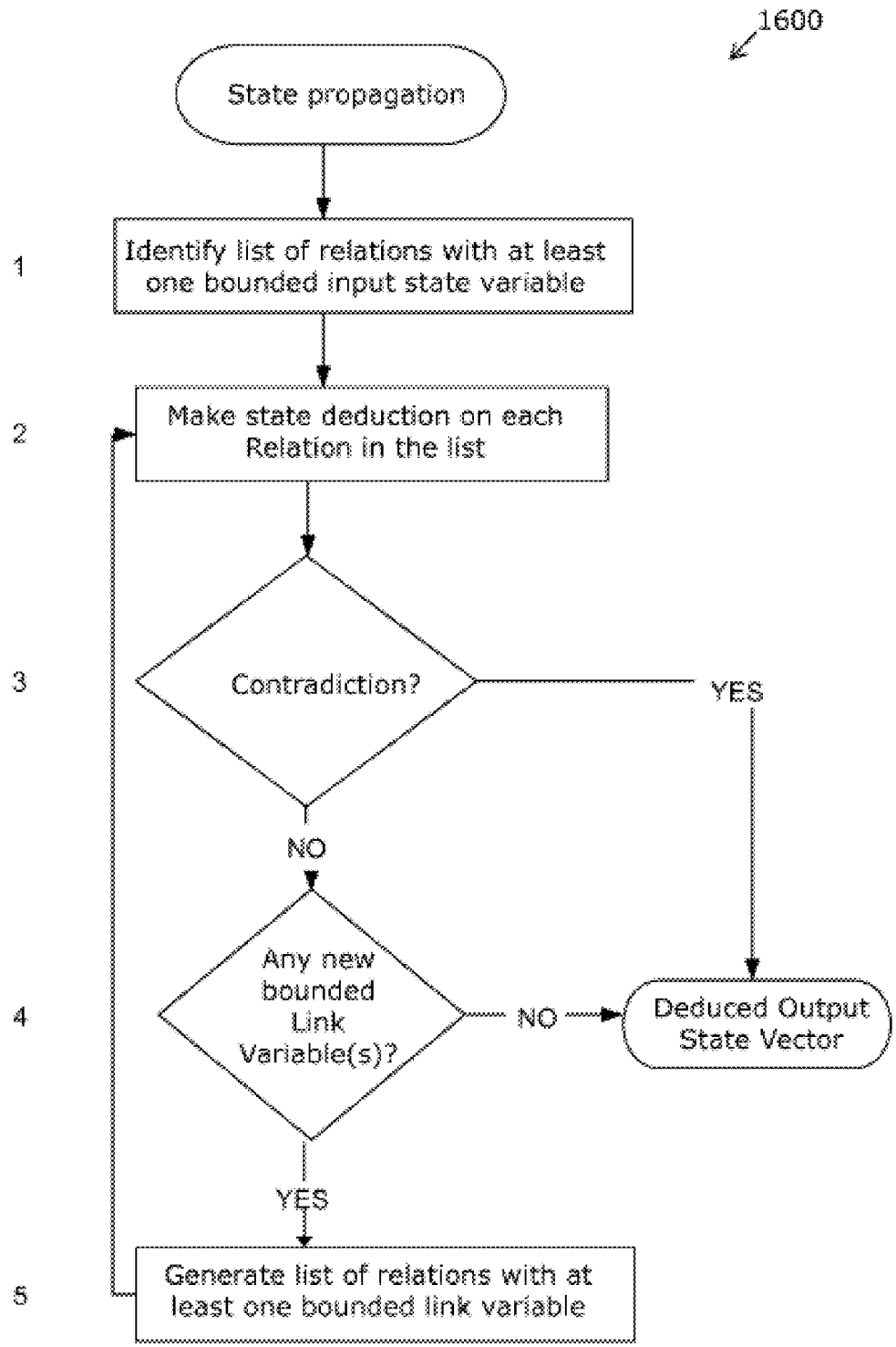
Figure 17:
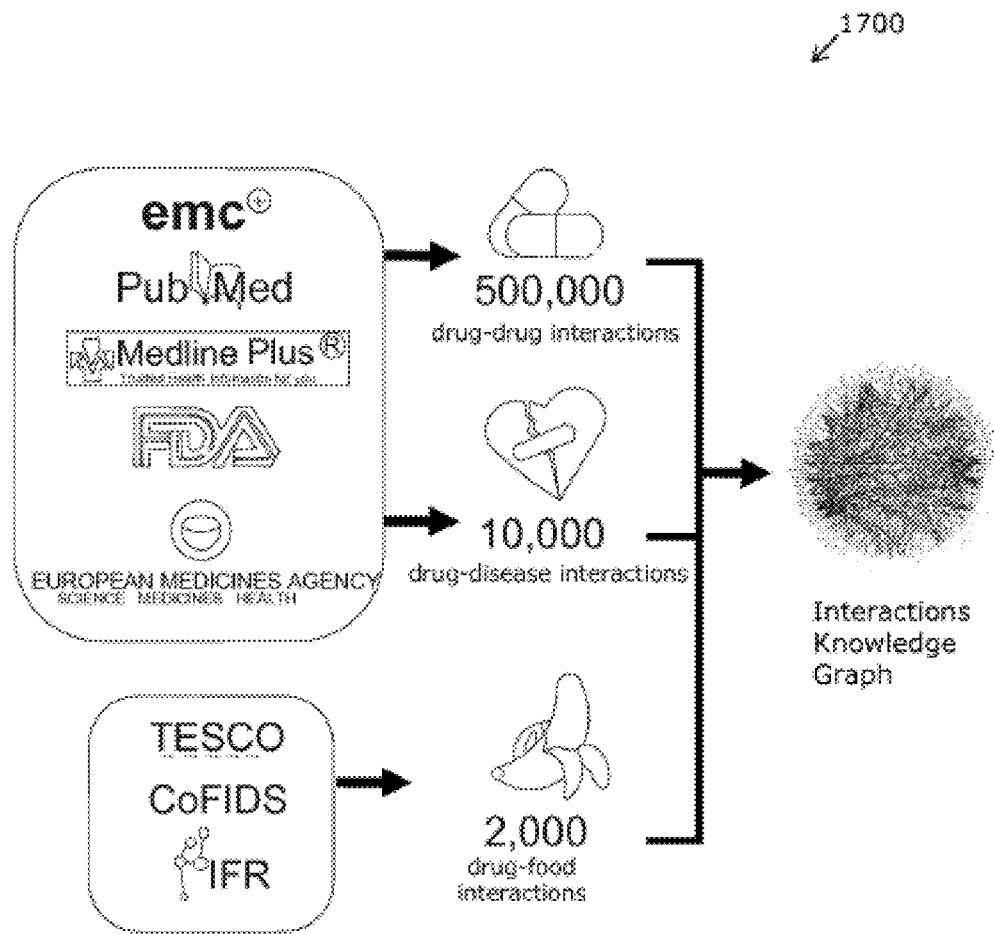
Figure 18:
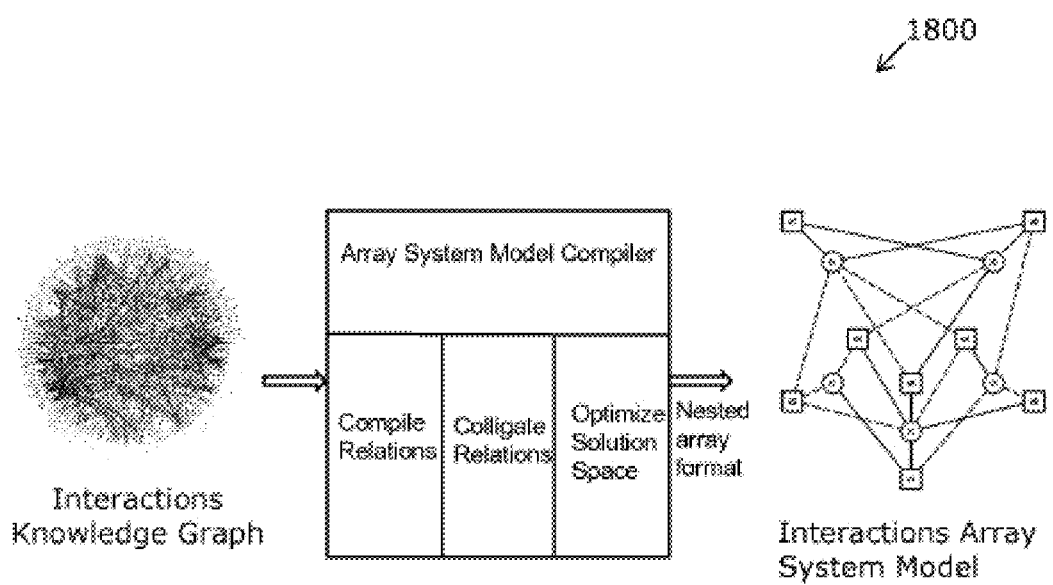
Figure 19:
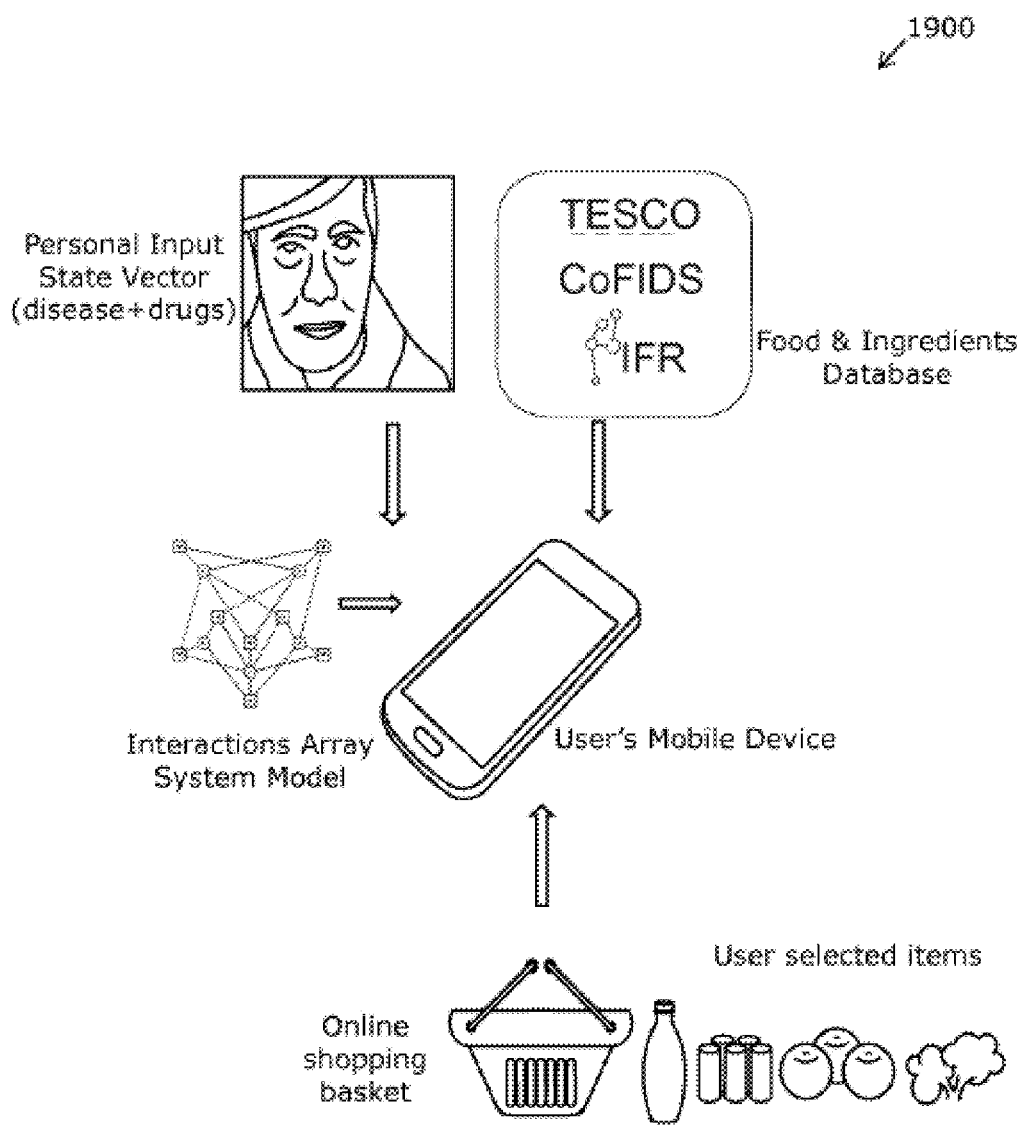
Figure 20:
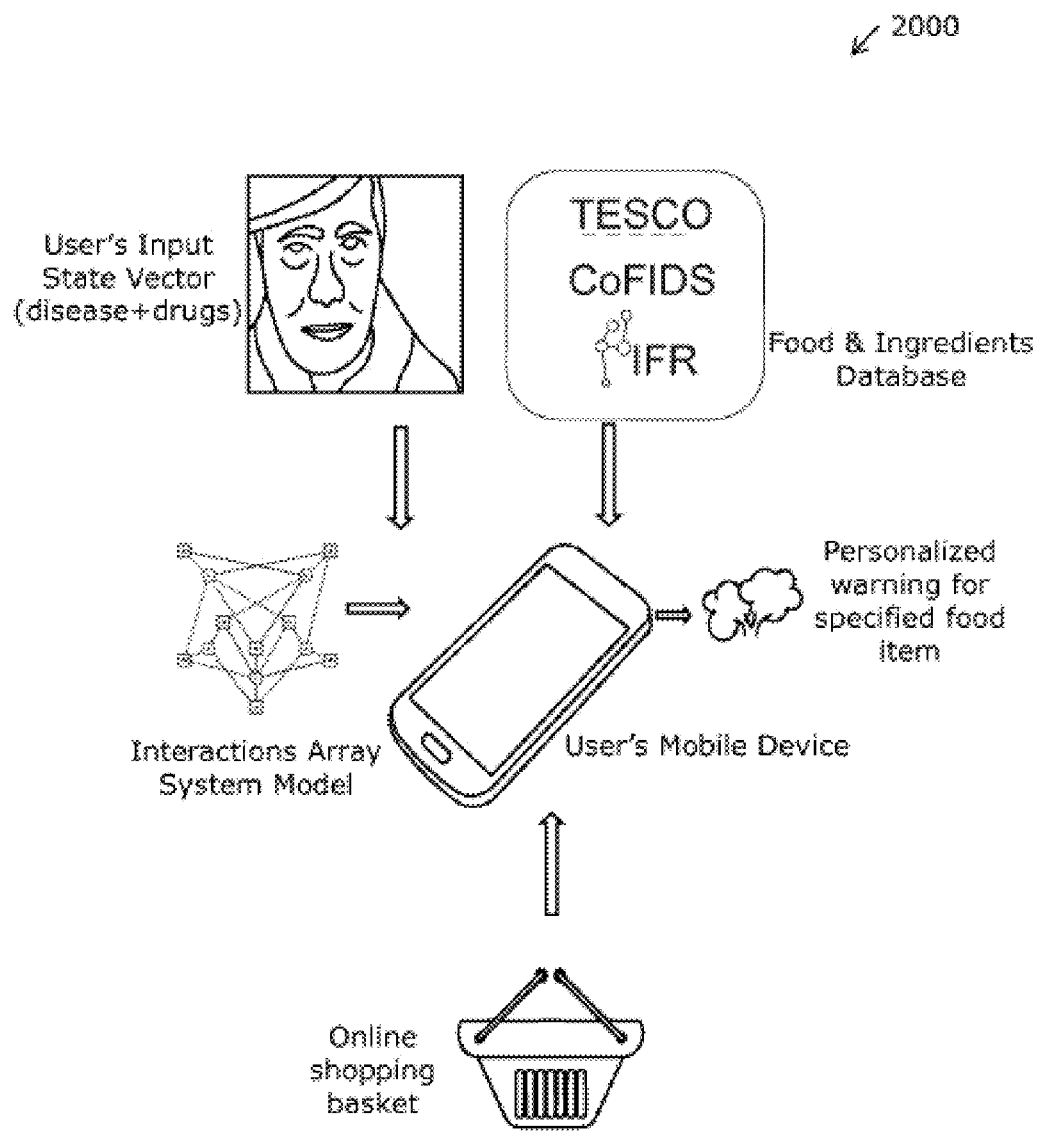
Figure 21:
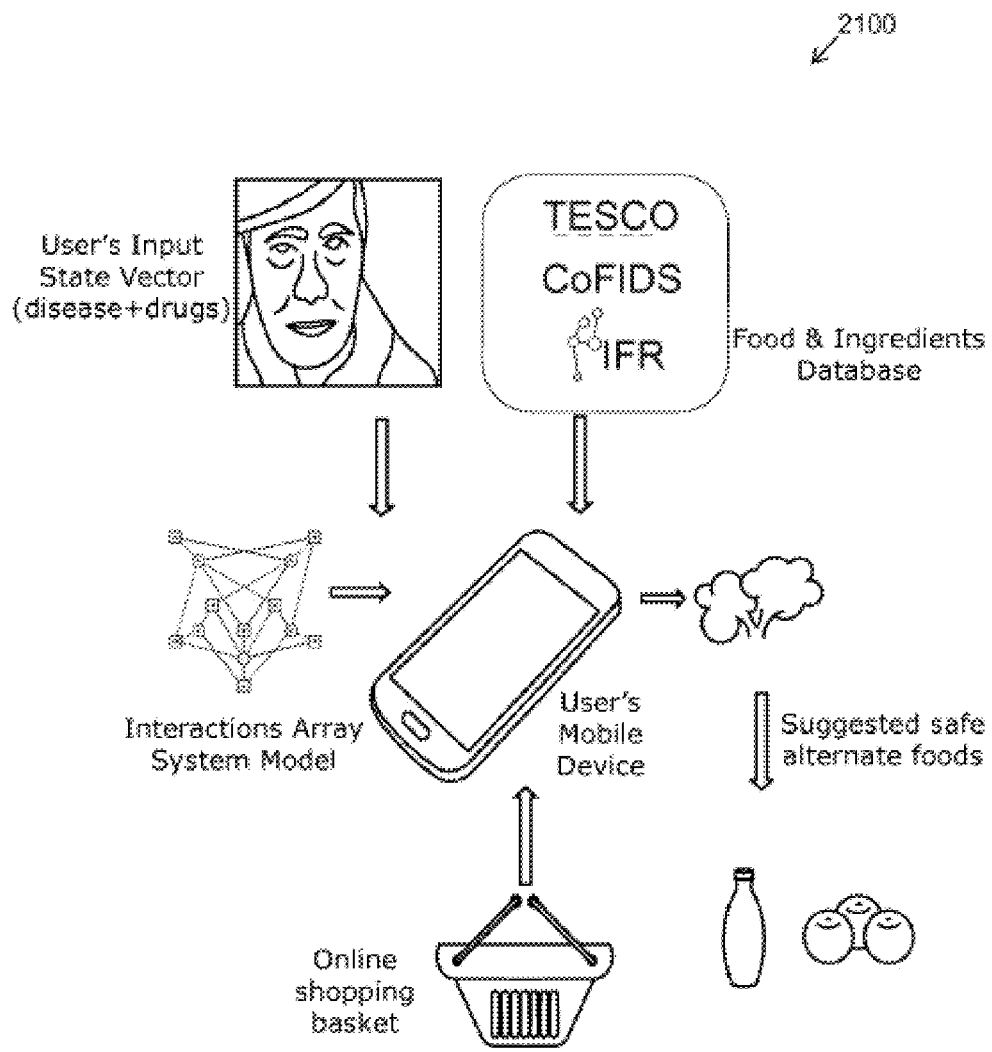
Figure 22:
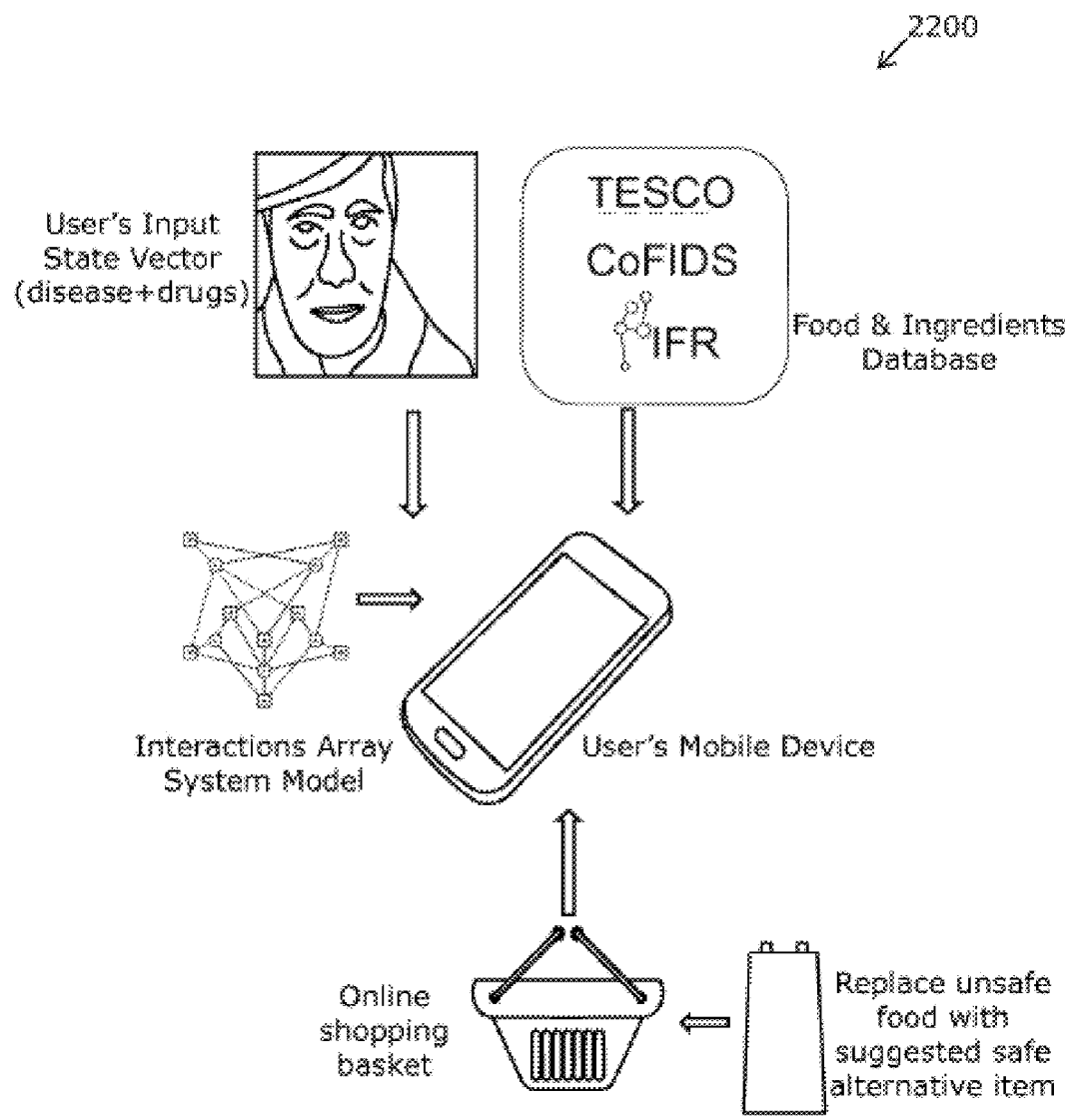
Figure 23:
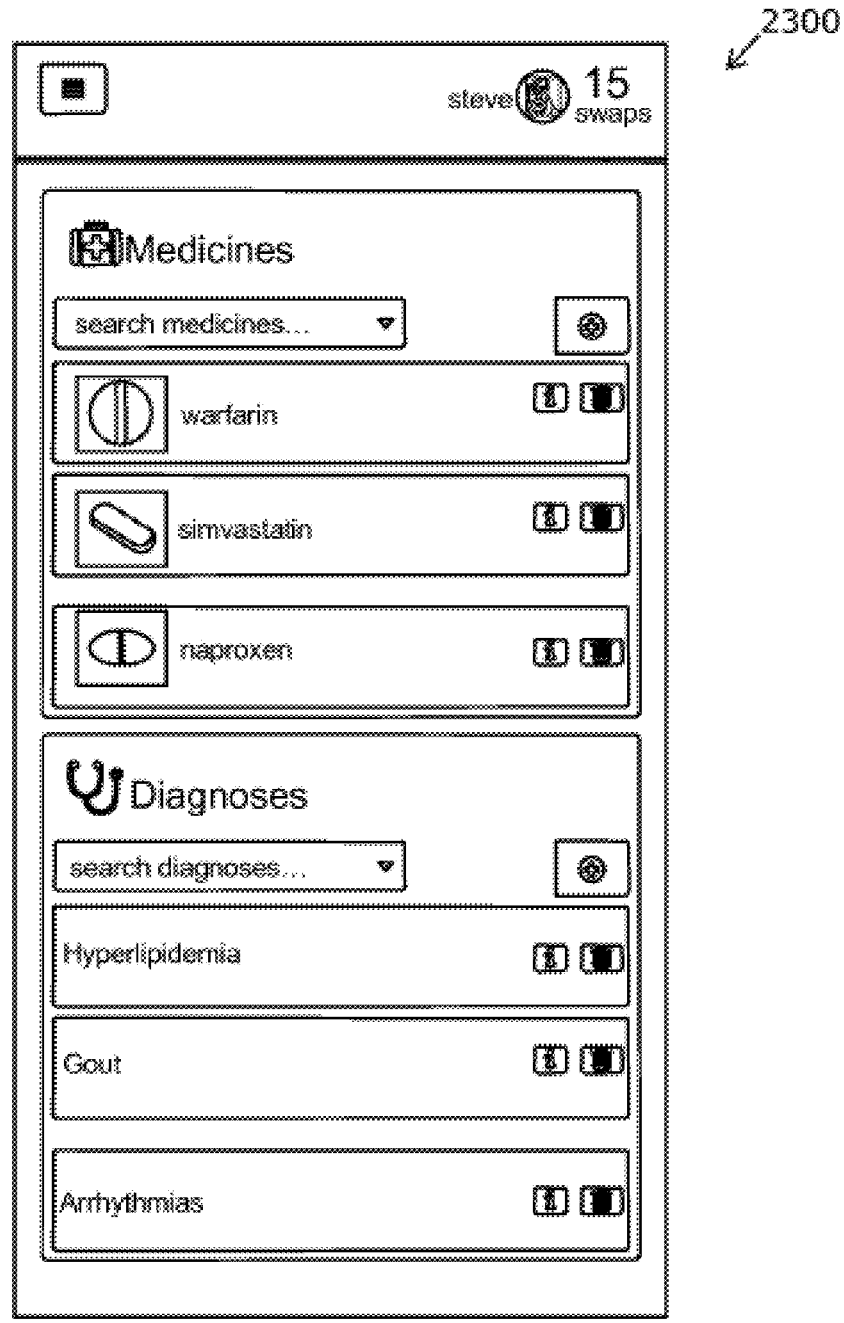
Figure 24:
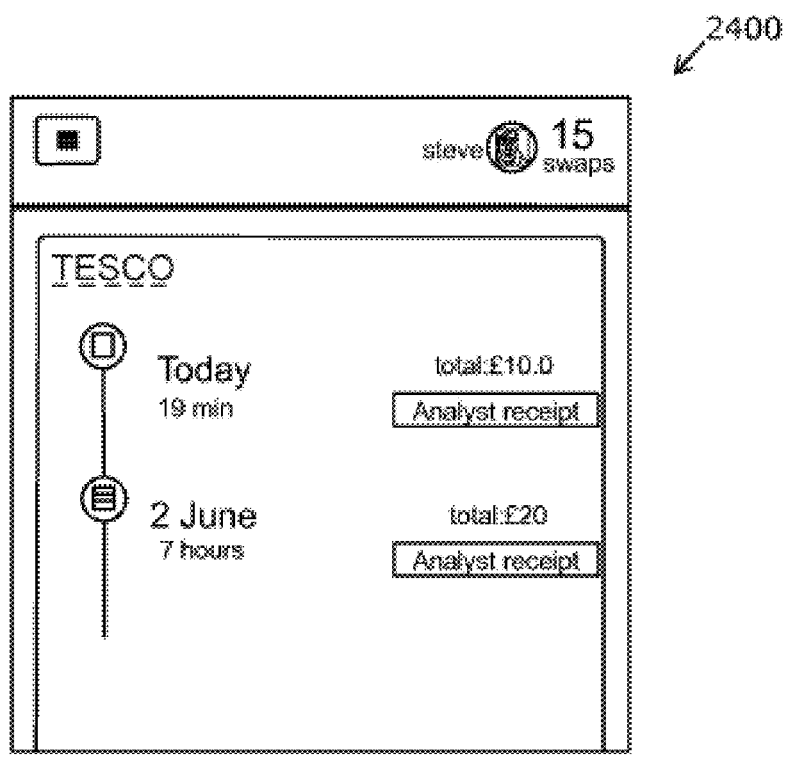
Figure 25:
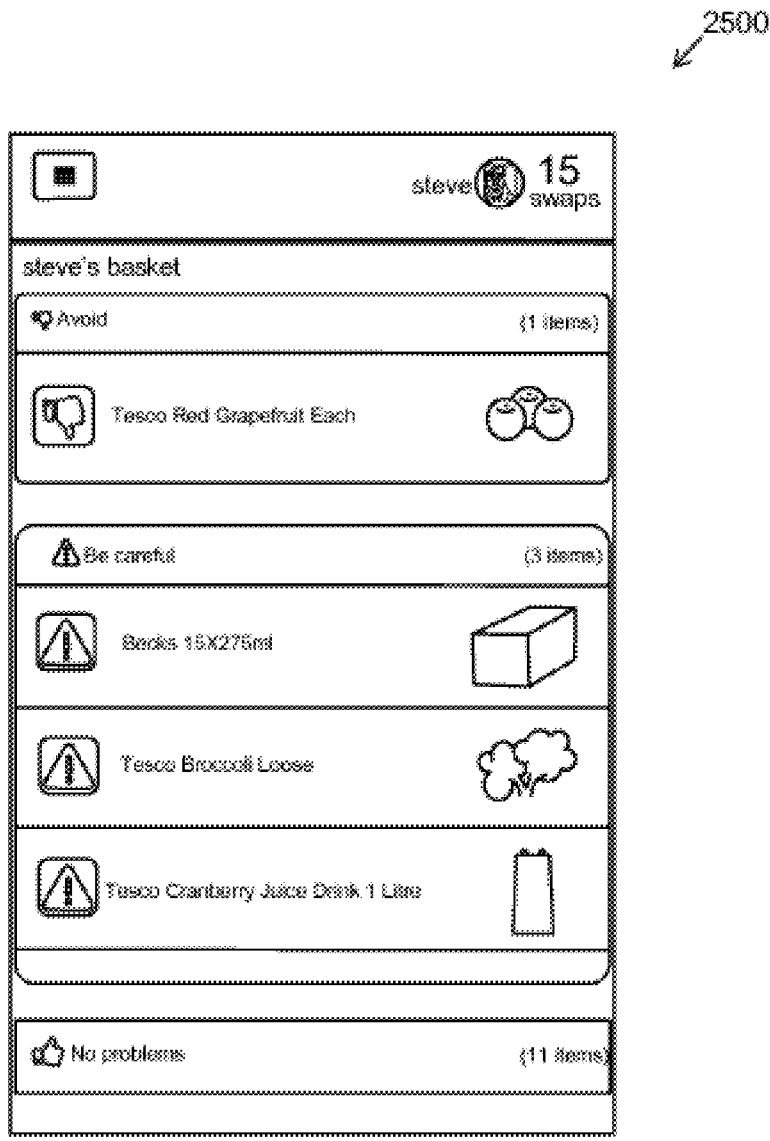
Figure 26:
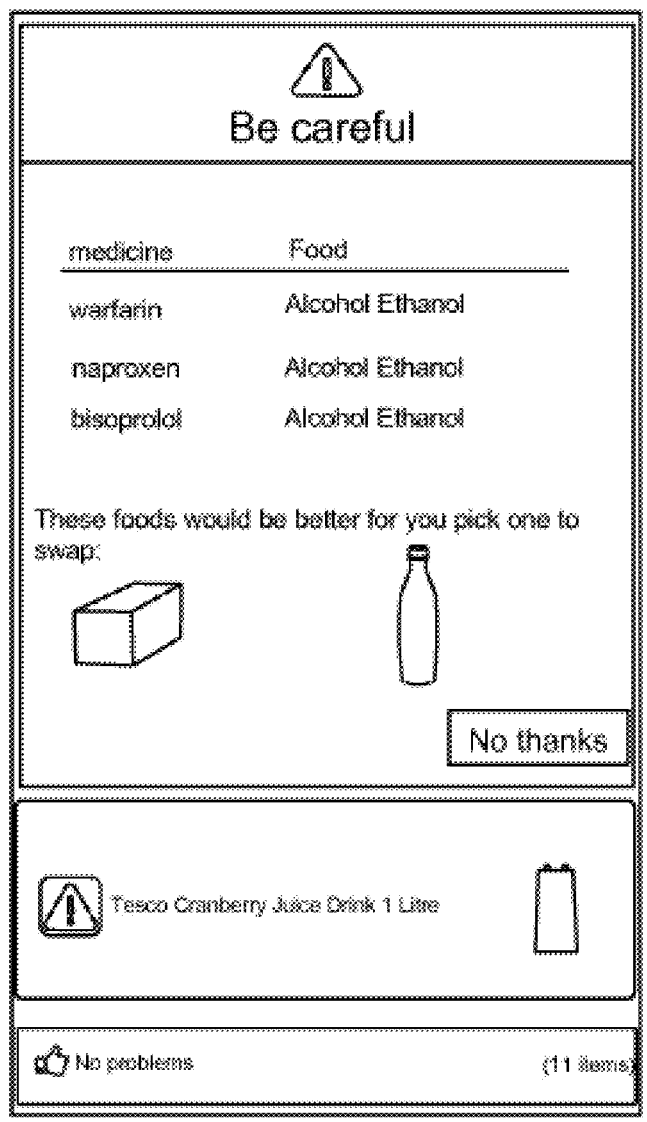
Figure 28:
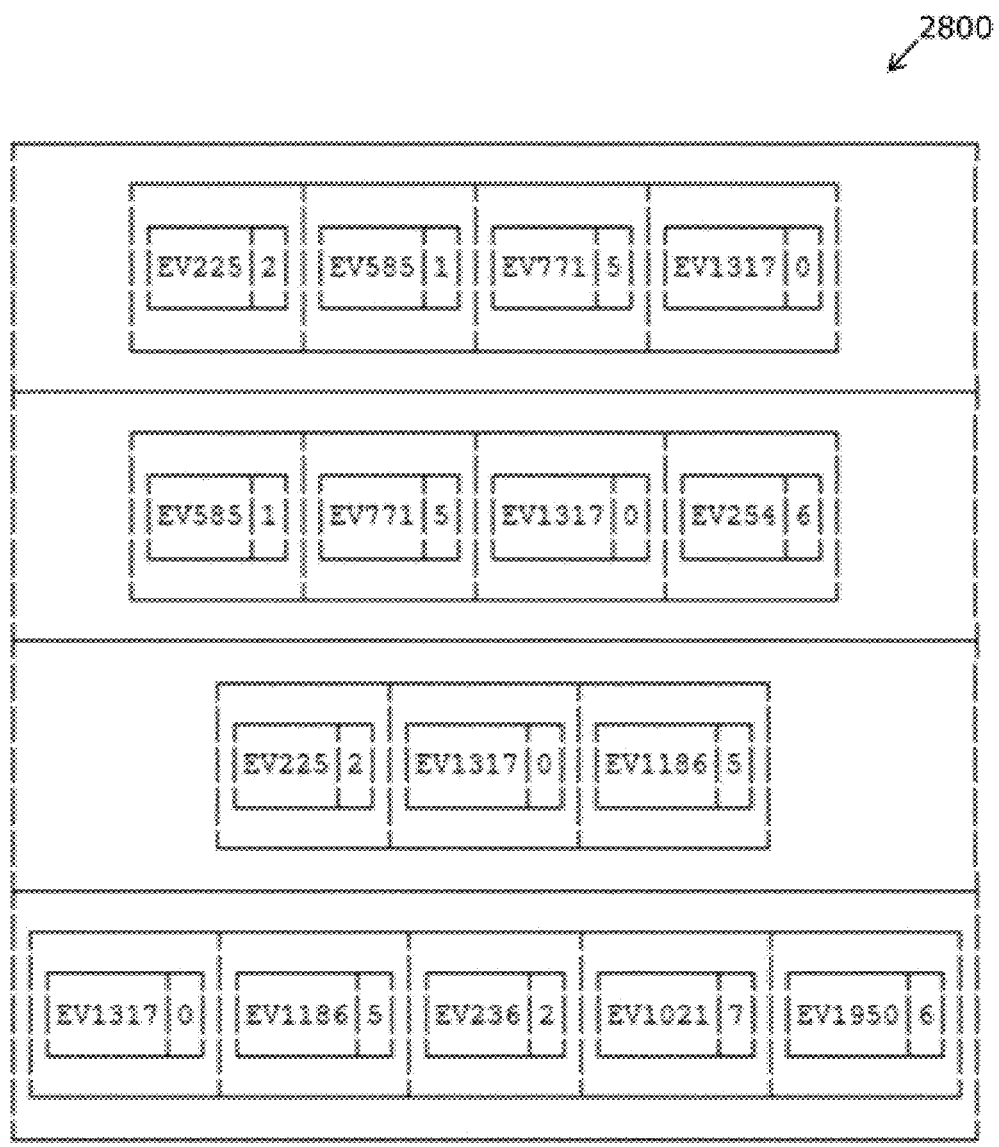
Figure 30:
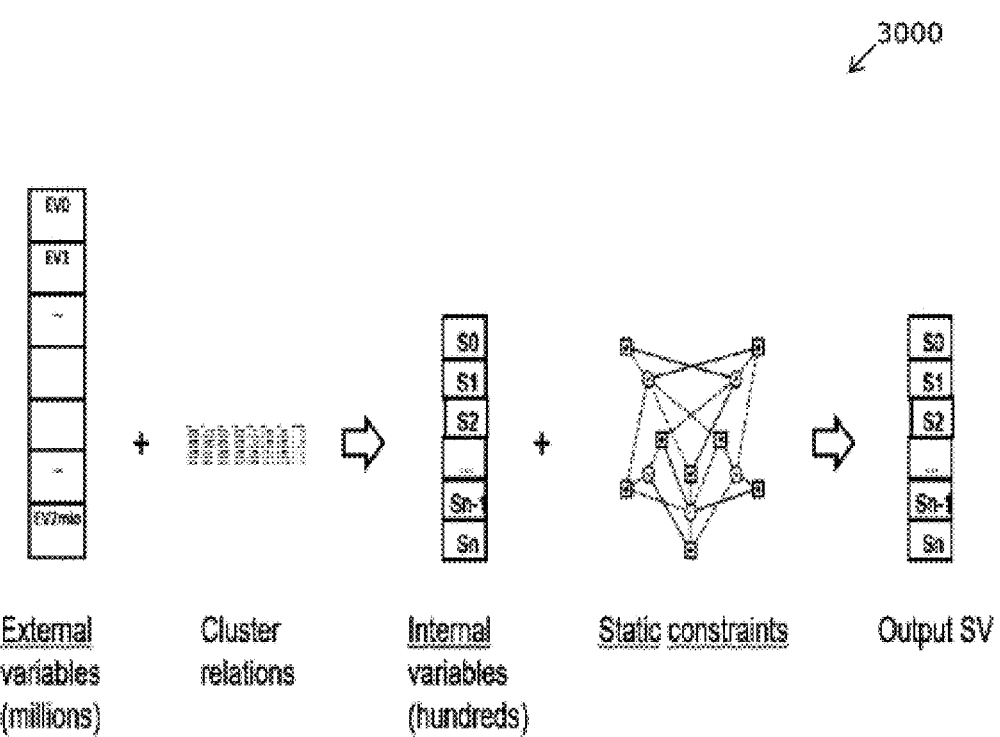
Figure 31:
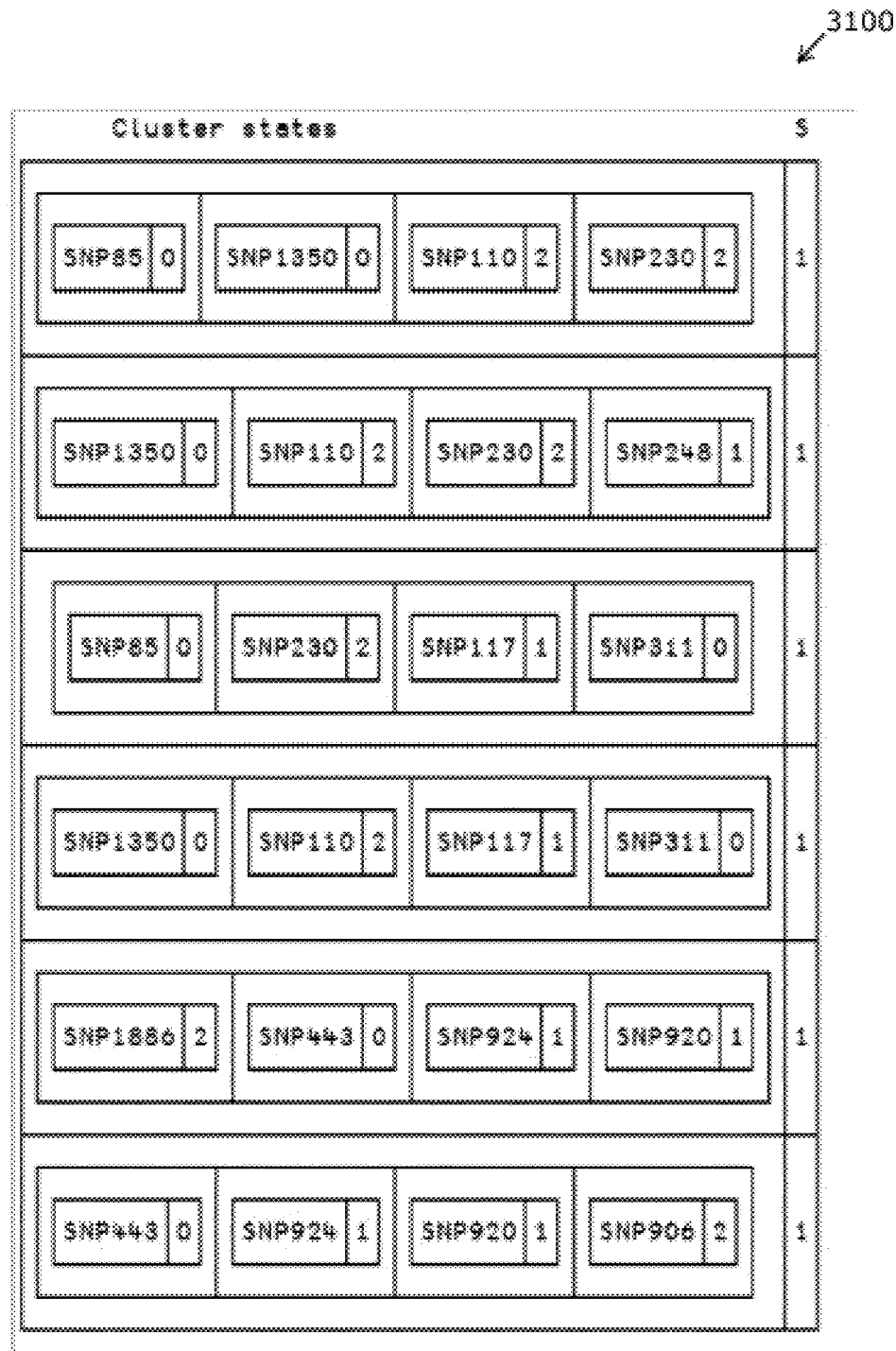
Figure 33:
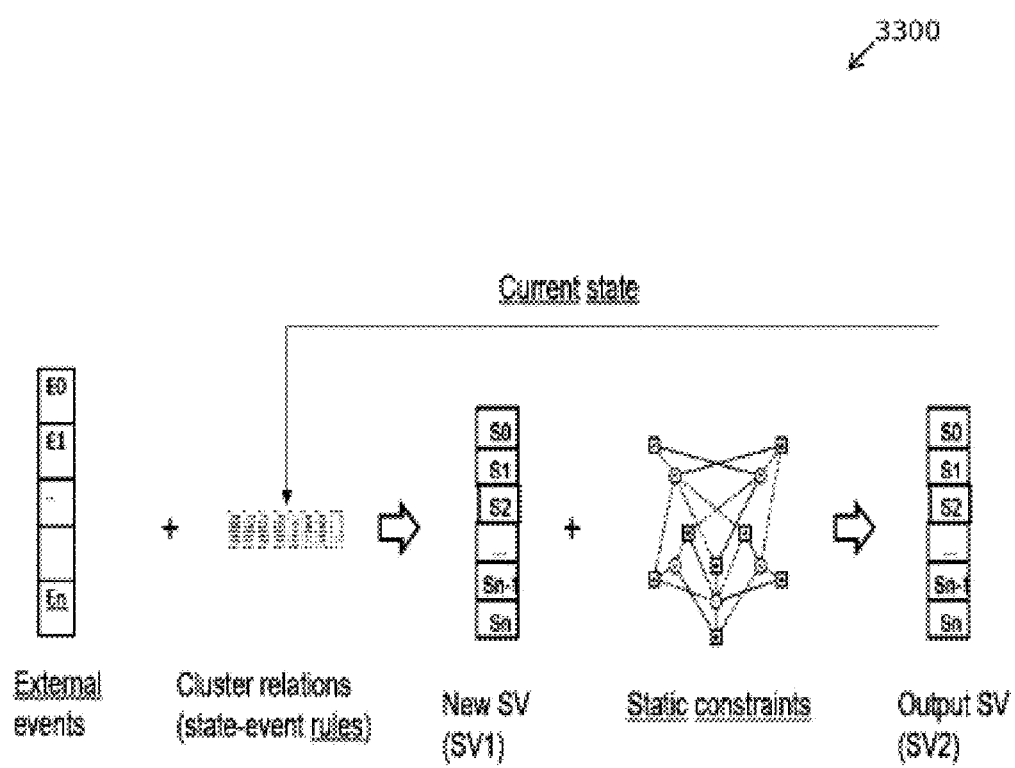
Figure 34A:
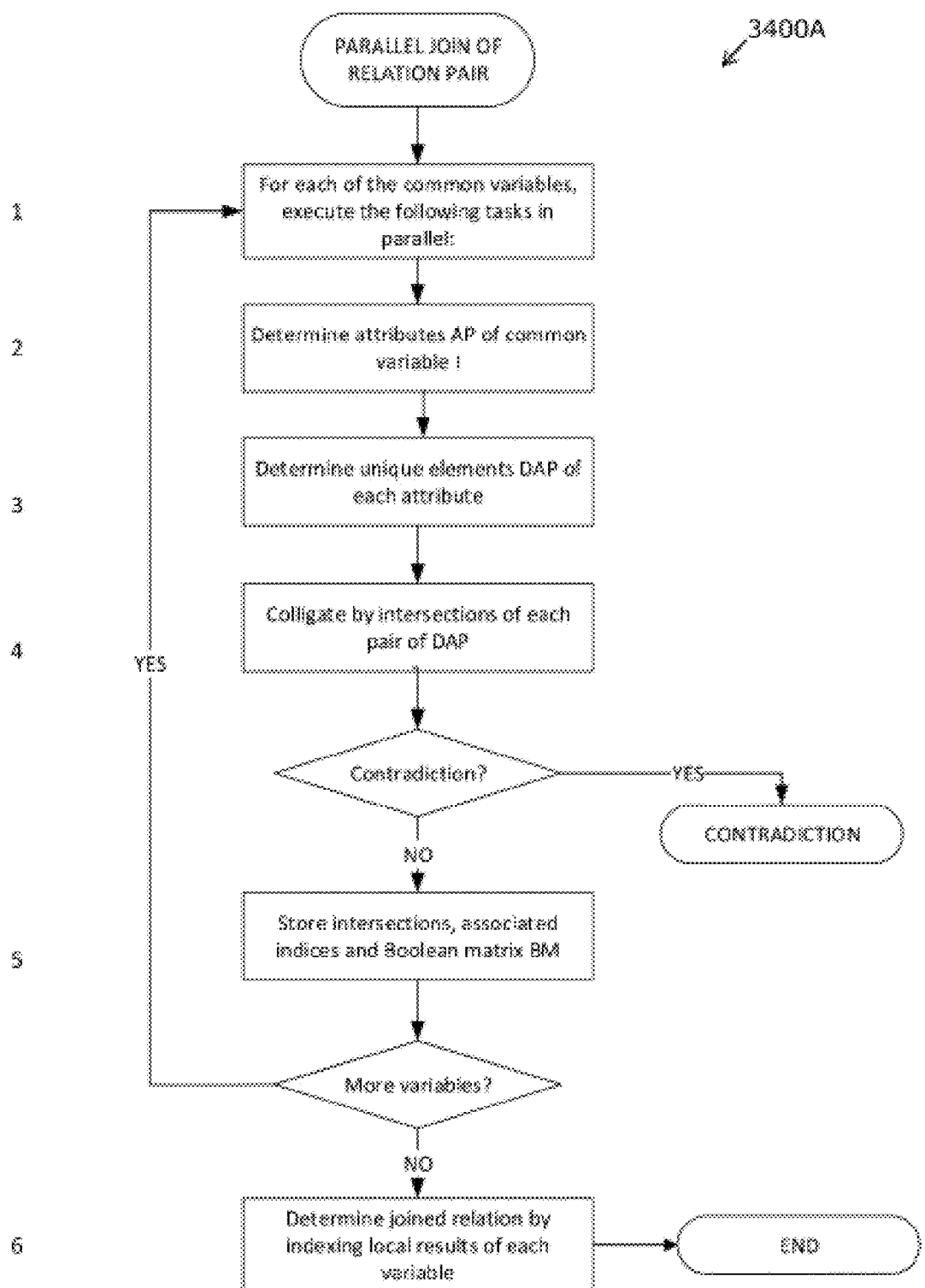
Figure 39:
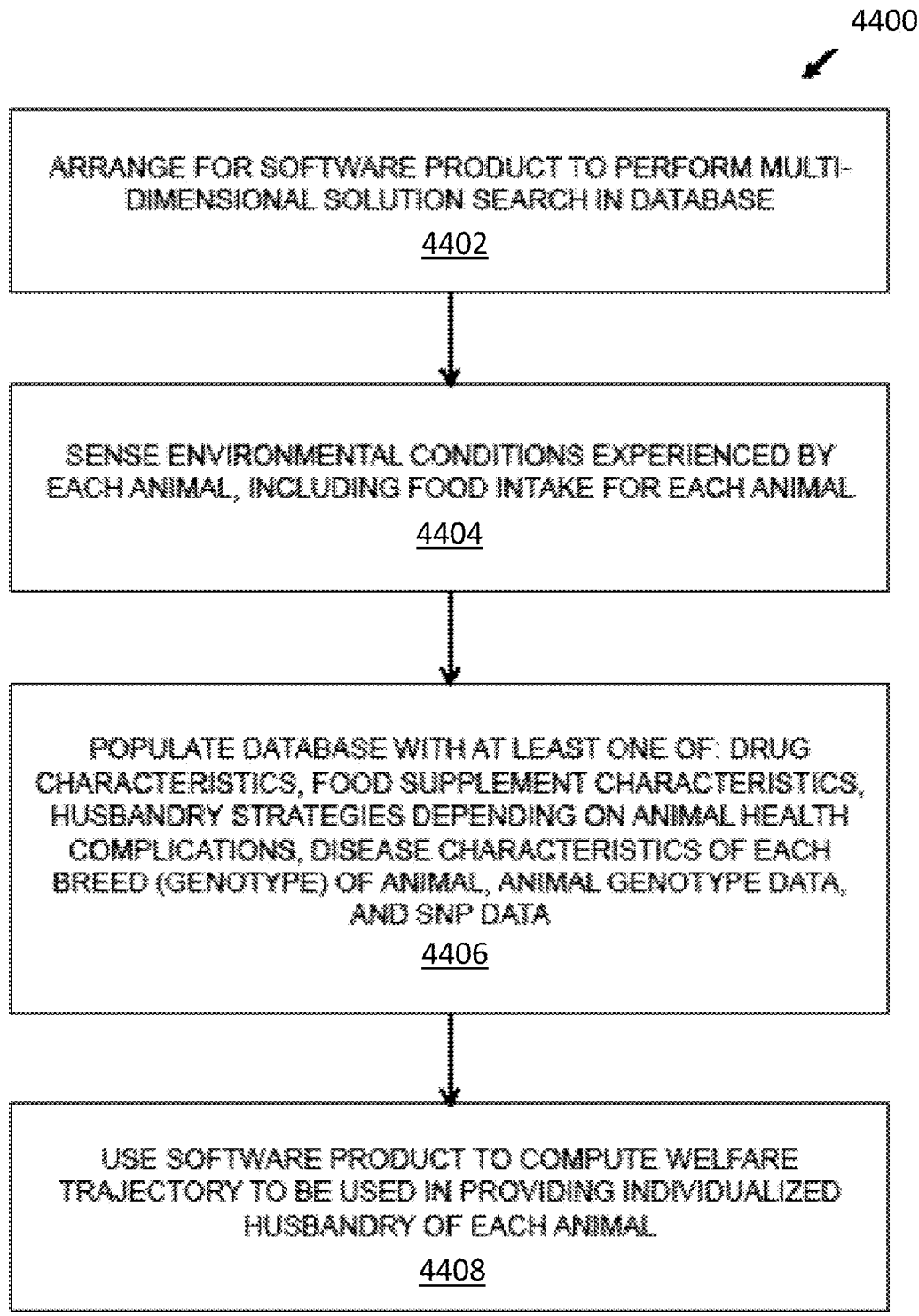
Figure 40:
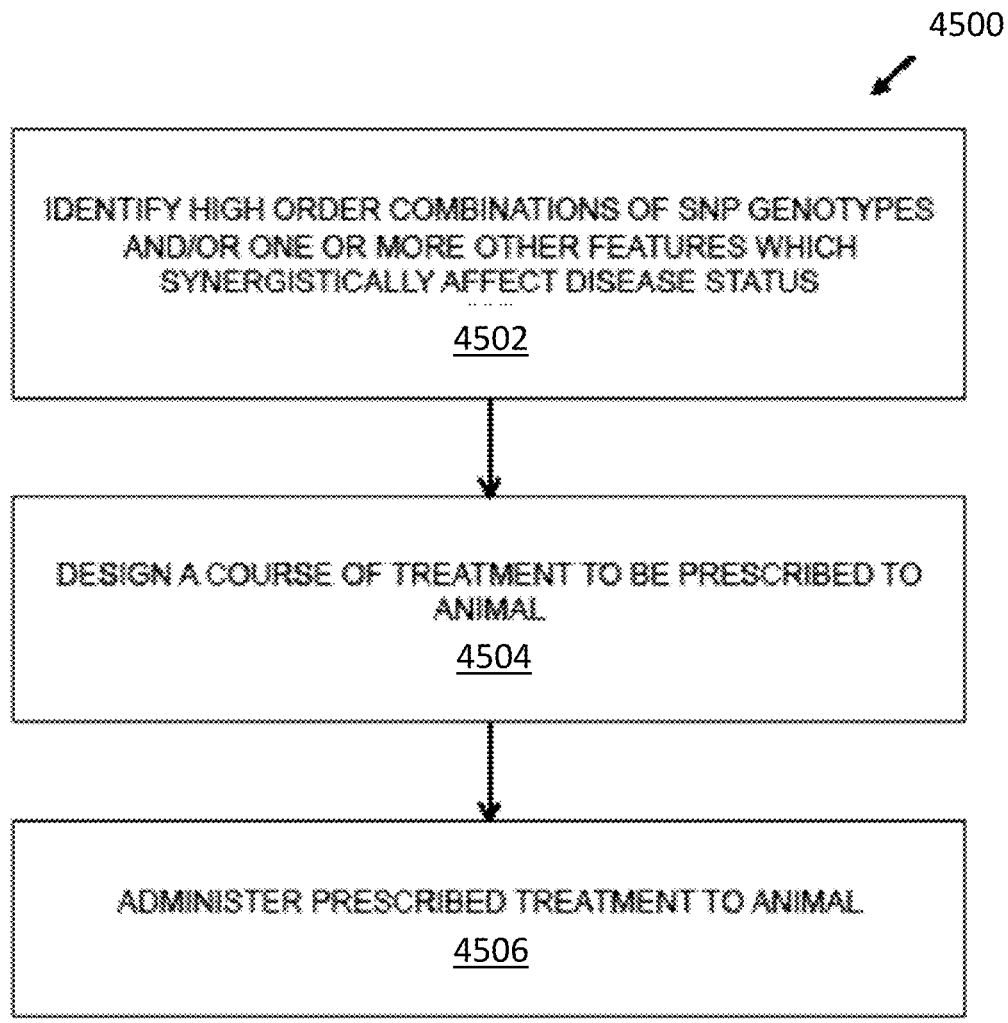
Figure 41:
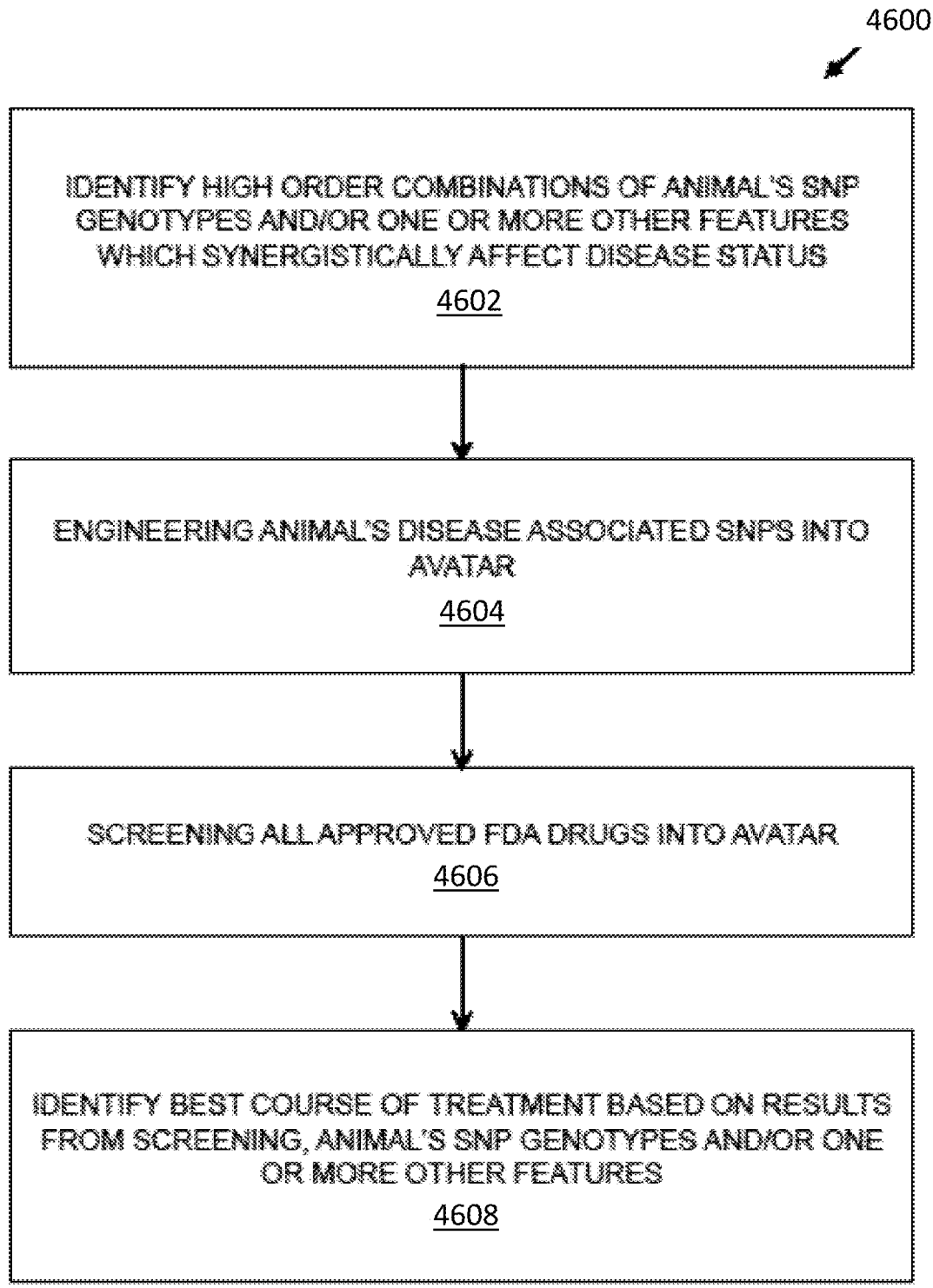
Figure 42:
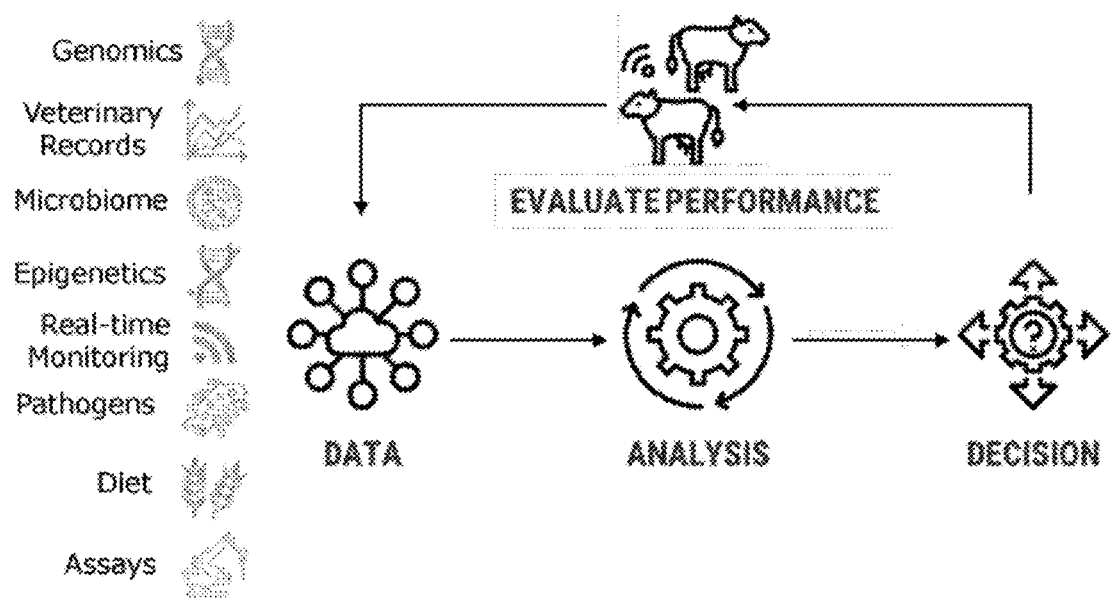
Figure 43:
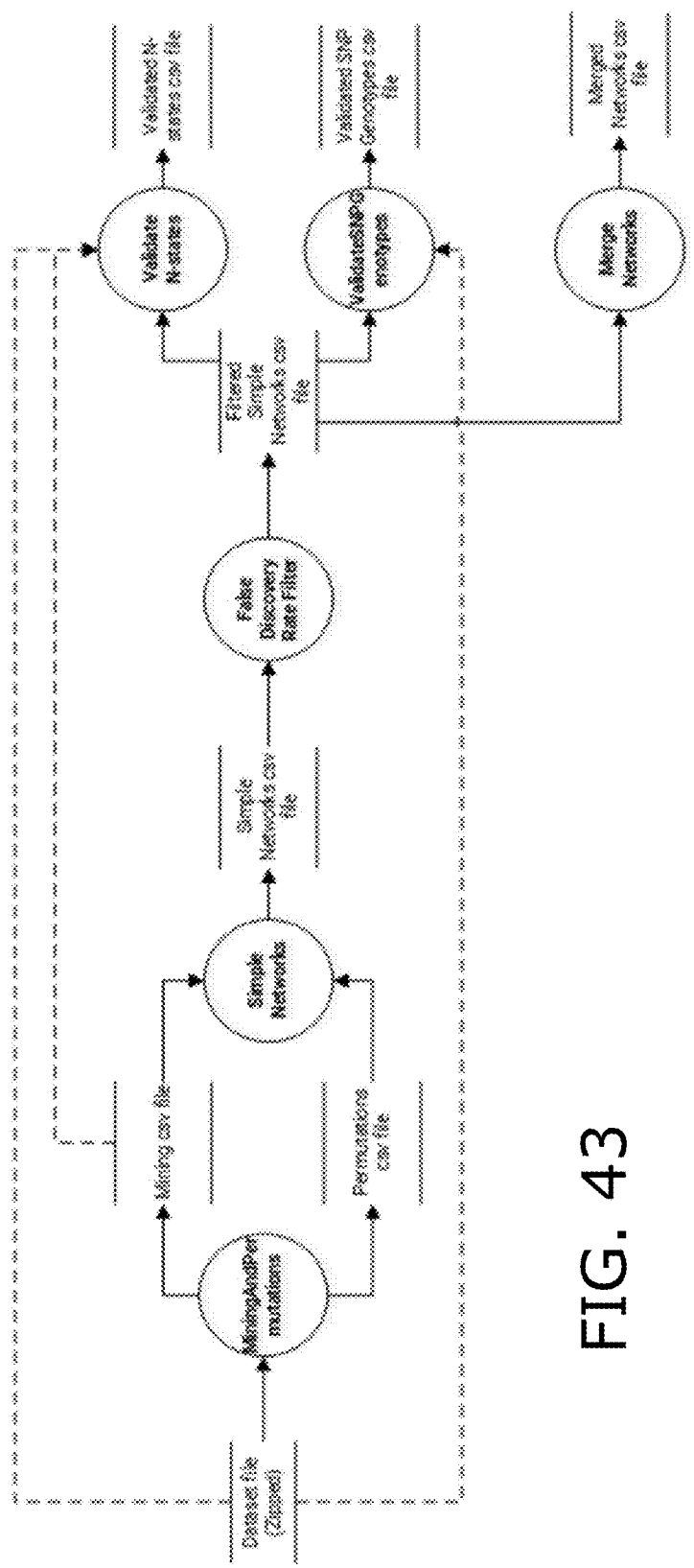
Figure 44:
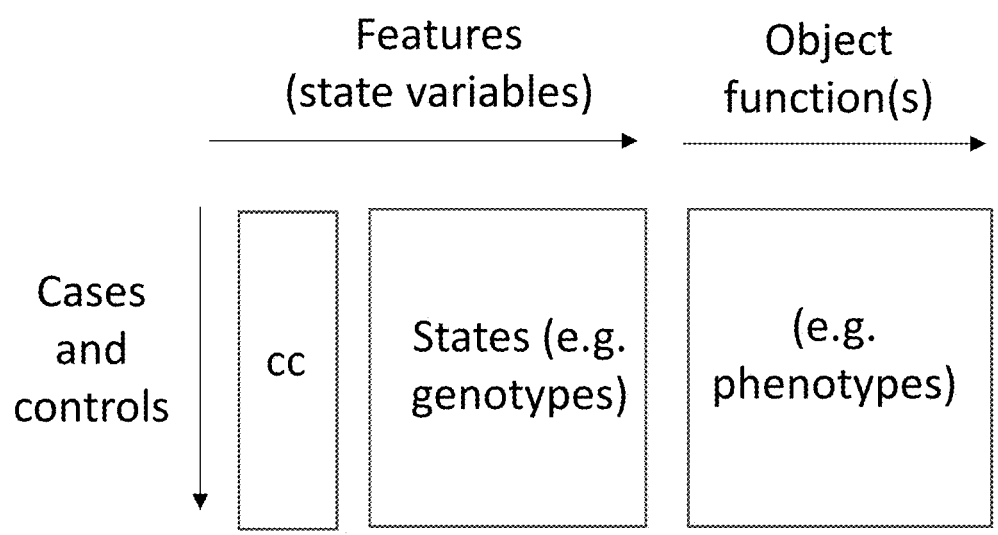
Figure 45:
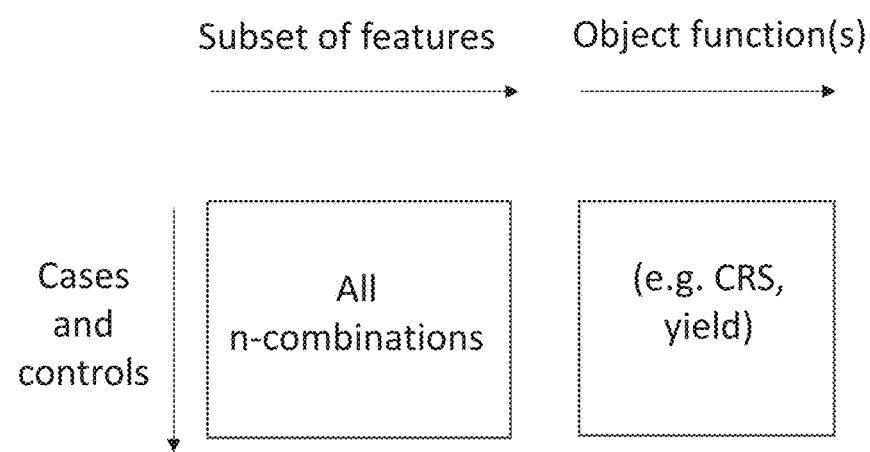
Figure 48:
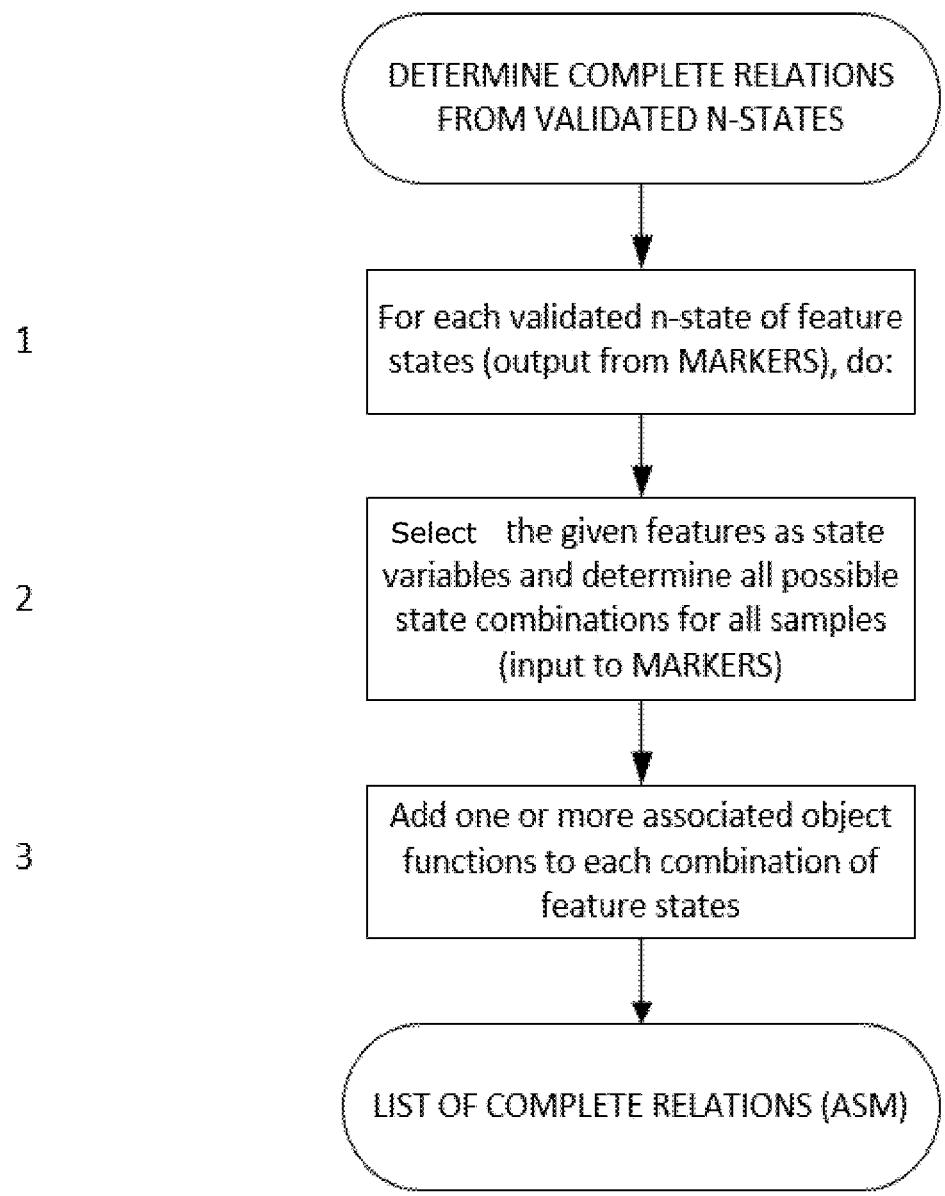

FIG. 6 is an illustration of a step 1 of a colligation method;
FIG. 7 is an illustration of a step 2 of a colligation method;
FIG. 8 is an illustration of a step 3 of a colligation method;
FIG. 9 is an illustration of a step 4 of a colligation method;
FIG. 10 is an illustration of splitting and minimizing a relation in the method of FIG. 2;

FIG. 11 is an illustration of splitting a relation into pairs;
FIG. 12 is an illustration of splitting a relation into a tree structure;
FIG. 13 is an illustration of a splitting model that is employed for performing parallel computing in a step 1;

FIG. 14 is an illustration of a splitting model that is employed for performing parallel computing in a step 2;

FIG. 15 is an illustration of a method of minimizing an array system model when performing runtime applications;

FIG. 16 is an illustration of state propagations that are employed when implementing embodiments of the present disclosure;

FIG. 17 is an illustration of data mining and semantic normalization that is employed when implementing embodiments of the present disclosure;

FIG. 18 is an illustration of a compilation and validation of an Array System Model (ASM);

FIG. 19 is an illustration of a use of an Array System Model: step 1;

FIG. 20 is an illustration of a use of an Array System Model: step 2;

FIG. 21 is an illustration of a use of an Array System Model: step 3;

FIG. 22 is an illustration of a use of an Array System Model: step 4;

FIG. 23 is an illustration of a definition of a given user's input state vector;

FIG. 24 is an illustration of online shopping baskets for use with embodiments of the present disclosure;

FIG. 25 is an illustration of a use of the Array System Model (ASM) for identifying a given example user's risk of encountering interactions with food items;

FIG. 26 is an illustration of a use of an Array System Model to suggest alternative safer food items for a given example user;

FIG. 27 is an illustration of drug warning label information pertinent to embodiments described in the present disclosure;

FIG. 28 is an illustration of a cluster with four distinct states;

FIG. 29 is an illustration of a cluster relation which includes cluster states and variables;

FIG. 30 is an illustration of a clustering application workflow pertaining to precision medicine;

FIG. 31 is an illustration of a cluster relation pertaining to precision medicine;

FIGS. 32A and 32B are an illustration of state-event rules for state-event processing;

FIG. 33 is an illustration of a clustering application workflow pertaining to state-event processing;

FIGS. 34A to 34C are illustrations of steps of processes of colligation employed in embodiments of the present disclosure;

FIGS. 35A to 35F are illustrations of run-time example of array system models employed in embodiments of the present disclosure;

FIG. 36A is an illustration of a solution space depicted as a matrix after compilation of following two relations on Boolean variables A, B, C, D, E, F, G;

FIG. 36B is an illustration of an internal binary representation of the aforesaid relations of FIG. 36A in terms of nested attributes with two elements;

FIG. 36C is an illustration of the internal binary representation of FIG. 36B using such indexed attributes, which is a most effective representation of relations with a large number of redundant nested cells;

FIG. 37 is a schematic illustration of a welfare system that provides welfare support in operation to one or more individuals in an assistive environment (for example, an assistive environment including a plurality of individuals), wherein the welfare system uses the array system model of FIG. 1, in accordance with an embodiment of the present disclosure;

FIG. 38 is a process diagram illustrating steps that are implemented by the welfare system of FIG. 37 for enabling a software product (for example, using the aforesaid PACE computing engine) to perform a multi-dimensional solution search in the decision support knowledge model, in accordance with an embodiment of the present disclosure;

FIG. 39 is an illustration of steps of a method of operating the welfare system of FIG. 37;

FIG. 40 is an illustration of steps of a method of operating the system of FIG. 37, for example when treating an individual in need thereof, in accordance with an embodiment of the present disclosure;

FIG. 41 is an illustration of steps of a method for identifying a course of treatment to be prescribed to a given individual, in accordance with an embodiment of the present disclosure;

FIG. 42 is an illustration of a cycle of continuous welfare to be provided to animals, in accordance with an embodiment of the present disclosure;

FIG. 43 is an illustration of a data flow associated with MARKERS implemented with respect of the Array System Model of FIG. 1 (for example, generated by the aforesaid PACE computing engine pursuant to the present disclosure), wherein an input data file includes all samples (cases and controls) with associated feature states, for example SNP genotypes; an output data file includes a list of validated n-states (and associated networks), wherein each validated n-state (combined with the input data file) is used to build one or more relations of the Array System Model (ASM); in other words, the PACE computing engine generates a PACE model (namely including the ASM) that can, for example, be derived directly from MARKERS without there arising a need to employ colligation;

FIG. 44 is an illustration of contents of the input data file used for MARKERS as well as deriving ASM relations; features, for example SNP's, are considered as state variables and associated corresponding outcomes (namely, phenotypes) as object functions;

FIG. 45 is an illustration of an ASM relation on selected features (defined by a validated n-state) representing all possible n-combinations of the states (for example, genotype combinations); thus, the validated n-state are just one of all combinations, wherein such processing can be considered as a lossless dimensionality reduction on all other features;

FIG. 46 is an illustration of an example ASM relation derived from a potato dataset with associated yield; the aforesaid MARKERS is run to compare high yield (cases) versus low yield (controls), wherein one of the validated n-states is found in layer 8; the state variables of the ASM relation are thus 8 SNPs from the validated n-state, and the relation now contains all possible 8-combinations (including the validated one) defined in an input dataset and an output yield (object function); the ASM relation is susceptible to being used to optimize the outcome, for example by analyzing an impact of changes in genotypes of one or more SNPs in combination;

FIG. 47 is an illustration of an example of an ASM relation derived from a disease study, wherein the study included 607 patients with bipolar disorder and 1355 healthy control; deriving the ASM relation includes using a case-control split to calculate object functions (namely, a sum of cases, a sum of controls and a derived odds ratio); using MARKERS, it feasible to identified a 3-combination with high penetrance (sumCases) and high odds ratio (OR), wherein the ASM relation represents all 3×3×3 genotype combinations of 3 SNPs; similarly, it is feasible to add combinatorial risk scores (CRS) as another object function; each validated n-state will define a unique ASM relation with all combinations defined; an example system for clinical decision support, it is feasible to have a large number of validated n-states, wherein each of which defines a compact ASM relation; an input state vector is a genomic signature of an individual given patient, and an output state vector includes calculated combinatorial risk scores, based on an accumulated contribution from all relations; and FIG. 48 is an illustration of steps of a method for building ASM relations directly from MARKERS; it will be appreciated here that the aforesaid PACE computing engine and its associated compiler are then not needed, since there is no colligation of relations required in the method of FIG. 48.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE DISCLOSURE

In the following description, there are described exemplary embodiments of the present disclosure. Moreover, in operation, the embodiments employ a system model that will be referred to as an "array system model" (ASM). When executing computations in the aforesaid embodiments, all valid solutions are stored in the array system model as one or more nested arrays.

Definitions and explanations relevant to some of the terms used when describing embodiments of the present disclosure are provided in Table 1, as follows:

TABLE 1

| Definitions | Term Definition |
| --- | --- |
| "Constraint resolution" | "Constraint resolution" means establishing substantially all valid combinations of variables satisfying substantially all constraints of a given system. Optionally, all valid combinations of the variables satisfying all the constraints of the given system are established, namely computed, wherein, in an optional case, valid Cartesian sub-spaces of states or combinations satisfy a conjunction of all system constraints for all interconnected variables. |
| "Optimizing" | A term "optimizing" means applying a heuristic selection of combinations within a set of valid combinations. |
| "A system spanned by on finite domains and/or intervals" | A term "a system spanned by variables on finite variables" indicates that each variable domains and/or of a given system consists of a finite set of elements intervals" or state values (for example, logical truth values) or a finite set of intervals. |
| "An addressable solution space" | A term "an addressable solution space" indicates that substantially all valid combinations are explicitly represented; in a preferred case, all valid combinations are explicitly represented. |
| "A Cartesian sub-space" | A term "a Cartesian sub-space" is a compact representation of one or more valid combinations, wherein all combinations are derivable/calculable as a Cartesian product of elements or state values for each variable. |

TABLE 1-continued

| Definitions | Term Definition |
| --- | --- |
| "System constraints" | A term "system constraints" refers to relations (namely propositional functions) for variables defined for a given system. |
| "Interconnecting variables" | A term "interconnecting variables" indicates variables present in at least two relations. |
| "A link variable" | A term "a link variable" means a variable generated by a method according to the present disclosure and added to a given relationship with a unique index, wherein the unique index identifies one corresponding Cartesian sub-space. |
| "Interconnected valid Cartesian sub-spaces" | A term "interconnected valid Cartesian sub-spaces" means valid Cartesian sub-spaces with at least one common variable associated therewith. |
| "External variables" | A term "external variables" means variables that are to be used by or being accessible from an environment during a runtime simulation. |
| "Internal variables" or "interim variables" | A term "internal variables" or "Interim variables" means variables that are not to be used by, or are not to be accessible from, an environment during a runtime simulation. |
| Cluster | A term "cluster" means an accumulation of states, or a list of state vectors associated with known attributes. The state variables are subsets of the domain of the static array system model and/or external variables. |

In overview, embodiments of the present disclosure use (namely, "employ") in operation an array system model (ASM), for example for implementing a control apparatus. Moreover, the embodiments are capable of performing real-time processing; "real-time" means in practice while a user of the embodiments waits for results of computations that are delivered in a predictable time scale, for example in tens of sub-seconds, even when large-scale constraint problems are being computed and resolved by the embodiments. It is thereby feasible, in practice, to provide personalized (context-sensitive) recommendations from hyper-dimensional data feeds in real-time on a wearable, mobile or IoT ("Internet of Things") device. The aforementioned hyper-dimensional data feeds provide hyper-dimensional data that are stored in an array system model, wherein the array system model may represent constraints as well as other types of knowledge associated with each valid combination of the array system model, namely one or more object functions, all of which must interface with an environment in a simple interactive way, via a user interface.

Embodiments of the disclosure, when in operation, support automatic modelling, analysis and real-time inference processing on multi-dimensional system models, such as those described in the present disclosure, on a wide range of computational hardware; such computation hardware includes, for example, signal processing and embedded controllers to mobile devices (for example, smart watches, smartphones and tablets including industrial control interfaces), standard computers (for example, personal computers or laptop computer), graphics processing units (GPUs), distributed computers with parallel processing capabilities, embedded microcontrollers and so forth. Moreover, the embodiments are capable of enabling a wide range of innovative decision support tools, such as clinical decision support systems, to be realized in practice.

Embodiments of the present disclosure, when in operation, employ multidimensional system models, wherein the multi-dimensional system models are, for example, constraint problems expressed in terms of truth tables with MAN combinations, wherein each combination can assume either of a truth-value true (valid) or a truth-value false (invalid). Moreover, the multi-dimensional system models assume N variables are involved, wherein each variable has M elements. In general, each valid combination in a solution space computed in embodiments of the present disclosure may have one or more associated attributes or object functions, for example a price, a pollution impact, a carbon dioxide emission impact, a disease spreading impact (for example, in respect of COVID-19). In a special case of an embodiment of the present disclosure, all combinations may be valid, namely without any constraints on the system model being employed when computing results.

It will be appreciated that computing M<N> combinations using contemporary known computation methods will result in a "combinatorial explosion" in a contemporary computing device, that would result in an unacceptably large memory requirement and long computation time for providing results to users via a user interface; in other words, contemporary known computation methods have an unacceptably high temporal latency. Therefore, contemporarily, it is not a trivial task to solve large constraint problems with a multitude of variables. Nevertheless, embodiments of the present disclosure make it possible to unify seemingly contradictory requirements for completeness (all combinations must be accessible to ensure logical consistency) with compactness of representation and real time inference processing even with complex combinatorial applications on relatively low power computational devices (for example, as aforementioned smart watches, mobile telephones, embedded microcontrollers).

For example, interlocking systems for railway operations are controlled by several thousands of variables representing corresponding signal values or switch positions across an entire rail network. Even a small interlocking system with just 2,000 binary variables will be characterized by a huge number (for example, 2^2000) of states or combinations. Some combinations are valid (namely, they are consistent with the system constraints, for example no two trains should be on the same segment of track in a specific time window), while other combinations are clearly invalid because they would cause accidents or other operational failures. To model such railway systems by employing conventional known technology, it has been necessary to break down the system into sub-systems of sufficiently small size to allow for them to be independently validated. Such an approach is, however, unsatisfactory, because the approach potentially results in both invalid combinations being excluded, as well as a large number of valid combinations, resulting in a less efficient optimization of the system, or even an unreliable representation of the system.

Alternatively, for example, in polypharmaceutical therapeutic regimens, many drug classes (for example, anti-hypertensives, beta-blockers and so forth) contain multiple drugs, which potentially have different or very similar mechanisms of action (for example, diuretics, Calcium channel blockers, ACE inhibitors, and so forth). Within each of these drug classes, there are multiple different (proprietary) drugs (for example, Captopril®, Enalapril®, Fosinopril®, and so forth, wherein such names include registered trademarks), each of which will have different profiles of therapeutic efficacy, drug-drug interactions, drug-disease interactions and drug-food interactions, as well as side-effect risks. There may potentially be hundreds of factors that contribute to a given drug's compatibility for an individual patient, based on their genetic markers, phenotype, comorbidities, co-prescriptions and clinical assay results. As a result, processing such data using multi-dimensional system model results in there being a multidimensional problem space of massive extent (possibly as many as $3.1 \times 10^{18}$ combinations), and unsuited to being computing using conventional known analytical methods. Moreover, it will be appreciated that co-prescription can lead to non-linear results (namely, synergistic effects such as amplification and inhibition across genetic and metabolic networks or pathways) and is not susceptible to being analyzed using merely combinatorial additive logical deduction.

It will be appreciated, in respect of contemporary clinical practice, in a polypharmaceutical therapy situation, that only a sub-set of combinations of various drugs in each given class will be suitable (namely "valid") for a specific given patient, while other combinations of the various drugs will be unsuitable (namely "invalid") for the specific given patient due to the other combinations presenting an unacceptable risk of interaction or side-effect (namely "constraints"). Moreover, it is found in practice that a human clinician is unable to evaluate fully all potentially harmful interactions that might occur for each given patient, especially if the human clinician has only seen the given patient or a consultation of a duration of only a few minutes. There therefore arises a need, that is addressed by embodiments of the present disclosure, for clinical decision support tools to enable the human clinician to select interactively only the valid combinations of drugs from within various classes of medicine, namely avoiding those combinations of drugs that either will not work for the specific given patient or which will pose the specific given patient a potential risk. Thus, embodiments of the present disclosure are susceptible to being configured to provide decision support, but not directly a method of treating the human or animal body.

From the foregoing, it will be appreciated that it is highly desirable to be able to handle constraint problems in complex medical systems in order to provide complete and correct advice/recommendations almost instantaneously, even using software-based support provided from handheld or wearable devices. In general applications, the complex medical systems have associated therewith variables that include multiple data types on finite domains (for example, multi-valued logic, integers, classes or finite sets of intervals), representing, for example, clinical measurements or different diagnoses. For example, data types can include 3-dimensional CT scans, measured cardiac signals, blood analysis results, DNA profiling results and so forth; such data can be considered to be measurands.

Increasingly, in mobile health (namely "mHealth") applications, wearable, smartphone, home-based IoT, visual and even ingestible sensors are providing continuous data feeds for monitoring changing physiological parameters and behaviors of a given individual, with an intention that the data feeds are to be used with other data for providing advanced diagnostic and for monitoring/alerting purposes.

Embodiments of the present disclosure seek to provide practical useful control apparatus, for example compact portable control apparatus including data processing arrangements that are operable to execute software products that are able to provide solutions to medical problems and other types of technical control problems, without resulting in a "combinatorial explosion" that results when multi-dimensional tasks are being addressed. As it will be understood from the following description, embodiments of the present disclosure employ an advantageous form of data representation, in the following termed as an "array system model" (ASM). While the array system model is an optimal tool for complex constraint problems described in the foregoing, it will be appreciated that embodiments of the present disclosure are not limited to addressing medical-related problems; for example, embodiments of the present disclosure can be used in safety critical power stations (for example, nuclear power plant, arrays of wind turbines, arrays of ocean wave energy converters and so forth), for aircraft, for supervising oil well equipment, for chemical plant, for airborne radar systems, for railway network management, for automatic driverless vehicle systems, and similar. Thus, embodiments of the present disclosure concern a method of generating and then applying a system model for interrogating and/or configuring and/or optimizing and/or verifying a logical system spanned by variables on finite domains and/or intervals, wherein the method comprises:

(i) generating and storing, in a memory or a storage medium of a computer and/or distributed on a plurality of computers, an addressable solution space for a set of external variables, wherein the solution space is expressed in terms of all valid sub-spaces (for example, Cartesian sub-spaces) of states or combinations for the set of external variables with interconnected valid sub-spaces (for example, Cartesian sub-spaces) being addressable as valid combinations of indices of link variables and/or core link variables; and (ii) arranging for the solution space to satisfy a conjunction of all, or substantially all, relations of the set of external variables, in order to establish a system model in which all, or substantially all, valid solutions are stored as nested relations.

The nested relations can be used to control physical systems in real time, for example to optimize their operation, to reduce their latency, to reduce waste production, to utilize materials more efficiently, for example to reduce carbon dioxide emissions, to reduce medical complications following treatment (for example, during COVID-19 treatment), and so forth.

Aforementioned embodiments of the present disclosure are capable of performing the computations and real-time inferencing on mobile data processing hardware, thereby offering a further significant data security advantage in applications wherein data security is an operative concern. In digital health applications for example, an aggregation of a large number of patient electronic health records on a central server creates an attractive target for hackers seeking to steal sensitive personal data. By enabling, for embodiments of the present disclosure, such analyses to be performed solely on a given clinician's or patient's own encrypted mobile computing devices, a risk of sophisticated hacking attacks is potentially considerably mitigated. Thus, embodiments of the present disclosure are capable of increasing data security within data processing arrangements.

In embodiments of the present disclosure, there are encountered raw data feeds that are complex and multi-dimensional; such raw data feeds are, for example, derived, at least in part, from sensor arrangements. However, there arises a need to transform such complex and multi-dimensional raw data feeds to useful actionable insight, wherein real-time inferencing is required to be performed and personalized, and wherein there is generated context-specific recommendations or advice. In practice, for embodiments of the present disclosure, there are distinct advantages to being able to compute across such raw data on data collection hardware itself that generates the raw data in operation (for example, a smartwatch, a mobile phone or a remote sensing platform), as such a manner of operation negates requirements for large data transfers that are a potential target of data interception, eavesdropping and hacking; moreover, such large data transfers potentially consume expensive resources in terms of both network bandwidth and power on small, battery powered mobile devices. Embodiments of the present disclosure beneficially use (namely, "employ"), for their variables and constraints, a semantically normalized knowledge graph (namely, a "knowledge graph"), such as, for example, disclosed in United States patent documents U.S. Pat. Nos. 7,493,333 and 7,496,593. Moreover, such knowledge graphs are beneficially used in the embodiments to represent all available information from a variety of public and other data sources about variables, relationships and constraints operating on a given complex system, for example pertaining to an effect of drugs of a specific class on various systems and metabolic pathways in a human or animal body.

Such knowledge graphs are optionally based on a master multi-relational ontology, which includes a plurality of individual assertions, wherein an individual assertion comprises a first concept, a second concept, and a relationship between the first concept and the second concept, wherein at least one concept in a first assertion of the plurality of individual assertions is a concept in at least a second assertion of the plurality of assertions, for example:
  (i) an assertion that 'Fosinopril® is an ACE inhibitor'; and
  (ii) an assertion that 'Fosinopril® is used for the treatment of hypertension'.

For each pair of related concepts, there is beneficially a broad set of descriptive relationships connecting the related concepts, for example expressed in a logical and/or probabilistic as well as linguistic manner. As each concept within each pair is potentially paired (and thus related by multiple descriptive relationships) with other concepts within a given ontology, a complex set of logical connections is formed. A corresponding superset of these connections provides a comprehensive "knowledge graph" describing what is known directly and indirectly about an entirety of concepts within a single domain. The knowledge graph is also optionally used to represent knowledge between and among multiple domains and derived from multiple original sources.

In another beneficial embodiment of the present disclosure, a semantic distance or relatedness of concepts in a specific context is calculated, namely computed, using methods analogous to those described in a published United States patent document U.S. Pat. No. 7,225,183 and in a scientific publication '*Reflective Random Indexing and indirect inference: A scalable method for discovery of implicit connections*', Journal of Biomedical Informatics 43 (2010) pp 240-256. Such probabilistic semantic distance metrics are susceptible to being represented as relationships between two concepts in the semantically normalized knowledge graph and used to determine the degree of connectedness of concepts above, below or between selected thresholds in a context of a specific domain or corpus.

In these aforementioned embodiments of the present disclosure, the specification of a given subset of the knowledge graph to be derived for an array system model optionally includes a selection of two or more concepts or types of concepts from the plurality of assertions of a master multi-relational ontology, applying one or more queries to the two or more concepts or concept types to yield a subset of individual assertions from the plurality of assertions, wherein the queries identify one or more individual assertions from the plurality of individual assertions of the master multi-relational ontology that connect, directly or indirectly, the two or more concepts. In a context of complex domains such as healthcare examples described in the foregoing, such derived knowledge graphs potentially contain millions of concepts, each of which has multiple properties (namely, variables) with multiple potential values, and each of which may have up to tens of thousands of direct or derived logical constraints.

In describing embodiments of the present disclosure, a term "logical system" is used to mean a complete system, alternatively a sub-system that is a part of a larger system. When used to refer to a sub-system, variables associated with other sub-systems are treated as being "external variables".

In embodiments of the present disclosure, for example implemented as a control apparatus employing data processing hardware for receiving sensor signals obtained from a given system and for generating corresponding outputs for controlling the system, all invalid states or combinations violating constraints of the given system are excluded from relations that are employed in operation. Such exclusion of invalid states or combinations is beneficially performed when an array system model (ASM) is generated by a method pursuant to the present disclosure; in other words, in embodiments of the present disclosure, the invalid states or combinations are excluded from computations whenever identified to enable more rapid computation of useful results to be achieved. In practice, a state of contradiction or inconsistency is present in a system if just one relation of the system has no valid combination or state. Conversely, a system is regarded as being consistent if at least one state or combination of states is valid; namely, one state or a combination of states satisfies all system constraints. If, when generating a given system model, just one relation of a system is found to have no valid combination or state, then that whole system is in a state of contradiction or inconsistency and is excluded for achieving enhanced computational efficiency.

In the following, a process of colligating relations (that is, combining relations to arrive at a more complex sub-system or system) is elucidated in detail. It will be appreciated that, on each level of a process of colligation, inconsistencies or contradictions are identified in embodiments of the present disclosure, and will, thus, result in exclusion of the colligated sub-system or system. Thus, when a generating process has been completed in embodiments of the present disclosure, the system will be consistent, as manifested by all relations having at least one valid Cartesian sub-space.

In the present disclosure, a term "system" is used to refer to an entire system of variables or, alternatively, to a part of an entire system of variables, for example as aforementioned. With reference to a specific application (for example healthcare), a system provides a representation of a complete set of available domain knowledge upon which real-time reasoning or inferencing can be performed using embodiments of the present disclosure to provide useful, actionable controls, insights and recommendations using decision support tools incorporating an array system model (for example, for selecting a best available therapy for a specific patient at a point of care; for example, for selecting a best available selection of replacement component parts to be used when repairing an item of machinery). There is thereby provided an interaction between an array system model (ASM) and an environment that is carried out by a state vector representing states of all variables involved, including physical measurements as well as decision parameters. Thus, in example embodiments of the present disclosure, variables involved can include sensor signals acquired using physical sensors, and decision parameters can be outputs that are used to control operating states of various apparatus, for example in a hospital, in an industrial plant, in a vehicle, in an energy power plant, and so forth. In embodiments of the present disclosure, a given system is completely defined in that every combination under the system is either valid or invalid with respect to all system constraints relevant to the use of the system model and preferably with respect to absolutely all system constraints. Thus, the term "system", used about an entire system of variables, indicates that the entire system is completely defined with respect to all system constraints relevant to the use of the array system model, and optionally with respect to absolutely all system constraints. When a system of variables is not completely defined in the above sense of this term, then only that part of the system which is in fact completely defined is covered by the term "system" pursuant to the present disclosure. The term "substantially" indicates a system in which the process of colligation has not been completed, and where the runtime environment must be adapted to perform certain tests for consistency; for example, "substantially all" refers to at least 90%, more optionally at least 95%, and most optionally at least 99%. As aforementioned, the system constraints are optionally determined by conjugating one or more relations, wherein each relation represents valid Cartesian sub-spaces of states or combinations on a given subset of variables. The conjugation of the one or more relations comprises calculating Cartesian sub-spaces satisfying the combined constraints of the one or more relations. If no relations have common variables, no further action is required to conjugate the relations in embodiments of the present disclosure.

According to an important optional feature of the invention, all relations with at least one common variable are colligated. The colligation comprises conjugating the constraints of two or more relations that are connected by having common variables therebetween to establish one or more Cartesian sub-spaces satisfying the combined constraints of the two or more relations. In embodiments of the present disclosure, the colligation of two or more relations will normally be performed by joining the two or more relations up to a predetermined limit. Such joining comprises an operation of replacing a set of relations with a single relation satisfying combined constraints of the set.

The set of relations is not limited to two relations, but can in general be any finite number of relations. In an example embodiment of the present disclosure, a case where three or more relations are joined is typically decomposed into a number of pairwise joins; this pairwise joining optionally comprises a predetermined strategy or this pairwise joining is optionally in a random order. Moreover, the joining process will typically reduce the number of relations, and the result will be one or more relations with common link variables. Moreover, the linking of the relations consists of adding link variables and adding one or more calculated relations representing the constraints on the link variables.

In an example embodiment of the present disclosure, any relation with non-connecting as well as connecting variables is extended by adding a unique link variable with a unique index identifying each valid Cartesian sub-space on either the non-connecting or connecting variables. In such situations, it is often advantageous to split a given relation into two relations, wherein one relation pertains to the non-connecting variables and the link variable, and the other relation pertains to the connecting variables and the link variable.

In relation to embodiments of the present disclosure, a term "completeness of deduction" indicates that all logical consequences are required to be deduced for one or more variables. Moreover, in example embodiments of the present disclosure, the completeness of deduction relates to all logical consequences on all variables, but as indicated above, the embodiments of the present disclosure are not limited to computing all logical consequences.

When the colligation process is completed, the relations for isolated variables are optionally split into a plurality of smaller interconnected relations with the isolated variables in expanded form (namely tuples). Such a representation is potentially more compact than compressed Cartesian arguments, and will make it possible to associate object functions to each single combination of the defining variables. When the array system model is to be used for optimization or learning, one or more object functions, for example pricing functions, are optionally incorporated into the array system model (ASM). An object function of a given subset of variables, wherein the object function derives characteristics of a given subset of variables, and is linked to a complete solution space by deducing constraints imposed by the object function on each link variable connected to the given subset of variables. After the array system model has been generated by a method pursuant to the present disclosure, object functions can provide information between a set of variables and a set of object function values, for example cost, price, risk or weight. As an example in healthcare, given a patient's set of co-morbidities and co-prescriptions, it is potentially contemporarily not possible to select a drug for a particular disease from any of available options that does not present some significant risk of interactions or side-effects arising. In such a case, it is necessary to choose a best available drug, which reduces, for example minimizes, a likelihood and/or severity of any of these potential interactions or side-effects. Such a reduction, for example minimization, can be achieved by accepting a partially incomplete deduction (with, for example, a single invalid variable), and then using object functions as described below to evaluate and optimize the likely outcomes, such as potential patient benefit, treatment cost and side-effect risk.

If a set of object function values does not have a "natural" order, in contrast, for example with numbers, an arbitrary order can be assigned to the set of object function values.

Characteristics of the object function are susceptible to being determined; moreover, constraints on the link variables deduced on each combination of the given variables can be determined, wherein the result is represented as a relation on the object function, the given variables, and the link variables. These characteristics are optionally values of the object function given by functional mapping of a set of independent variables or a set of constrained variables. The mapping can also be a general relation yielding one or more object function values for each combination of the variables.

Embodiments of the present disclosure provide a method for (namely, method of) interrogating and/or configuring and/or optimizing and/or verifying and/or controlling a system spanned by variables on finite domains, wherein the method comprises:

(i) providing an array system model in which substantially all valid solutions in the system are stored as nested arrays representing valid Cartesian sub-spaces on all external variables, with all interconnected valid Cartesian sub-spaces being addressable as valid combinations of indices of link variables; and (ii) deducing any sub-space, corresponding to an input statement and/or query, of states or combinations spanned by one or more variables of the system represented by the nested arrays by deriving the consequences of a statement and/or a query by applying the constraints defined by the statement and/or query to the system model.

In respect of embodiments of the disclosure, "deducing" means deriving or determining logical inferences or conclusions, for example all inferences or conclusions, from a given set of premises, namely all the system constraints.

In respect of embodiments of the disclosure, a "query" means a question for which an array system model is operable to provide answers, for example all answers; such a "query" is, for example, a question regarding a particular combination of sensor signal values, but not limited thereto, subject to defined conditions. An example question concerns one or more valid combinations of a given set of variables satisfying the system constraints and, optionally, also satisfying an external statement; an external statement concerns, for example, which antihypertensive medication can be given safely to a specific patient who already has a given set of co-morbidities and co-prescriptions. An external statement can be a number of asserted and/or measured states and/or constraints from the environment. Moreover, a deduction of any sub-space of states or combinations is performed on a given subset of one or more variables either without or colligated with asserted and/or measured states and/or constraints from the environment. An interaction between the system represented by the array system model and the environment is suitably performed by means of a state vector (SV) representing all valid states or values of each variable.

Thus, an input state vector (SV1) is employed to represent the asserted and/or measured states from the environment, such as for example, the set of a patient's co-morbidities and co-prescriptions as described in the foregoing, or a set of clinical parameters measured in real-time by sensors of a wearable device, whereas an output state vector (SV2) is used to represented one or more deduced consequences on each variable of the entire system when the constraints of SV1 are colligated with all system constraints in the array system model, such as, for example, whether a potential new medication is valid or invalid for a given patient.

In a preferred embodiment of the present disclosure, each invalid variable is either discarded from the environment (i.e. in relation to SV1) or deduced as a consequence (i.e. in relation to SV2). Furthermore, optionally, variables defined as output variables are allowed to change a state without causing a contradiction. Moreover, a deduction is optionally performed by consulting one or more relations and/or one or more object functions at a time by colligating a given subset of variables in a relation with given subsets of states in a state vector and then there is deduced therefrom possible states of each variable.

In embodiments of the present disclosure, clustering and dynamic properties are employed in operation of the array system model. Such clusters represent a list of state vectors associated with known attributes. States of the cluster are determined from external variables (EV) and/or internal state variables that span the array system model (ASM). Relationships between the states of the clusters and state variables are defined by a cluster relation. For example, a given cluster relation has three state variables: a state of the cluster, and variables V1 and V2. In operation of embodiments of the present disclosure, there will be a logical OR between rows in a relation table (namely, as in a disjunctive form). Alternatively, a cluster relation is a relation, wherein states of clusters are input and state variables are output. The cluster relations reduce a hyper-dimensional space, having millions of parameters, to a corresponding multi-dimensional array system model. When the states of the external variables are known, processing of the cluster relation in run time may be described as including steps as follows:

(i) comparing external measurements with the states of cluster in the cluster relation and identify corresponding matching rows;
(ii) deducing values of the output state variables V1 and V2; and
(iii) deducing the constraints on all other state variables by a state propagation in the array system model.

Completeness without colligation can be ensured as the given cluster may be only a part of one relation and therefore considered as an isolated variable in the multi-dimensional and complete array system model. Exemplary applications of clustering include, precision medicine, state-event processing and many other exceptionally complex applications.

Precision medicine is an example of a decision support system. In such precision medicine, clusters associated with disorders and treatments are based upon combinations of genomic, phenotypic and clinical data. For illustration purposes, genotypes (with the values 0, 1, 2) of 500,000 single-nucleotide polymorphism (SNPs) for a given patient are measured. The cluster relation based on combinations of four SNP genotypes is depicted in FIG. 31. In FIG. 31, there is provided an illustration wherein an associated state variable S is Boolean and is a simplest representation of a link between a cluster relation and corresponding internal states. If the patient matches any of the internal states, the value of S is evaluated as being true. If the patient matches a specific cluster, then one dimension in the array system model is evaluated. In a case of more dimensions, genomic clustering may be used to deduce specific medication or therapy for a given patient. Another exemplary application of clustering is in state-event processing. State-event processing specifies a change from one state to another, wherein a change of state is based on external events. In FIGS. 32A-32B, there are illustrated state-event rules for state event processing. Notably, in FIG. 32A, there are illustrated two state-event rules that describe actions upon occurrence of an event, for example, such as pressing a button "PLAY". As shown, there are two current cluster states CS1 and CS2 that are distinct to ensure unambiguous interpretation of the event "PLAY". Furthermore, cluster relations within the given cluster states CS1 and CS2 are used to describe state-event rules pertaining thereto. Therefore, based upon such state-event rules associated with the two current cluster states CS1 and CS2, there are described valid state transitions from the current state CS1 to a new state NS1, and from the current state CS2 to a new state NS2, upon occurrence of the event "PLAY". As shown, upon state transition from the current state CS1 to the new state NS1, the action of displaying XXX is implemented whereas upon state transition from the current state CS2 to the new state NS2, the action of displaying YYY is implemented. In FIG. 32B, there is illustrated a detailed state-event model comprising state-event rules pertaining to an exemplary cluster having two cluster states (for example, such as the cluster states CS1 and NS1 of FIG. 32A) with respect to the aforesaid event (namely, pressing the button "PLAY"). As shown, based upon the state-event rules (of FIG. 32A) pertaining to the given cluster, the four state vectors of the given cluster transition from their current state (for example, the state CS1) to a new state (for example, the state NS1). Furthermore, for example, a state vector of the given cluster that comprises five state variables, transitions from its current state (having the five state variables) to a new state having two state variables, as illustrated in the top row of the given exemplary cluster of FIG. 32B. In FIG. 33, there is illustrated an implementation of a cluster relation on a new state vector (SV1) and accordingly of obtain an output state vector (SV2). There are static constraints, and a constraint engine (colligation and deduction) is utilized for obtaining the output state vector SV2. The output of the cluster relations and variables are input to a new state vector (SV1). When static constraints are implemented on such a new state SV1, the output state vector (SV2) is obtained. The output state vector SV2 represents a single state, and can be determined by one or more state deductions in order to find the best state transition.

A consultation of a relation is beneficially performed by colligating, for example joining, the relation and states of variables present in the relation. The consultation provides a result that can be a projection (namely, a union of all elements) on each variable of the colligated relation, or the result can be the colligated relation. The colligation is optionally a joining, but it will be appreciated that the consultation of each relation is not limited thereto. In an example embodiment of the present disclosure, two or more variables are colligated in parallel; projections on two or more variables are similarly performed in parallel. However, it will be appreciated that embodiments of the present disclosure are not limited to such parallel implementation, and the embodiments are optionally susceptible to being implemented sequentially. In an example embodiment of the present disclosure, a completeness of deduction is obtained by consulting connected relations, until no further consequences can be deduced on any link variable. Such an operation is termed "state propagation". Moreover, such a state propagation comprises consulting two or more relations in parallel, namely concurrently. The parallel execution of the state propagation can be implemented in one or more GPUs (Graphics Processing Units) or hardware designed for such parallel execution. The interaction between the array system model and the environment by the state vector can be carried out by simple operations that are suitable for a hardware implementation on devices such as embedded control systems, Internet of Things (IoT) sensors or Field Programmable Gate Arrays (FPGAs).

An important feature of configurations and/or optimizations employed in embodiments of the present disclosure is that states of contradiction can be identified, namely when no valid states or values are deduced when consulting, namely investigating or checking, at least one relation. Such identification of contradictions and an elimination of a need to perform computations in connection with the contradictions, enable methods of the present disclosure to reduce computational resources required for performing complex hyper-dimensional computations. In the following, a more detailed description of a manner of operation of embodiments of the present disclosure will be described.

The array system model (referred to as ASM in the following) is a compact and complete representation of all valid combinations and associated object functions of constraint problems on finite domains or intervals. The ASM is used to represent a person, an apparatus, a facility, a factory or similar system. A solution space of valid states or combinations is beneficially represented geometrically in terms of nested data arrays, and the ASM is simulated very efficiently in operation by simple operations on these arrays using CPUs (central processing units), GPUs (graphics processing units) or hardware devices designed for this specific use.

Major data flows required for performing ASM modelling are summarized in FIG. 1. The major data flows include input data, for example a user-defined specification of system constraints in terms of a set of rules or relations pertaining to a given set of variables. Thus, the ASM modelling is implemented in a four-step procedure as shown in FIG. 1, wherein the six-step procedure includes STEP1 to STEP6 as follows:

Step 1: Compile Variables and Relations

Each user-defined variable and each relation is compiled into the internal array representation. At this stage STEP 1, the relations are considered as independent items.

Step 2: Colligate Relations, Verification of System

The solution space of the entire system is determined by colligating interconnected relations (constraint elimination). The system is simultaneously tested for logical consistency and redundancy. Embodiments of the present disclosure relate inter alia to a more efficient colligation strategy.

Step 3: Minimize and Link Complete Solution Space

The complete solution space can be, for example, minimized and restructured in order to meet requirements in a runtime environment. Examples include:
  (i) minimizing memory footprint to enable operation on a wearable device;
  (ii) splitting the array system model into multiple instances for implementation on parallel processing hardware;
  (iii) adding object functions on combinations of selected variables; and
  (iv) adding dynamic constraints in terms of relations as well as states to enable real-time response to signals from IoT or wearable sensors.

Step 4: Link Object Functions

Optionally, the relations may be extended with further attributes, when the valid combinations satisfying the system constraints are associated with values or object functions to be optimized or used for specific applications, such as, for example, a price or "soft constraints" such as side-effect risk and severity with further values than just true or false.

Step 5: Cluster States and Cluster Relations

Optionally, clustering is performed to reduce the hyper-dimensional space, potentially with millions of parameters, to the multi-dimensional ASM for performing decision support. Examples include: millions of genomic phenotypic and clinical variables that are condensed/reduced to a few hundred variables, which is utilized by decision support system. Clustering is based on cluster states (i.e. "states of clusters") and cluster relations.

Step 6: State-Event Relations

Optionally, state-event relations utilize external events to describe the change from one state to another. Clustering is based upon internal state variables representing the conditions for change of state.

At this stage, the process of ASM modelling is finished. The entire solution space is now susceptible to being addressed by coordinate indexing and other simple operations on the nested arrays.

Figure 2:
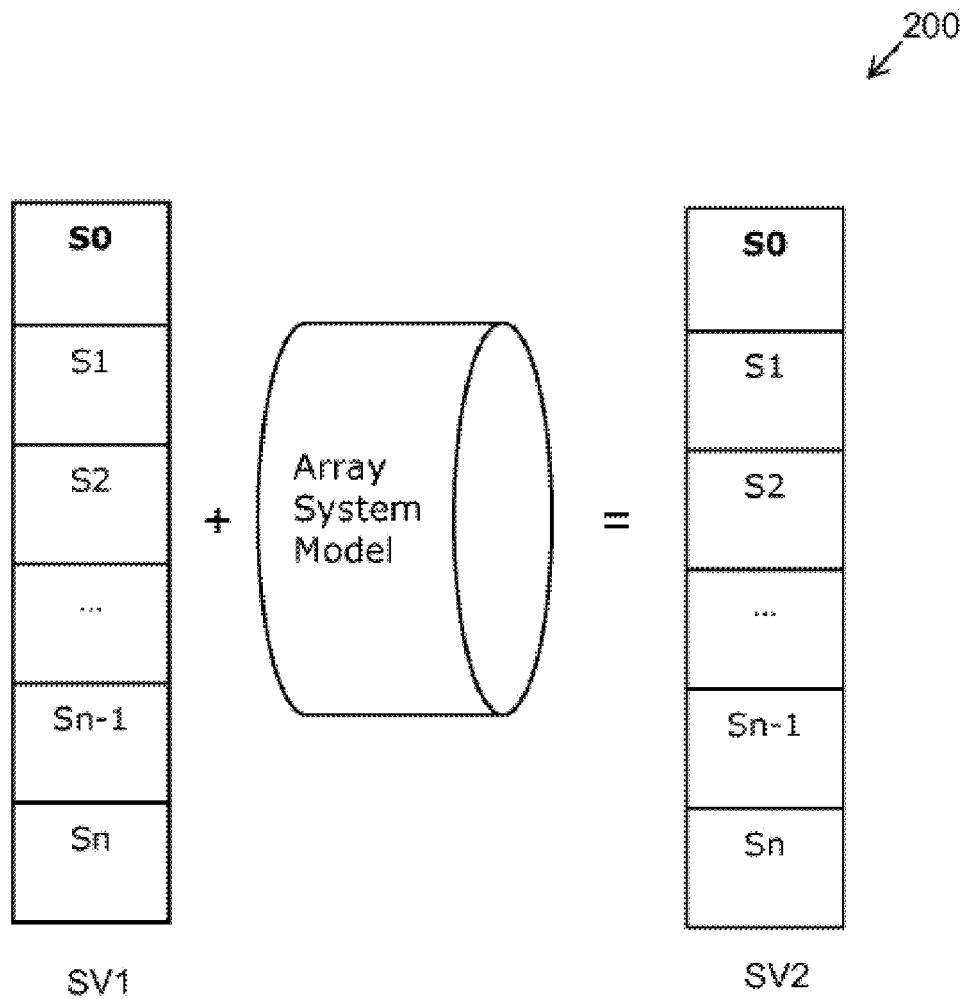
FIG. 2 is an illustration of a method of using the array system model of FIG. 1, by employing a process of state deduction.

A run-time application of the ASM is shown in FIG. 2. Each item of a state vector SV represents the state (namely the valid values) of an associated variable. For example, in respect of the input state vector SV1, one or more variables are bounded due to external measurements or assertions. Moreover, the input state vector SV2 represents the resulting constraints on all variables. The properties of the ASM are summarized as follows:
  (i) a run-time execution on the ASM is performed with completeness of deduction in real-time, namely with predictable use of processing time and memory. The ASM technology is therefore suitable for use in embedded decision support or for use in control systems on small computer devices; and (ii) the ASM representation is compact and complete. Embedded applications of embodiments of the present disclosure are required to fulfil all requirements for compactness, completeness and real-time capability with limited computing resources, even on large system models.

Simple Colligation Strategy (ADB)

Optionally, a generation of the ASM technology (to be abbreviated to "ADB" in the following) is based on a simple colligation strategy by pairwise joins of relations and then linking isolated variables whenever possible.

To illustrate a simple colligation strategy, there is considered a very simple constraint example with six Boolean variables (A, B, C, D, E, F) and five relations (RO, R1, R2, R3, R4):

RO: $(A \lor B) \Rightarrow (C \lor D)$

R1: $C \Rightarrow E$

R2: $D \Rightarrow E$

R3: not (A and B and C)

R4: not (E=F)

It will be appreciated from the foregoing, that the relations are operable to share variables. Moreover, the colligation graph (see FIG. 3) is an illustration of a structure of interconnected relations, wherein nodes represent relations and arcs represent common variables of two of the relations.

A first colligation step is to compile each relation, namely to determine valid combinations of each relation:

| RO: | | | |
|---|---|---|---|
| A | B | C | D |
| 0 | 0 | 0 | 0 |
| 0 1 | 0 1 | 0 1 | 1 |
| 0 1 | 0 1 | 1 | 0 |

| R1: | |
|---|---|
| C | E |
| 0 | 0 1 |
| 1 | 1 |

| R2: | |
|---|---|
| D | E |
| 0 | 0 1 |
| 1 | 1 |

| R3: | | |
|---|---|---|
| A | B | C |
| 0 1 | 0 1 | 0 |
| 0 1 | 0 | 1 |
| 0 | 1 | 1 |

| R4: | |
|---|---|
| E | F |
| 0 | 1 |
| 1 | 0 |

It will be appreciated that all invalid combinations are eliminated from each relation. Moreover, the valid combinations are expressed in terms of Cartesian sub-spaces; however, it will be appreciated that other coordinate spatial reference frames can be optionally employed for implementing embodiments of the present disclosure. For example, the relation RO counts three Cartesian sub-spaces representing 13 valid combinations, while the three invalid combinations are eliminated. There is a logical AND between the variables in each row, and a logical OR between the rows (disjunctive normal form). Thus, the first row is (not A) and (not B) and (not C) and (not D), and the logical interpretation of the entire table is: ((not A) and (not B) and (not C) and (not D)) OR (D) OR (C and (not D))

A second colligation step is to colligate the relations to determine the solution space of the conjunction of all relations. In this small example, it is possible to join all relations into a single relation with 12 valid combinations, as follows:

| A | B | C | D | E | F |
|---|---|---|---|---|---|
| 0 | 0 | 0 | 0 | 0 | 1 |
| 0 | 0 | 0 | 0 | 1 | 0 |
| 0 1 | 0 1 | 0 | 1 | 1 | 0 |
| 0 1 | 0 | 1 | 0 1 | 1 | 0 |
| 0 | 1 | 1 | 0 1 | 1 | 0 |

Since all user-defined variables (A, B, F) are isolated in a single relation, the colligation process is thereby completed. However, it will be appreciated that this is a special case of an array system model with just a single relation. It is now possible to perform inference processing by performing simple array operations. For example, the derived relation (D, F) is deduced by a simple projection eliminating the other variables, all of which are considered interim variables:

| D | F |
|---|---|
| 0 | 1 |
| 0 | 0 |
| 1 | 0 |

This relation can be compressed into a more compact array representation with just two Cartesian sub-spaces:

| D | F |
|---|---|
| 0 | 0 1 |
| 1 | 0 |

This derived relation is the truth-table of the propositional function not (D and F). Thus, it is thereby concluded that D and F are never permitted at the same time.

The state vector is the important link between the compiled (colligated) array system model and the environment.

For example, assuming that a following state vector pertains, representing "A is true; the other variables are unknown":

| A | B   | C   | D   | E   | F   |
|---|-----|-----|-----|-----|-----|
| 1 | 0 1 | 0 1 | 0 1 | 0 1 | 0 1 |

The output state vector is deduced by consulting the complete solution space, in this case represented by a single relation. Since A is bound to true (value 1), three Cartesian sub-spaces are now invalid (marked in bold and underlined text), while two arguments are valid:

| A | B   | C   | D   | E | F |
|---|-----|-----|-----|---|---|
| 0 | 0   | 0   | 0   | 0 | 1 |
| *0* | *0* | *0* | *0* | *1* | *0* |
| *1* | *0 1* | *0* | *1* | *1* | *0* |
| 1 | 0   | 1   | 0 1 | 1 | 0 |
| *0* | *1* | *1* | *0 1* | *1* | *0* |

The state of each variable is deduced by computing the union of elements from the two valid Cartesian sub-spaces (shown as bold and underlined text):

| A | B   | C   | D   | E | F |
|---|-----|-----|-----|---|---|
| 1 | 0 1 | 0 1 | 0 1 | *1* | *0* |

Assuming the Boolean variable A=1, it is thereby concluded that the Boolean variable E=1 and F=0, whereas the Boolean variable B, C, D=0 or 1 (namely, a tautology). In general, the colligation process is carried out by pairwise joins of the relations, and after each join isolated variables are separated (assuming at least two isolated variables) into new relations connected by common link variables representing the valid Cartesian sub-spaces. Thus, on the current example the colligation process can be executed by the following steps:

Step 1: Join Relations R0 and R3 and Isolate Variables:
Joining the relations R0 and R3 yields the following relation:

| A   | B   | C | D   |
|-----|-----|---|-----|
| 0   | 0   | 0 | 0   |
| 0 1 | 0 1 | 0 | 1   |
| 0 1 | 0   | 1 | 0 1 |
| 0   | 1   | 1 | 0 1 |

On account of the variables A and B now being isolated, it is feasible to split the (A, B, C, D)-relation into the (A, B)-relation (to be stored for the final output) and the (C, D)-relation linked by a common link variable (Link0) representing the indices of the Cartesian subspaces of the (A, B)-relation yet to be colligated:

| C   | D   | Link0 |
|-----|-----|-------|
| 0   | 0   | 0     |
| 0 1 | 0 1 | 1     |
| 0 1 | 0   | 2     |
| 0   | 1   | 3     |

| C | D   | Link0 |
|---|-----|-------|
| 0 | 0   | 0     |
| 0 | 1   | 1     |
| 1 | 0 1 | 2 3   |

Step 2: Join Relations R1 and R2:
The joined result is the following (C, D, E)-relation:

| C   | D   | E |
|-----|-----|---|
| 0   | 0   | 0 |
| 0 1 | 0 1 | 1 |

In this case, no variables are isolated and all variables are then kept for a next join.

Step 3: Join relations (C, D, Link0) and (C, D, E) and then isolate variables (C, D, Link0):
These two relations are determined, namely computed, in the previous steps 1 and 2 above, and their corresponding joined result is:

| C | D   | E   | Link0 |
|---|-----|-----|-------|
| 0 | 0   | 0 1 | 0     |
| 0 | 1   | 1   | 1     |
| 1 | 0 1 | 1   | 2 3   |

On account of the variables C, D and Link0 are now isolated, there is then employed a step of splitting the relation using new link variable Link1:

| E   | Link1 |
|-----|-------|
| 0 1 | 0     |
| 1   | 1 2   |

Step 4: Join Relations R4 and (E, Link1):
A final join yields a relation (E, F, Link1). Thus, summing up, a complete corresponding solution space is represented by three following relations:

| A   | B   | Link0 |
|-----|-----|-------|
| 0   | 0   | 0     |
| 0 1 | 0 1 | 1     |
| 0 1 | 0   | 2     |
| 0   | 1   | 3     |

| C | D   | Link0 | Link1 |
|---|-----|-------|-------|
| 0 | 0   | 0     | 0     |
| 0 | 1   | 1     | 1     |
| 1 | 0 1 | 2 3   | 2     |

| E | F | Link1 |
|---|---|-------|
| 0 | 1 | 0     |
| 1 | 0 | 0 1 2 |

| C | D | Link0 | Link1 |
|---|---|-------|-------|
| 0 | 0 | 0     | 0     |
| 0 | 1 | 1     | 1     |
| 1 | 0 1 | 2 3 | 2     |

This is an array system model with three interconnected relations; the colligation graph in FIG. 13 is relevant to this array system model.

The state vector is deduced by consulting one relation at a time, until no further constraints are added to each variable (state propagation). For example, assuming "A is true", the relation (A, B, Link0) yields a following output state vector:

| A | B | Link0 |
|---|---|-------|
| 1 | 0 1 | *1 2* |

Since the link variable Link0 is now constrained (elements 0 and 3 are invalid and thus eliminated from Link0), the relation (C, D, Link0, Link1) is consulted yielding a following output state vector:

| C | D | Link0 | Link1 |
|---|---|-------|-------|
| 0 1 | 0 1 | 1 2 | *1 2* |

Finally, the relation (E, F, Link1) is then consulted to deduce a consequence of Link1 bound to the values 1, 2:

| E | F | Link1 |
|---|---|-------|
| *1* | *0* | 1 2 |

Thus, the state propagation on the tree structure of interconnected relations (by the valid states of the common link variables) ensures completeness of a given deduction; in other words, all constraints on all variables are deduced in embodiments of the present disclosure.

It will be appreciated that a completeness of deduction is not possible by state propagation on the array representation of the user-defined relations R0, R1, R2, R3, R4. For example, when asserting "A true" on the relation R0, it is not possible to deduce further constraints on variable D. Thus, there arises a need to colligate all interconnected relations in advance, even on such a very simple cyclic structure with only a single variable connecting each relation pair. The simple colligation strategy (namely ADB) technology described in the following is susceptible to being summarized as follows:

1. A given process of joining relations with common variables and linking isolated relations on isolated variables is potentially impossible to implement in practice on large sets of relations due to a possible blow-up in size of a corresponding joined result (namely, is computationally impossible to achieve in practice using contemporary computing hardware). Such a requirement for huge computational resources is an insurmountable and constant issue arising on account of a complexity of rules in a range of practical technical fields of use of intelligent data processing systems in fields such as healthcare and life sciences.
2. If the process of joining relations can be completed, a binary output that is thereby achieved does satisfy a requirement for completeness, but does not satisfy other requirements for embedded solutions, namely:
   a. A representation thereby derived will not be as compact as possible, and potentially must be reduced in size, for example minimized in size, to meet specific hardware requirements for achieving size and real-time capability.
   b. A complete solution space will not necessarily be accessible by parallel processing hardware using simple instructions, for example using GPUs.
   c. The complete solution space must be addressable in order to include object functions. A compressed data format (namely, nested Cartesian arguments) is not a suitable representation for variables defining an object function; relations for these variables are beneficially in an expanded form representing all valid tuples rather than Cartesian arguments.
   d. Relations without any constraints (tautologies) are potentially also a part of static constraints of a system model interacting with dynamic constraints from an environment.

The array system model (ASM) that is described in the following paragraphs meets all these requirements (a) to (d) and thus represents a technically advanced embodiment of the present disclosure.

Parallel Colligation

A process of colligation pursuant to an embodiment of the present disclosure is illustrated in FIGS. 34A to 34C.

Initially, relations are joined pairwise using an approach as described in published patent documents WO 09948031A1 and WO 2001022278A1. Moreover, isolated variables (namely, variables only present in their corresponding single relations) are separated and linked into new relations. A trivial case of parallel colligation is to join all relations into a single relation (wherein such an approach is suitable for smaller problems) or into a tree structure of interconnected relations with isolated variables (wherein such an approach is suitable for larger problems), and the colligation is thus thereby completed.

Figure 4:
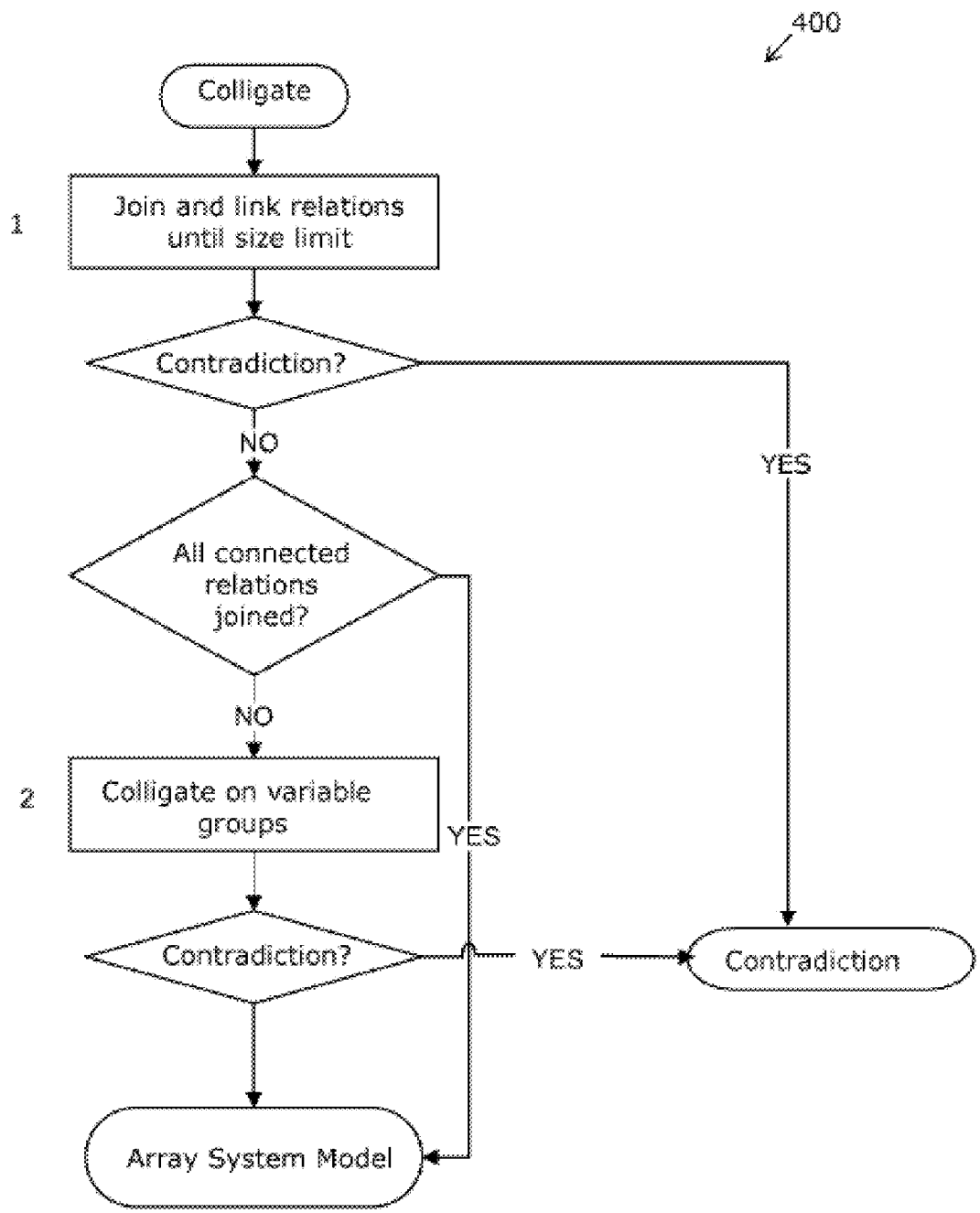
FIG. 4 is an illustration of a colligation strategy employed in the method of FIG. 2.

In respect of aforementioned larger problems, it is not potentially feasible to use known joining methods due to a size of the joined result arising from such joining methods. It is thereby beneficial to introduce a parallel colligation of smaller parts of the system, wherein:
(i) a parallel join of a relation pair is illustrated in FIG. 4 (Step 1) and also in FIG. 34A; and
(ii) a parallel colligation of variable groups is illustrated in FIG. 4 (Step 2) and FIG. 5.

Parallel Join of Relation Pairs

A flow diagram, namely a workflow, is illustrated in FIG. 34A. Moreover, in FIG. 34B, there is shown an example of two relations on Boolean variables A, B, C, D, E, F, G as well as a joined result:

R0: (A and B)→(C or D or E)
R1: (C or D or E)→(F and G)

In an internal array representation in compressed form, R0 and R1 are represented by 5 and 3 Cartesian arguments, respectively. Such small relations are susceptible to being joined in different ways, for example by comparing all 5×3 argument combinations by intersections of the Boolean variables C, D, E that are common thereto. However, in respect of large relations, for example with 5 million arguments and 3 million arguments respectively, such an approach would cause a combinatorial explosion of possible argument intersections, which would be very expensive in terms of central processing unit (CPU) resources and data memory to compute in a practical example, for example in an industrial controller functioning in real-time.

Thus, pursuant to embodiments of the present disclosure, it is therefore beneficial to use a much more efficient methodology for colligating a smallest possible subsystem spanned by just a single variable. In FIG. 34C, there is shown an illustration of a process of colligating the common Boolean variable C in the relations R0 and R1. A following procedure is used, as illustrated in the workflow shown in FIG. 34A, and can be executed in parallel on each common Boolean variable C, D, E, wherein the procedure includes steps of:

Step 1: Determining attributes "AP" from R0 and R1;
Step 2: Determining unique elements from the attributes "AP" (hereinafter denoted by "DAP");
Step 3: Determining indices of "AP" in "DAP" (hereinafter denoted "GI");
Step 4: Carrying out a basic colligation by use of intersection of a minimum number of combinations in "DAP", resulting in all intersections being represented, for example, by a 3×2 matrix "J0";
Step 5: Identifying non-empty intersections of "J0" and storing a corresponding result in a Boolean matrix "BM0"; and then
Step 6: Updating the global Boolean matrix "BM" representing matching arguments of R0, R1.

Following steps of a join algorithm has a result of expanding the local intersections of each variable to the matching indices of arguments in the joined relation. This indexing procedure is highly efficient and does not benefit from being implemented by employing parallel data processing. For example, after colligation of all the Boolean variables C, D, E, the following Boolean matrix "BM" represents the matching combinations of the 5 arguments in R0 and the 3 arguments in R1:

| BM: |
| --- |
| 1 1 1 |
| 0 0 1 |
| 0 0 1 |
| 0 0 1 |
| 1 1 1 |

The indices of the valid argument combinations in "BM" are represented in a 2×9 matrix denoted "BM2", wherein a first row represents the indices in R0, whereas a second row represents the indices in R1:

| BM2: |
| --- |
| 0 0 0 1 2 3 4 4 4 |
| 0 1 2 2 2 2 0 1 2 |

Thus, it will be appreciated from the foregoing the number of arguments (9) in the joined result, and therefrom can be predicted data memory requirements for computing and storing results. The local results of each colligated variable is now expanded to the attributes of the joined relation using the associated indices.

For example, for variable C has the indices (GI):

| | |
| --- | --- |
| 0 1 1 2 0 | 0 0 1 |

The first item of "GI" has the following indices of the first row in BM2:
(0 1 1 2 0)[0 0 0 1 2 3 4 4 4]=0 0 0 1 1 2 0 0

Similarly, the second item of "GI" has the following indices of the second row in "BM2":
(0 0 1)[0 1 2 2 2 2 0 1 2]=0 0 1 1 1 1 0 0 1

Thus, the follow 9 local combinations from "J0" must be used in the joined result:
0 0 0 1 1 2 0 0 0 (first axis)
0 0 1 1 1 1 0 0 1 (second axis)

In summary and conclusion, the attribute of the Boolean variable C in the joined relation has the following 9 cells:

| | | | | | | | | |
| --- | --- | --- | --- | --- | --- | --- | --- | --- |
| 0 | 0 | 0 | 0 1 | 0 1 | 1 | 0 | 0 | 0 |

Parallel Colligation of Variable Groups

In order to elucidate embodiments of the present disclosure in further detail, an example will be described with reference to FIG. 6.

Colligation Strategy for Variable Groups

A process of colligation pursuant to an embodiment of the present disclosure is illustrated in FIG. 4. Initially, relations are joined and compressed pairwise using an approach as described in published patent documents WO 09948031A1 and WO 2001022278A1 (namely, as per Step 1 in the foregoing). Isolated variables (only present in a single relation) are separated and linked into new relations. A trivial case is to join all relations into a single relation (suitable for small problems) or the tree structure of connected relations with isolated variables (suitable for larger problems), and the colligation is thus thereby completed.

On large problems, it is not potentially feasible to join all relations due to the size of the joined result. It is thereby beneficial to introduce the colligation of relations on selected variable groups; this is illustrated in FIG. 4, Step 2.

In order to elucidate embodiments of the present disclosure in further detail, an example will be described with reference to FIG. 6. After employing an initial joining and linking process, there are thereafter three relations (shown as boxes in bold) that are yet to be joined. These three relations have following variables, most of which are shared (the relations are linked to previously isolated relations by link variables 70, 71 and 72):

(1 2 3 4 5 22 37 50 70)(1 2 3 4 5 6 11 26 37 42 44 47 50 71)(1 2 3 5 6 11 22 42 44 47 72)

Figure 5:
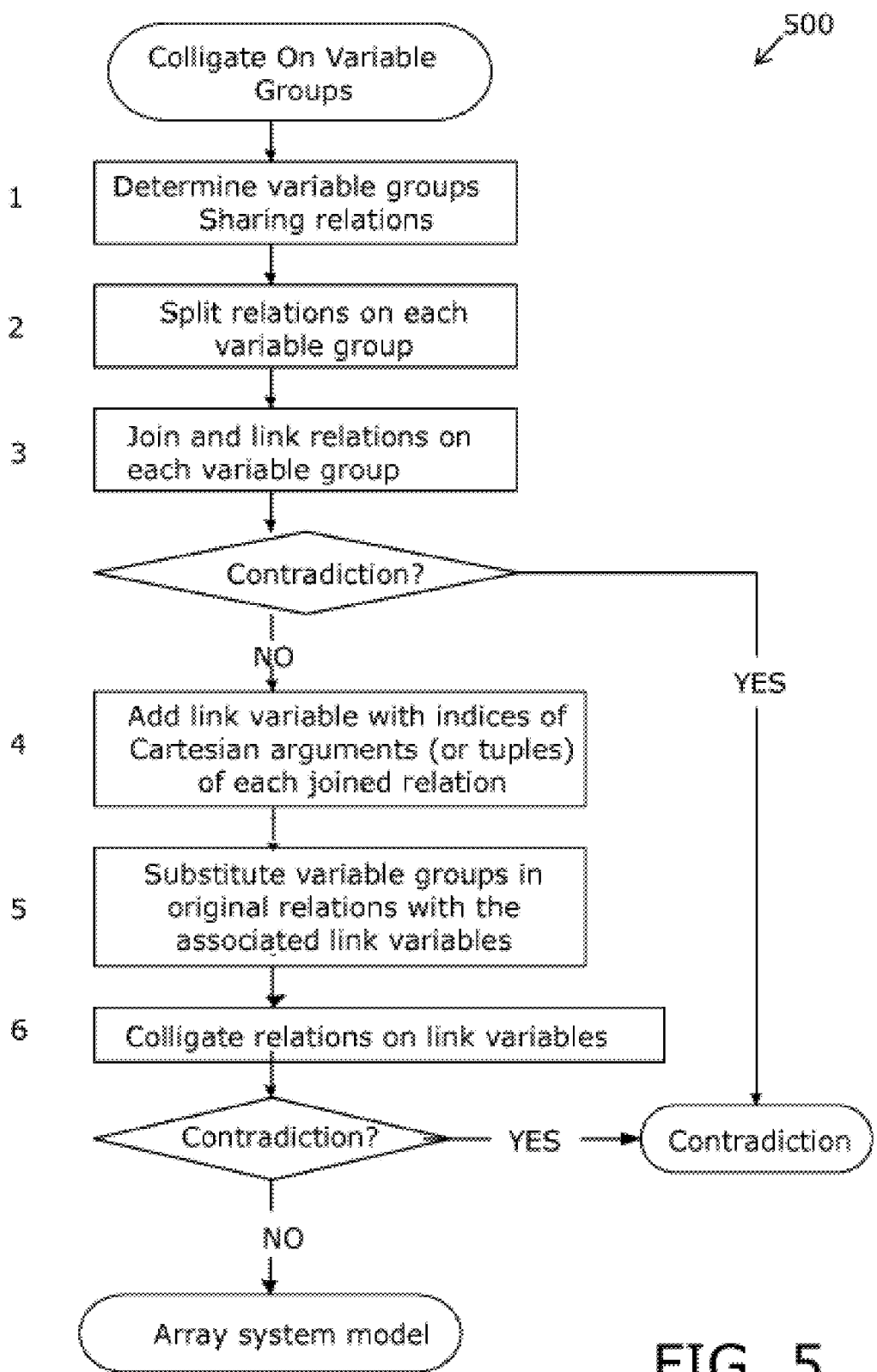
FIG. 5 is an illustration of a colligation applied to variable groups.

The number of Cartesian arguments in the three relations is very large, and it is not possible to join the relations. It is therefore necessary to colligate in respect of groups of variables shared by same given relations. A corresponding workflow for such colligation is illustrated in FIG. 5, wherein the workflow will be elucidated in greater detail below.

Step 1: Determine Distinct Variable Groups Shared by Two or More Relations (FIG. 6 and FIG. 7)

In a step 1, all variables are grouped that are shared by same relations. In FIG. 7, there is provided an illustration of the structure of three relations to be joined. There are four different collections of variables, namely (1 2 3 5 22), (1 2 3 5), (4 37 50) and (6 11 26 42 44 47). An aim in the step 1 is to find distinct groups (namely, with no overlap), and therefore there is performed a merging of the small group (1 2 3 5) into the larger one (1 2 3 5 22). Such merging provides result in a form of three distinct variable groups: (1 2 3 5 22)(4 37 50)(6 11 26 42 44 47)

Step 2: Split Relations on Each Variable Group (FIG. 7)

As shown in FIG. 7, all three relations share the variable group (1 2 3 5 22). There is made a copy of the relations on these variables and the associated link variables 70, 71, 72, as follows: (1 2 3 5 22 70)(1 2 3 5 71)(1 2 3 5 22 72)

Step 3 and 4: Join and Link Relations on Each Variable Group (FIG. 7 and FIG. 8)

Joining the relations on the variable group (1 2 3 5 22) yields a relation with the following variables: (1 2 3 5 22 70 71 72). Next, the variable group is isolated, and there is thereafter added a new link variable (Link0) indexing each Cartesian argument of (1 2 22). There is thereby generated a result that a relation with following variables:

(1 2 3 5 22 70 17 72 Link0)

Step 5: Substitute Variable Groups in Original Relations with the Associated Link Variables (FIG. 8)

To illustrate, the relation (1 2 3 5 22 70 71 72 Link0) defines the relationship between variables (70 Link0). There is then determined the values of Link0 for each index (argument) of variable 70 and the variables (1 2 3 5 22) removed from the original relations.

Step 6: Colligate Relations on Link Variables (FIG. 8 and FIG. 9)

As shown in FIG. 8, the original relations are now defined on the link variables of isolated relations:

(Link0 Link1 70)
(Link0 Link1 Link2 71)
(Link0 Link2 72)

These results are also colligated by join and, if possible, to isolate variables. Assuming that it is required to join to provide a single relation, there is thereby provided a relation shown in FIG. 9:

(Link0 Link1 Link2 70 71 72)

Minimize and Link Complete Solution Space

Furthermore, with reference to FIG. 1, there is thereby now completed the colligation process yielding a complete solution space. All invalid combinations are eliminated (with a state of contradiction as a special case). A final task is to prepare a model for embedded applications, namely to seek to minimize a size of the binary file (to achieve compactness) and to optimize a run-time performance in respect of specific hardware, whether with or without parallel processing capabilities, for example multi-core GPUs are susceptible of providing parallel processing functionality.

A workflow is shown in FIG. 10, wherein each individual relation is potentially split into more relations in two different ways, depending upon a size of an output to be generated and upon whether or not there is use made of parallel processing hardware.

Option 1: Split Core Relation into Pairs and Split Model for Parallel Processing A workflow for option 1 in shown in FIG. 11. A given relation is extended with a link variable (LINK) indexing the Cartesian arguments (in a compressed form) or tuples (in an expanded form) of the given relation with variables VAR1, VAR2 VARn. The given relation is then split into n derived relations on (VAR1, LINK), (VAR2, LIN K), (VARn, LINK), respectively; n is an integer of value 2 or greater (namely, a plurality). Such a method will always be used on a core relation of a complete array system model, whenever the model is to be split and distributed for parallel processing. To illustrate, there is used an array system model as illustrated in FIG. 13. The core relation (namely, a root of the tree) is a relation on variables (70, 71, 72, 73, 74, 75, 76), wherein a variable 76 is a new link variable (LINK), while all the other variables are link variables generated in a previous colligation process.

In FIG. 14, there is illustrated the core relation split into its corresponding relation pairs (70 76), (71 76), (72 76), (73 76), (74 76) and (75 76). It is thereby feasible to split the entire array system model into 6 (or less) sub-models distributed upon 6 hardware cores. In a runtime environment, it is thereby feasible to ensure completeness of deduction by a simple state propagation of a state vector with the variable 76 linking the distinct cores together.

Option 2: Split Relation into Tree Structure of Interconnected Relations

A workflow is shown in FIG. 12, whereas, in FIG. 15, there is illustrated how the original relation (6, 11, 26, 42, 44, 47, 75) is split into a tree structure of relations (represented in bold boxes). There is employed a method as follows:

Step 1: Find Smallest Derived Relation on N Variables, for Example N=2 on Variables VAR1, VAR2

In the present example, in the Step 1, the smallest number of Cartesian arguments (or, alternatively, tuples in expanded form) is on the variables (6, 26).

Step 2, 3: Add New Link Variable and Isolate Relation

In the Steps 2 and 3, the relation on variables (6, 26) is extended with a link variable 78 and then isolated (namely stored) for the binary output file.

Step 4: Update Relation R: Remove VAR1, VAR2 and Substitute with Link Variable

In the present example, the original relation (6, 11, 26, 42, 44, 47, 75) now has the following variables: (11, 42, 44, 47, 75, 78). In the method, the aforementioned Steps 1 to 4 of the method are executed recursively to yield a following list of relations: (11, 78, 79), (42, 47, 80), (44, 79, 81) and finally a relation (75, 80, 81), which is not split (namely, representing a root of the aforementioned tree).

Building Decision Support Systems Using Embodiments of the Present Disclosure

An example application of embodiments of the present disclosure is to develop a personalized decision support system that is delivered by using a mobile telephone software application (namely "mobile app") that can be used in-store or at home to help individuals to identify and choose foods, that help optimize their lifestyle to be more healthy, given their combination of clinical diagnoses and prescriptions, food sensitivities, health goals and disease risks; as such, when employed in such a manner, embodiments of the present disclosure are not employed in a manner of a method of treatment of the human or animal body. This will help individuals become more informed and engaged in managing their health and contribute to reducing the societal impact of chronic diseases. A health project beneficially involves gathering a large amount of publicly available and clinically/scientifically validated source data and constructing from this an Array System Model (ASM) that can be loaded onto a mobile device and used (via a runtime API running on the mobile device) to provide personalized decision support recommendations and advice to users either in store, when shopping on-line or at home. The construction of the Array System Model and Decision Support Application is a multi-stage process involving the following steps:

Step 1—Mining of Source Data and Semantic Normalization

Step 2—Compilation & Validation of an Array System Model, for example using aforementioned colligation Step 3—Accessing the Array System Model on a mobile/wearable device via a Runtime API using a given user's Input State Vector to provide personalized decision support to the given user Mining of Source Data and Semantic Normalization A starting point for developing a predictive Array System Model (ASM) based on an understanding of a combinatorial effect of a given user's set of pharmaceutical drugs, diseases and diet is a list of their known (reported) direct interactions. This is however only a first-order list of interactions, and to enable inferences about the combinatorial effects to be made, the interactions have to be mapped onto a semantically normalized set of receptors, organs and other systems and pathways in the body, so that cumulative inhibitory and excitatory interactions can be predicted.

Information describing all known serious and/or moderate interactions between certain drugs and other drugs, diseases and foods is required to be disclosed publicly. These are reported and reproduced in patient and professional warning labels and inserts including in drug packaging, from which an extract describing known drug:food interactions is shown in FIG. 27. Such information is required as input data in embodiments of the present disclosure. Moreover, such information can be supplemented, if necessary, with information from research reports, medical investigations and personal experiences of medical practitioners.

In addition to the formal reporting of these interactions (managed by regulatory agencies such as FDA, EMEA and MHRA, and so forth), and collections such as the Electronic Medicines Compendium, drugs.com and DrugBank, there are more anecdotal sources of interaction information including the AERS (Adverse Event Reporting System); such names include trademarks. In one embodiment of the present disclosure, over ten (10) of these "definitive" drug interaction data sources from different countries are integrated and semantically normalized to identify all potential drug-disease-food interactions, their basic mechanisms of action and sites of action in receptors, organs and systems across the human or animal body (as far as they are known and/or reported) as shown in FIG. 17. In total, information pertaining to over 500,000 interactions associated with over 8,500 drugs (including generic drugs and prescription/trade names) are integrated and extracted from drugs' patient information labels, black box warnings and professional clinician prescription advisories. In total, in an order of 136,784 drug-disease interactions are beneficially collected. Since a same given drug exists under many proprietary market names (for example acetylsalicylic acid is sold as: Bayer Aspirin, Bayer Children's Aspirin, Bufferin, Easprin, Ecotrin, and so forth, wherein these names include trademarks), the initial database is beneficially semantically normalized in respect of an active pharmaceutical ingredient, down to a detail on a knowledge graph containing 9,526 drug-disease interactions representing interactions of 2,545 drugs' active ingredients. Such a large amount of data would be too great for a medical practitioner to remember accurately.

Natural language processing, semantic distance and machine learning tools are beneficially also applied to build a semantically normalized ontology and knowledge graph of the food types (for example, in respect of broad categories such as alcoholic drinks) and food ingredients (for example, vitamin K in broccoli) for all foods. Such an ontology is then beneficially used to identify those foods and ingredients that have a potential to interact with the set of drugs as aforementioned.

Food records represented in the knowledge-graph represent a broad range of different levels of abstraction, allowing for more inclusive and flexible predictions to be made in embodiments of the present disclosure. A lower level of abstraction is represented by chemical substances, for example Potassium, vitamin K, and so forth. A middle level of abstraction is represented by simple food products, for example grapefruit juice or broccoli. A higher level of abstraction is represented by classes of food products: green leafy vegetables, dairy products, smoked meat, or aged cheese, for example.

This use of different levels of classification, namely abstraction, allows for making very broad recommendations to a given user, for example in respect of all alcoholic drinks, regardless of whether or not it is wine, beer, vodka and so forth, down to a detail of very narrow and specific components of more complex foods (for example, processed food products that contain smoked meat products and therefore have high levels of tyramine). In total, there are, for example, 1,899 reported interactions between different food types and/or ingredients and drugs, and each of these interactions is stored in a knowledge graph with evidence for the interaction, for use in data processing associated with embodiments of the present disclosure.

Compilation of Array System Model

In an example embodiment of the present disclosure, information pertaining to food and drug interactions is semantically normalized into a single knowledge graph for use in the compilation of an Array System Model as shown in FIG. 18.

In order to analyze and calculate potential interactions between combinations of multiple foods, drugs and diseases, an entirety of an inverse solution space (namely, combinations of foods and drugs that are known to cause problems) is compiled using methods as described in the foregoing into a nested array system model. Only the components, drugs and diseases that actually have the potential to present risks are contained in the Array System Model; all non-interacting factors are removed during the model compilation step in order to provide for more efficient data processing and thereby deliver results more promptly. Thus, in the example embodiment, a usual model logic is inverted, because there are many fewer interaction causing combinations than non-interaction causing. It is easier, quicker and uses far less memory to store only those potentially troublesome combinations. By such an approach, non-troublesome combinations are effectively "filtered out" of computations, thereby enabling the computations to be executed more rapidly, using less computing resources.

An example validated Array System Model used in this given embodiment has:
- 1,064 interacting food components (from 186,589 food items);
- (ii) 2,545 drugs with potential interactions (from 9,526 pharmaceutical ingredient interactions); and
- (iii) 324 diseases with potential interactions (from over 8,500 analyzed).

Abduction

In embodiments of the present disclosure, the method comprises (using the aforesaid PACE engine) computing one of three different types inferences, namely: deduction, abduction or induction, as described in the following examples:

Deduction:
General method:
Rule: If A, then B.
Observation: A is true.

Conclusion: B is true.
The method (using the aforesaid PACE engine):
SV1 (input state vector): A is true, B is unknown.
SV2 (output state vector): A is true, B is true.
Abduction:
General method:
Rule: If A, then B.
Observation: B.
Conclusion: Possibly A.
The method (using the aforesaid PACE engine):
Find all input state vectors (SV1) implying output state vector (SV2) B is true. For example, find SV1(a), SV1(b), SV1(c) . . . SV1(n) implying SV2(B).
Induction:
General Method:
Observed: A.
Observed: B.
The method (using the aforesaid PACE engine):
All asserted and/or measured states from an environment are captured, counted and represented in a table. For example, where four different asserted and/or measured states are counted:

| A | B | Count |
|---|---|---|
| 0 | 0 | 300 |
| 0 | 1 | 50 |
| 1 | 0 | 3 |
| 1 | 1 | 600 |

The above table is an array system model computed using the PACE engine, with all asserted and/or measured states from the environment. Furthermore, all four valid states may be represented with an object function (Count), or rare observations may be eliminated (to be considered invalid), in order to build compact and fast models. For example:

| A | B | Count (truth table of implication: A implies B) |
|---|---|---|
| 0 | 0 | 300 |
| 0 | 1 | 50 |
| 1 | 1 | 600 |

| A | B | Count (truth table of implication: A implies B and B implies A) |
|---|---|---|
| 0 | 0 | 300 |
| 1 | 1 | 600 |

Thus, the method allows deduction and abduction to be performed on an existing decision support knowledge model. Furthermore, the method allows induction to be performed to build a decision support knowledge model based on asserted and/or measured states (or state vectors) from the environment.

Accessing the Array System Model on a Mobile Device for Personalized Decision Support This array system model is converted by the Array System Model compiler as shown in FIG. 18 into a verified and normalized structure, that can be represented in a 428 KB file, which is an amount of memory the model consumes when loaded into an Array Runtime API on a given user's mobile device, for example a smart phone or a smart watch. A significant proportion of this memory (namely, over 60% thereof) is simply used for storing names of drugs being considered in the computation, as well as diseases and foods; such data is potentially further optimized, if necessary, so that the Array System Model requires even less computing resources in operation.

This Array System Model (ASM) provides an analytical and predictive substrate to power a personalized decision support app (namely, application software) on the given user's mobile device. This substrate enables the Runtime API running directly on the user's mobile device (smart watch, phone, or tablet) to use the Array System Model to perform logical inferences on the data and deduce all the consequences of, for example, a given patient's parameters for a selected set of food items. The decision support system employed in embodiments of the present disclosure is capable of identifying food items, for example in an online shopping basket as shown in FIGS. 19, 24 and 25, that are potentially detrimental to a given user as they pose a high risk of interactions. The given user has previously entered, for example, diseases from which the given user suffers and drugs that the given user is taking (comprising their input state vector) as shown in FIG. 23. As shown in FIG. 20, food items that present a risk to the given user might well otherwise be thought to constitute part of a healthy diet, for example broccoli, for other users.

The decision support systems as employed in embodiments of the present disclosure are also capable, when in operation, of suggesting foods from a same given category that avoid any potential for interaction with the given user's diseases and drugs, as shown in FIGS. 21 and 26. If such suggestions were adopted by the given user, embodiments of the present disclosure would enable the given user to substitute immediately substituted alternative products in the given user's shopping basket, when making purchases for example, using online shopping API's. Embodiments of the present disclosure are operable to provide a decision support system for performing aforementioned analyses within a predictable and very short time; for example, a proprietary Google Nexus 7 tablet computer running an Android software platform is capable of implementing analyses within five to ten milliseconds. Such computational performance is provided with a constant and low memory footprint (namely, around 430 kBytes in practice), and is guaranteed to find all the potential adverse consequences given by constraints imposed by a given user's input state vector (namely, in this case, the given user's profile of diseases and drugs). However, it will be appreciated that embodiments of the present disclosure can be used for other purposes, for example to control complex industrial systems, receiving inputs from physical sensors and human-operated controls, and provide various outputs for controlling valves, baffles, pumps, heating elements, cooling apparatus, and so forth, of the complex industrial systems. Thus, embodiments of the present disclosure can, for example, be implemented as industrial controllers and electronic management systems wherein a complex combination of input parameters needs to be processed in order to provide appropriate control outputs.

Operational characteristics of embodiments of the present disclosure are especially crucial when running a massively complex problem such as:

(i) personalizing dietary advice for polypharmaceutical patients with multiple chronic diseases, wherein the dietary advice is provided on a low-power mobile device with limited CPU and memory resources;

(ii) providing control to a highly complex industrial facility, for example to a manufacturing plant, chemicals processing plant, to emergency support for an industrial accident (for example, as occurred at Fukushima Dai'ichi (Japan), with triple reactor core meltdowns and the resulting large numbers of waste water storage tanks that need constant control); and so forth.

DETAILED DESCRIPTION OF DRAWINGS

Referring to FIG. 1, there is shown an illustration of an array system model (ASM) 100 in accordance with an embodiment of the present disclosure. Referring to FIG. 2, there is shown an illustration of a method 200 of using the array system model 100 of FIG. 1, by employing a process of state deduction.

Figure 3A:
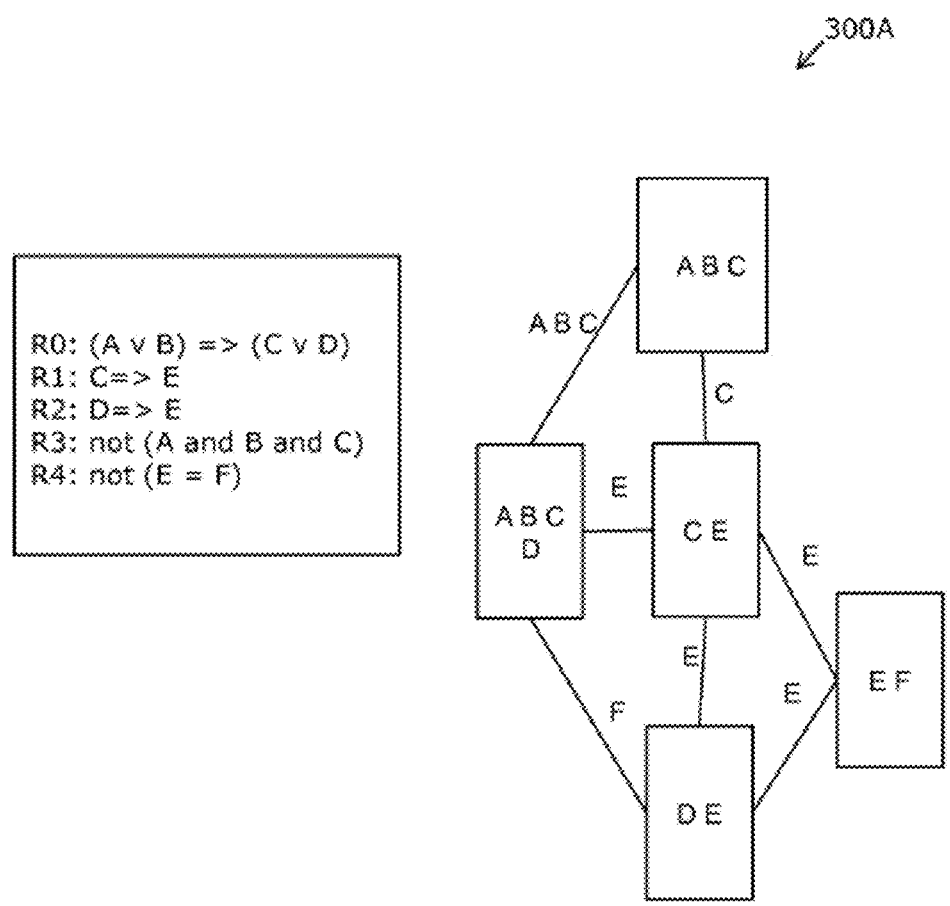
FIGS. 3A and 3B are illustrations of an example pertaining to FIG. 1 and FIG. 2.

Referring to FIG. 3A, there is shown an exemplary cyclic colligation graph 300A (pertaining to FIG. 1 and FIG. 2) before colligation, in accordance with an embodiment of the present disclosure.

Figure 3B:
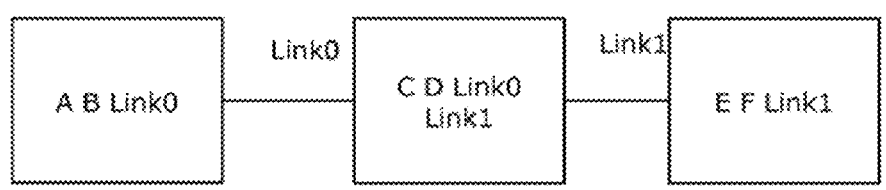

Referring to FIG. 3B, there is shown an exemplary tree structure 300B after colligation, in accordance with an embodiment of the present disclosure.

Referring to FIG. 4, there is shown an illustration of a block diagram of a process of colligation 400 to in the method 200 (of FIG. 2) for using the array system model 100 (of FIG. 1), in accordance with an embodiment of the present disclosure.

Referring to FIG. 5, there is shown an illustration of a block diagram of colligation 500, in accordance with an embodiment of the present disclosure.

Referring to FIG. 6, there is shown an illustration of a step 1 600 of the process of colligation 400 of FIG. 4, in accordance with an embodiment of the present disclosure.

Referring to FIG. 7, there is shown an illustration of a step 2 700 of the process of colligation 400 of FIG. 4, in accordance with an embodiment of the present disclosure.

Referring to FIG. 8, there is shown an illustration of a step 3 800 of the process of colligation 400 of FIG. 4, in accordance with an embodiment of the present disclosure.

Referring to FIG. 9, there is shown an illustration of a step 4 900 of the process of colligation 400 of FIG. 4, in accordance with an embodiment of the present disclosure.

Referring to FIG. 10, there is shown an illustration of a block diagram of splitting and minimizing a relation 1000 to the method 200 (of FIG. 2) for using the array system model 100 (of FIG. 1), in accordance with an embodiment of the present disclosure. Referring to FIG. 11, there is shown an illustration of a splitting of a relation into pairs, in accordance with an embodiment of the present disclosure. Referring to FIG. 12, there is shown an illustration of a splitting a relation into a tree structure, in accordance with an embodiment of the present disclosure.

Referring to FIG. 13, there is shown an illustration of a splitting model 1300 employed to perform parallel computing in a step 1 600 (of FIG. 6), in accordance with an embodiment of the present disclosure.

Referring to FIG. 14, there is shown an illustration of a splitting model 1400 employed to perform parallel computing in a step 2 700 (of FIG. 7), in accordance with an embodiment of the present disclosure. Referring to FIG. 15, there is shown an illustration of a method of minimizing 1500 an array system model 100 (of FIG. 1) when performing runtime applications, in accordance with an embodiment of the present disclosure.

Referring to FIG. 16, there is shown an illustration of state propagations 1600 that are employed when implementing embodiments of the present disclosure. Referring to FIG. 17, there is shown an illustration of a data mining and semantic normalization 1700 that is employed when implementing embodiments of the present disclosure.

Referring to FIG. 18, there is shown an illustration of a compilation and validation 1800 of an Array System Model 100 (of FIG. 1), in accordance with an embodiment of the present disclosure.

Referring to FIG. 19, there is shown an illustration of an online shopping basket 1900, in an exemplary use of step 1 600 of FIG. 6 in the Array System Model 100 of FIG. 1, in accordance with an embodiment of the present disclosure.

Referring to FIG. 20, there is shown an illustration of an online shopping basket 2000, in an exemplary use of step 2 700 of FIG. 7 in the Array System Model 100 of FIG. 1, in accordance with an embodiment of the present disclosure.

Referring to FIG. 21, there is shown an illustration of an online shopping basket 2100, in an exemplary use of step 3 800 of FIG. 8 in the Array System Model 100 of FIG. 1, in accordance with an embodiment of the present disclosure. Referring to FIG. 22, there is shown an illustration of an online shopping basket 2200, in an exemplary use of step 4 900 of FIG. 9 in the Array System Model 100 of FIG. 1, in accordance with an embodiment of the present disclosure.

Referring to FIG. 23, there is shown an illustration of a user interface 2300 defining a given user's input state vector, in accordance with an embodiment of the present disclosure.

Referring to FIG. 24, there is shown an illustration of online shopping baskets 2400 for use with embodiments of the present disclosure.

Referring to FIG. 25, there is shown an illustration of an exemplary use 2500 of Array System Model 100 (of FIG. 1) for identifying a given example user's risk of encountering interaction with food items, in accordance with an embodiment of the present disclosure.

Referring to FIG. 26, there is shown of an illustration of an exemplary use 2600 of the Array System Model 100 (of FIG. 1) to suggest alternative safer food items for a given example user, in accordance with an embodiment of the present disclosure.

Referring to FIG. 27, there is shown an illustration of a drug warning label information 2700, pertinent to embodiments described in the present disclosure.

Referring to FIG. 28, there is shown an illustration of a cluster with four distinct states 2800, pertinent to embodiments described in the present disclosure.

Referring to FIG. 29, there is shown an illustration of a cluster relation 2900 which includes cluster states and variables, in accordance with an embodiment of the present disclosure.

Referring to FIG. 30, there is shown an illustration of a clustering application workflow 3000 pertaining to precision medicine, in accordance with an embodiment of the present disclosure. At a left-side of FIG. 30, sets of external variables are prepared; these can potentially be many millions in number. Next, cluster relations are defined that interlink the external variables to generate internal variables together with their static constraints. From the internal variable and their static constraints are generated out states (SV).

Referring to FIG. 31, there is shown an illustration of a cluster relation 3100 pertaining to precision medicine, pertinent to embodiments described in the present disclosure. Referring to FIGS. 32A and 32B, there is shown an illustration of state-event rules 3200A and 3200B for performing state-event processing, in accordance with an embodiment of the present disclosure.

Referring to FIG. 33, there is shown an illustration of a clustering application workflow 3300 pertaining to state-event processing, in accordance with an embodiment of the present disclosure.

Referring to FIGS. 34A to 34C, there are shown illustrations of steps of processes of colligation, particularly, FIG. 34A is a flow diagram 3400A of a process of colligation, FIG. 34B is exemplary representation 3400B of two relations on Boolean variables A, B, C, D, E, F, G as well as a joined result of the two relations, and FIG. 34C is a process of colligation 3400C of common Boolean variable C in the relations RO and R1 of FIG. 34B, in accordance with an embodiment of the present disclosure.

Figure 35B:
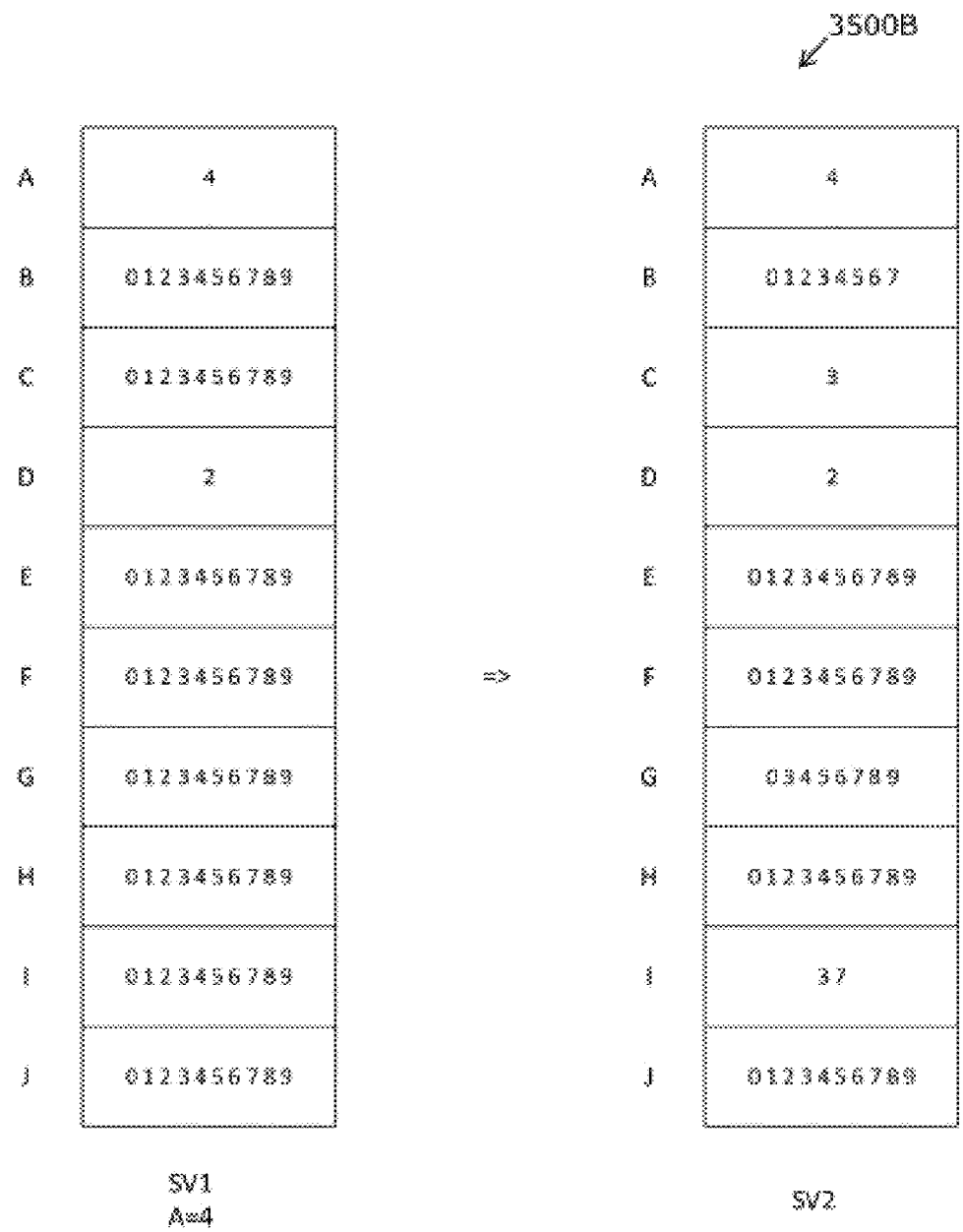

Referring to FIGS. 35A to 35F, there are shown illustrations of run-time example of array system models, particularly FIG. 35A is a vector 3500A of a compiled array system model, FIGS. 35B-35F are various outputs 3500B, 3500C, 3500D, 3500E and 3500F of the vector 3500A of FIG. 35A, in accordance with an embodiment of the present disclosure.

Referring to FIG. 36A, there is shown an illustration of a solution space depicted as a matrix 3600A after compilation of following two relations on Boolean variables A, B, C, D, E, F, G, in accordance with an embodiment of the present disclosure.

Referring to FIG. 36B there is shown an illustration of an internal binary representation 3600B of the aforesaid relations of FIG. 36A in terms of nested attributes with two elements, in accordance with an embodiment of the present disclosure.

Referring to FIG. 36C there is shown an illustration of the internal binary representation 3600C of FIG. 36B using indexed attributes, which is a most effective representation of relations with a large number of redundant nested cells, in accordance with an embodiment of the present disclosure.

Internal Binary Representation of Relation

In a given run-time environment, any kind of logical inference or reasoning is determined by a simple state propagation on compiled and linked relations. Since the compiled array system model of the present disclosure potentially includes several layers of nesting (for example, Cartesian subspaces in relations, relations in clusters, clusters in models), an internal binary representation of relations must be optimized to ensure that a very fast state deduction is susceptible to being generated when employing limited computing resources, for example battery-operated personally wearable devices, even on very complex array system models with several layers of nesting. Embodiments of the present invention in such an example are capable of reducing power consumed by computing devices for implementing a cognitively-complex technical control task.

In FIG. 36A, there is shown an illustration of a solution space 3600A depicted as a matrix after compilation of following two relations on Boolean variables A, B, C, D, E, F, G:

R0: (A and B)→(C or D or E)
R1: (C or D or E)→(F and G)

In FIG. 36B, there is shown an illustration of an internal binary representation 3600B of the aforesaid relations in terms of nested attributes with two elements, namely, a pair of elements including a first element and a second element. The first element of the pair is a list of attributes of each of the Boolean variables (ordered according to the domain order: A, B, C, D, E, F, G), while the second element is domain indices of variables: 0 1 2 3 4 5 6.

Using this internal binary representation, a bound input state must be colligated by intersection of all cells in respect of the associated attributes. For example, if it is asserted or measured that the variable A is to be bound to true, a value representing the variable A to be true must be colligated on a static relation by intersection of all cells in the attribute of variable C, namely:

(0 1)(0 1)(0 1)(0 1)(0)

In order to reduce, for example to minimize, the number of intersections, redundant cells are removed, and they are substitute with an associated index in a domain of unique cells. The domain of unique cells is:

(0 1)(0)

Assuming that an index origin is 0, associated indices of all 5 cells are:

1 0 0 0 0 1

If the Boolean variable A is bound in an input state vector, the number of intersections is now just 2, and a result derived therefrom can be expanded to all original cells by simple indexing.

In FIG. 36C, there is shown an illustration of the internal binary representation 3600C using such indexed attributes, which is a most effective representation of relations with a large number of redundant nested cells. Such a computation approach is therefore highly beneficial to apply in mobile computing devices, for example in personally wearable devices, when implementing embodiments of the present disclosure to reduce data processing power consumption.

Runtime Example of Array System Model

It will be appreciated from the foregoing that the array system model can be used, for example, as a basis for control systems that are configured, namely operable, to receive one or more physical measurands, for example as provided from one or more sensors coupled to an environment, and to provide outputs and conclusions that can be used to control items such as valves, motors, actuators for providing a technical modification of the environment. The environment can, for example include agricultural production facilities, humans, animals, apparatus and so forth.

In FIG. 35A, there is shown an illustration of a vector of a given compiled array system model with a state space of 10*10 combinations. It is assumed that this model is used for embedded state-event control in a small computing device, for example implemented as a control apparatus; a "small computing device" includes, for example a single 16-bit processor and a few Mbytes of data memory. All the interaction between the array system model and the environment is carried out by the state vector.

An unbound state vector (also called a "tautology state vector") represents on the projection on each axis in FIG. 35A. This array system model has ten (10) state variables, which can include cluster state variables or object functions. In order to simplify this example, it is assumed that each state variable can be assigned any of the ten (10) values 0, 1, 2, . . . 9.

Usually, state-event rules define a change of states defined by a given event, a pre-state and a post-state. On simple systems, such rules can be shown in a graph. In respect of FIG. 35A, the array system model is multi-dimensional with 10*10 possible combinations, and it is desirable to use static constraints in interaction with the state-event rules to ensure that any state vector is valid (see also FIG. 33). In other words, it is desirable to design consistent transitions between valid states in the multi-dimensional space.

In the example of FIG. 35A, it is assumed that a given pre-state and a certain event has triggered a new state (pro-state) with a variable D assigned a value 2. The pro-state only specifies one variable at a time, and a constraint engine deduces other state variables by one or more state deductions, which take into account different strategies for change of single state variables.

In this example, there is used a predefined order of variables in the state vector for selecting a next value. For example, in FIG. 35B, a variable A (namely, a first one in domain of variables) is assigned a value four (4). This value is a smallest possible decrease compared with the pre-state, where A=6. In general, each variable can be assigned simple rules for change of state on a single dimension, for example:
  (a) Selecting the largest value in the domain of valid elements;
  (b) Selecting the smallest value in the domain of valid elements;
  (c) Selecting the smallest decrease from the pre-state;
  (d) Selecting the smallest increase from the pre-state; and
  (e) Selecting the pre-state if possible (no change).

An output state vector SV2 in FIG. 35B represents a deduced projection on each axis with a given input state vector SV1. A next unbound variable is a variable B. In FIG. 35C, there is provided an illustration of a deduction using B=2, which is unchanged compared with the pre-state. A next unbound variable is E.

In FIG. 35D, there is provided an illustration of the deduction using E=9. Here, it is assumed that the largest value in a domain of valid elements is selected. A next unbound variable is F.

In FIG. 35E, there is provided an illustration of the deduction using F=7. This is a smallest decrease compared to the pre-state with the value F=8. A next unbound variable is I.

Figure 35F:
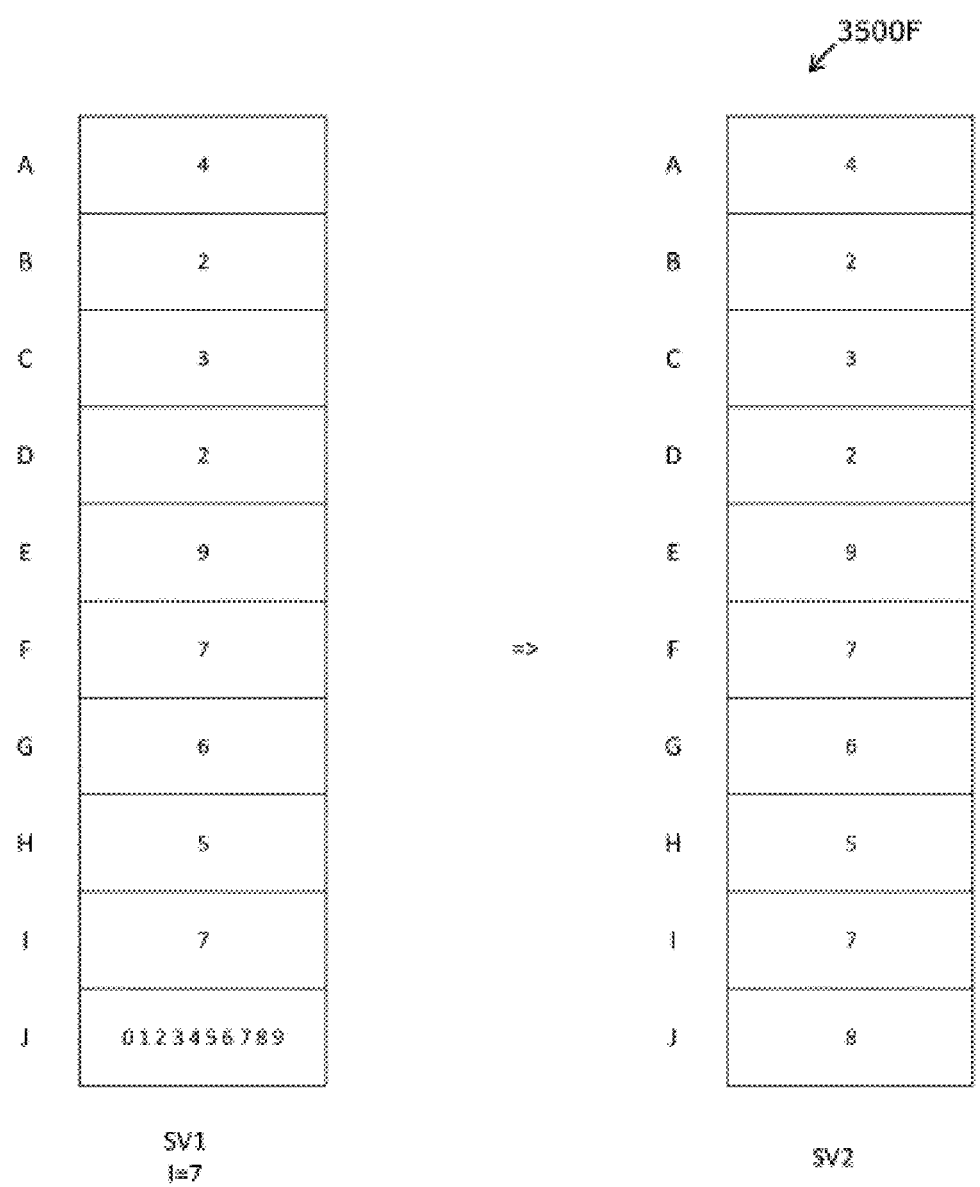

In FIG. 35F, there is provided an illustration of the deduction using 1=7, which is a smallest increase from the pre-state. The output state vector SV2 is now bound on all variables and represents a single state in the array system model. This is the physical post-state to be used in the embedded control system. This state vector is proven valid and will satisfy the constraints and the object functions in the array system model. For example, the state vector can then be used, for example, to control machinery, valves, medicine dispensing and so forth.

Building Decision Support Systems Using Embodiments of the Present Disclosure

An example use of embodiments of the present disclosure is to provide a personalized decision support system that is implemented by using a mobile telephone software application (namely "mobile app") that is susceptible to being used in-store or at home to help individuals to identify and choose foods, that help optimize their lifestyle to be more healthy, given their combination of clinical diagnoses and prescriptions, food sensitivities, health goals and disease risks; as such, when employed in such a manner, embodiments of the present disclosure are not employed in a manner of a method of treatment of the human or animal body. This will help individuals become more informed and engaged in managing their health and contribute to reducing the societal impact of chronic diseases. There is thereby provided, for example, a control apparatus that individuals can employ as their "personal assistants", for providing controlling advice and suggestions of benefit to the individuals. A health project involves gathering a large amount of publicly available and clinically/scientifically validated source data and constructing from this an Array System Model that can be loaded onto a mobile device and used (via a runtime API running on the mobile device) to provide personalized decision support recommendations and advice to users either in store, when shopping on-line or at home. The construction of the Array System Model and Decision Support Application is a multi-stage process involving the following steps:

Step 1—Mining of Source Data and Semantic Normalization;
Step 2—Compilation & Validation of Array System Model; and
Step 3—Accessing Array System Model on mobile/wearable device via Runtime API using the User's Input State Vector.

Step 1: Mining of Source Data and Semantic Normalization

A starting point for providing a predictive Array System Model (ASM) based on an understanding of a combinatorial effect of a given user's set of pharmaceutical drugs, diseases and diet is a list of their known (reported) direct interactions. This is however only a first-order list of interactions, and to enable inferences about the combinatorial effects to be made, the interactions have to be mapped onto a semantically normalized set of receptors, organs and other systems and pathways in the body, so that cumulative inhibitory and excitatory interactions can be predicted.

Information describing all known serious and/or moderate interactions between certain drugs and other drugs, diseases and foods is required to be disclosed publicly. These are reported and reproduced in patient and professional warning labels and inserts including in drug packaging, from which an extract describing known drug:food interactions is shown in FIG. 27. Such information is required as input data in embodiments of the present disclosure, for example to control apparatus utilizing data processing arrangements. In addition to the formal reporting of these interactions (managed by regulatory agencies such as FDA, EMEA and MHRA, and so forth), and collections such as the Electronic Medicines Compendium, drugs.com and DrugBank, there are more anecdotal sources of interaction information including the AERS (Adverse Event Reporting System); such names include trademarks.

In one embodiment of the present disclosure, over ten (10) of these 'definitive' drug interaction data sources from different countries are integrated and semantically normalized to identify:
  (i) all potential drug-disease-food interactions; and
  (ii) their basic mechanisms of action and sites of action in receptors, organs and systems across the human or animal body (as far as they are known and/or reported) as shown in FIG. 17.

In total, information pertaining to over 500,000 interactions associated with over 8,500 drugs (including generic drugs and prescription/trade names) are integrated and extracted from drugs' patient information labels, black box warnings and professional clinician prescription advisories. In total, in an order of 136,784 drug-disease interactions are beneficially collected. Since a same given drug exists under many proprietary market names (for example acetylsalicylic acid is sold as: Bayer Aspirin, Bayer Children's Aspirin, Bufferin, Easprin, Ecotrin, and so forth, wherein these names include trademarks), the initial database is beneficially semantically normalized in respect of an active pharmaceutical ingredient, down to a detail on a knowledge graph containing 9,526 drug-disease interactions representing interactions of 2,545 drugs' active ingredients.

Natural language processing, semantic distance and machine learning tools are beneficially also applied in embodiments of the present disclosure, for example in control apparatus, to build a semantically normalized ontology and knowledge graph of the food types (for example, in respect of broad categories such as alcoholic drinks) and food ingredients (for example, vitamin K in broccoli) for all foods. Such an ontology is then beneficially used to identify those foods and ingredients that have the potential to interact with the set of drugs as aforementioned.

Food records represented in the knowledge-graph represent a broad range of different levels of abstraction, allowing for more inclusive and flexible predictions to be made in embodiments of the present disclosure. A lower level of abstraction is represented by chemical substances, for example Potassium, vitamin K, and so forth. A middle level of abstraction is represented by simple food products, for example grapefruit juice or broccoli. A higher level of abstraction is represented by classes of food products: green leafy vegetables, dairy products, smoked meat, or aged cheese, for example.

This use of different levels of classification, namely abstraction, allows for making very broad recommendations to a given user, for example in respect of all alcoholic drinks, regardless of whether or not it is wine, beer, vodka and so forth, down to a detail of very narrow and specific components of more complex foods (for example, processed food products that contain smoked meat products and therefore have high levels of tyramine); optionally, when implemented as a control apparatus, dispensing of consumable products to users is controlled by the control apparatus. In total, there are, for example, 1,899 reported interactions between different food types and/or ingredients and drugs, and each of these interactions is stored in a knowledge graph with evidence for the interaction, for use in data processing associated with embodiments of the present disclosure.

Smart Homes

Smart homes have been proposed to enable users to live with a smaller environmental "foot-print", by causing more frugal use of finite resources (for example, electricity, fresh water, fossil fuels and so forth), as well as promoting recycling of resources. Such smart homes beneficially employ one or more control apparatus to regulate their operation, wherein the one or more control apparatus is implemented pursuant to the present disclosure.

An example application of embodiments of the present disclosure is to develop a fully personalized assisted-living Internet-of-things (IoT) solution in which the primary analysis of multi-dimensional sensor data and its interpretation for personalized decision support is delivered on an IoT Edge or Gateway device. This can be used to deploy "smart home" monitoring systems that react to the behaviors and environment of a user without requiring the user to wear a device such as a fob or smartwatch, or for their data to be continually monitored or sent to a remote data center. This removes many of the potential privacy and security issues associated with continuously monitored IoT systems, provides for more personalized and contextualized responses from the system, and reduces significantly the amount of data traffic and power required by the system. This also enables smart home systems to be smaller and more easily integrated into existing room furniture such as electrical light switches.

Behavior of users and their interaction with their environment can be highly predictive of risks and issues that may require early intervention before they become serious risks to the users' well-being. For example, falls in the home are known to be a leading cause of serious injury and/or death in elderly people. Most falls happen in the middle of the night in a bathroom when a person has woken to use toilet facilities and the person is not wearing any monitoring device. The person may be disabled or disoriented or may be immediately knocked unconscious and therefore unable to call for help. It is well known that people who fall and break a hip have a significant risk of falling into a spiral of post-operative immobility, which causes frailty, muscle loss and functional decline, which reduces their ability to care for themselves, extending hospital stays and significantly diminishing their quality of life. In two weeks prior to a fall, elderly patients tend to become slower and more deliberate in their movements, for example when rising from a chair or moving across a room. Such events can be detected and managed by control apparatus pursuant to the present disclosure.

A contemporary ASSIST project involves monitoring and interpreting a large amount of source data from sensors mounted in an electrical light switch. The sensors include one or more of: light sensors, sound sensors, temperature sensors, humidity sensors, motion sensors and home electrical current usage sensors. Moreover, a user device includes a speaker and alarm light for interaction with the user. An Array System Model (ASM) is constructed and periodically updated, using as a baseline sensor data collected from the aforesaid one or more sensors, wherein the baseline sensor data describes the user's observed normal behaviors with additional rules describing situations that require emergency intervention. The baseline may additionally include analysis of the underlying data using traditional artificial intelligence (AI) techniques such as Random Forests to identify decision trees that most closely fit an output expected in the final model (ASM). The averaged multiple decision trees output from a Random Forest method are optionally incorporated as one type of the rules and constraints that are applied to create the Array System Model (ASM).

According to an embodiment, the Array System Model is optionally loaded onto an IoT ("Internet of Things") edge or gateway device to provide a control apparatus that is configured, namely operable, to provide continuous contextualized monitoring, identifying potential emergency or non-emergency interventions required by the user, and to provide personalized decision support recommendations to users at home and their careers. If the control apparatus identifies unusual and potentially life threatening emergency situations, such as unusual patterns of prolonged immobility of a person combined with lights/appliances being on at unusual times, or dangerously low/high temperatures coupled with highly disturbed sleep patterns, the control apparatus automatically triggers an escalating series of interventions starting from initiating interactions with the user to notifying a nominated carer or third party monitoring service. Non-emergency situations such as a person slowing down and beginning to exhibit an increased risk of falling, or a lack of activity and social stimulation coupled with dysphonia (micro speech tremors—a progression marker for dementias) are detectable using the control apparatus and used to trigger notifications designing to enable prioritization of social care and home nursing responses.

In a further example of a control apparatus pursuant to the present disclosure, the control apparatus is configured, namely is operable, to apply the output of the Array System Model in the context of an ASSIST installation, which contains a personalized interpretation of an optimal response to a given situation for a specific individual, to be used as an input for a voice assistant such as Alex, Google Home or Siri: "Alex", "Google" and "Siri" are registered trade marks. Such a use of the control apparatus enables fully personalized responses to be made using a voice interface, without having to share private or medical information with a third party.

Autonomous Vehicles

Self-driving vehicles have recently been proposed as a solution to parking problems, traffic problems and pollution problems in densely populated urban environments. However, in order for a given self-drive vehicle to function safely in complex traffic situations, captured images have to very rapidly processed in real-time and control responses provide to drivetrains and steering of the self-drive vehicles. Moreover, from time-to-time, recommendations and analyses of road traffic situations have to be referred to one or more human beings being transported in the self-drive vehicles. Such data processing requires a high degree of control complexity provided by control apparatus of the present disclosure.

Thus, a further example application of embodiments of the present disclosure, namely control apparatus and their method of operation, concerns an on-device image detection and interpretation system capable of categorizing threats to self-driving or autonomous vehicles. It is impractical for such self-drive or autonomous vehicles to be in constant communications with a supercomputing data center, passing all sensor outputs and multi-modal 360° camera imagery back to be analyzed remotely and have the results sent back to the vehicle for actioning a response, for example a steering response, a braking response, an acceleration response and similar. The communications bandwidth, latency and reliability would all limit the efficacy of such an architecture. The Array System Model (AMS) is beneficially trained to perform key feature analysis is images from rules and relationship that are taught to the Array System Model.

In known contemporary development of self-drive and autonomous vehicles, there has been a focus on training neural networks using deep learning to interpret images and identify specific types of objects in scenes that describe a continuously evolving environment and trajectory experienced by the aforesaid vehicles. Such a deep learning has required developing a split computing strategy with high performance computing server farms such as NVIDIA DGX-1, training recurrent and convolutional neural networks which are then deployed onto low power, high performance specialized computing architectures such as a contemporary commercially-available NVIDIA's DRIVE PX platform, which performs huge amounts of computation on-board a given autonomous vehicle. Such an approach is currently being used singly to manage auto-cruise capability of the given autonomous vehicle, or in multiple parallel architectures to enable fully autonomous driving.

In embodiments of the present disclosure adapted for controlling self-drive and autonomous vehicles, an Array System Model is determined, which combines rules describing an identification and relevance of specific types of multi-modal features, including other vehicles, pedestrians and animals. The Array System Model is beneficially used in conjunction with other types of AI (artificial intelligence) algorithms including semantic segmentation, object detection and cascade classifiers, to identify and characterize objects of interest in a given scene presented to such self-drive and autonomous vehicles. Once identified, combinatorial trajectory mapping and forward prediction of the responses of other actor objects in the given scene are determined by the Array System Model to eliminate many irrelevant factors from the given scene. This dramatically reduces the computation effort required to be performed in self-drive and autonomous vehicles, and makes their control more accurate and much less computationally intensive. Thus, embodiments of the present disclosure are susceptible to being implemented as control apparatus for providing self-driving of autonomous vehicles, for example autonomous electric vehicles that are capable of reducing carbon dioxide emissions to atmosphere.

Drone Surveillance

A further example application of embodiments of the present disclosure concerns on-device image detection and interpretation systems capable of categorizing events in a context of surveillance applications. As above, namely mutatis mutandis as for aforementioned self-driving and autonomous vehicles, relying on transmission of all data to a remote monitoring center is highly power and data inefficient when implementing drone surveillance. A main limitation on industrial drones is their access to on-board power, and an impact that a weight of additional battery capacity has on flight time via degradation of power:weight ratio. Control apparatus pursuant to the present disclosure are therefore beneficially employed to assist in controlling flight trajectories of drones by requiring only light-weight compact computing devices to be needed.

An ability of a drone to categorize automatically a given scene and only communicate when a specific type of event is detected within the give scene is capable of enabling developers to create drones that are deployable autonomously for longer periods than is currently possible, for example for automatic surveillance purposes, for example for animal farming monitoring of herds and flocks of animals. An Array System Model pursuant to the present disclosure is susceptible to being determined, which combines rules describing an identification and relevance of specific types of multi-modal features and events, including recognition of changes to specific features of interest. The Array System Model is optionally used in conjunction with other types of AI algorithms including semantic segmentation, object detection and cascade classifiers, to identify and characterize objects of interest in the scene. Once identified and as events occur around them, the drone is optionally operable, namely configured, to submit (namely communicate externally to the drone) alerts and other information including imagery to a remote control center.

Improving drone flying time requires a very lightweight and low power computational resource on board a given drone. As a rule of thumb, every additional ounce (namely, 28 grammes) of weight requires an additional watt of power per motor on a standard quadcopter drone. As another rule of thumb, every additional gramme of weight=1 second of flight time. Even a single low power, high performance computing device such as the aforementioned NVIDIA PX weighs over 500 grammes when fully connected and consumes 10 Watts of power when in operation, which would significantly reduce the available flight time of a standard quadcopter drone, which may only weigh 1,350 grammes in total.

Even for an industrial application drone weighing 2,400 grammes, adding aforementioned NVIDIA PX data processing functionality is a significant additional weight and power burden. This additional weight and power burden would reduce the flight time of the industrial application drone to less than 20 minutes, which is impractical for effective surveillance applications. However, it will be appreciated that the Array System Model pursuant to the present disclosure for real-time on-device event recognition on a Raspberry Pi Zero™ device which weighs under 12 grammes and consumes 150 mA (0.4 W) under full computational load; "Rasberry Pi" and "Zero" are trademarks. Thus, it will be appreciated that employing a control apparatus pursuant to the present disclosure on drones provides the drones with a considerable improvement in functional performance without significantly reducing their operating flight duration.

Airborne Radar Systems

A further example implementation of the present disclosure concerns airborne radar detection and interpretation systems that are capable of categorizing a series of air and marine craft signals in a context of coastguard, customs and national border security applications. As above, relying on transmission of all data to a remote monitoring center is highly power and data inefficient and is unreliable in adverse weather scenarios. Similar power and weight considerations as described above for drones also apply to airborne radar systems, albeit to a lesser extent in this application. Thus, use of control apparatus pursuant to the present disclosure to provide increased sensor signal analysis and control response locally in airborne radar systems is technically highly beneficial with regard to weight and energy consumption.

Air and marine interdiction is a crucial part of national security, customs and border patrols. A typical radar scene for a customs and border patrol aircraft or helicopter will reveal multiple signals for planes, helicopters and boats of different types moving at different vectors and speeds around a border. Start points, predicted destinations, vessel types, registrations, timings, speeds, visibility and navigational behavior of these multiple signals are all indicative of their likelihood of being involved in various illicit activities, for example drug smuggling, illegal fishing, signal intelligence, illegal immigration, armed forces readiness testing and so forth. A typical scene will have over hundreds of craft of various types spread over a 150 kilometre (circa 100 mile) radius threat surface, some of which will be registered and have registered flight/shipping plans, and some of which will be unknown.

To optimize threat detection and elimination, there is employed a control apparatus pursuant to the present disclosure firstly to build a decision support system to characterize aforementioned craft and rank a level of threat that they appear to pose. Such an approach includes building an Array System Model which considers in real-time an aggregate risk associated with multiple factors such as registration, points of origin and destination, deviations from shipping lanes/flight plans, responses to transponder/radio hails and course/speed consistency. The system is configured to update continuously and in real-time update a threat status of each craft within a given detection range. If a vessel is observed to move out of a shipping lane, to change its course/speed or runs without identifying transponder/lights, such observations change its ranking in the decision support system.

This will likely leave tens of craft which have to be investigated at any given point in time. These craft will be moving and different speeds and in different directions through the detection volume of the customs aircraft, which will itself be moving towards and away from points of maximum risk across the threat surface. Maximizing the number and significance of the contacts that can be investigated requires a real-time optimization capability taking into account the emerging threat assessment level for a specific craft and others in the detection area. The Array System Model encompasses the multi-dimensional rules describing the threat risk posed by each target and is able to optimize object functions accounting for flight times and routes between the multiple moving targets to maximize the number and significance of threats that are directly contacted. Targets are optionally prioritized in the Array System Model; moreover, there is thereby computed a range of interventions escalating from radio contact to fly-over/fly-by or deployment of secondary resources such as support vessels to maximize the number and significance of the targets engaged during the available flight time.

Graph Traversal

A further example application of embodiments of the present disclosure is to provide a system for rapidly traversing large-scale knowledge graphs. Knowledge graphs are used to represent information mined from a variety of different data sources which, when semantically normalized, are susceptible to being recorded in a single connected graph form, with nodes representing concepts or nouns, and edges representing relationships or verbs. It will be appreciated that the system is susceptible to being employed in the aforementioned control apparatus of the present disclosure. A standard unit of conceptual connectivity is the Subject-Verb-Object (SVO) triplet, for example HIPPOCAMPUS-IS PART OF-BRAIN. In graph terms, this is equivalent to a Node-Edge-Node sub-graph; in ontological terms, this is a Subject-Predicate-Object construct. Both nodes and edges in such a graph potentially have types and multiple properties or attributes, including associated data sources in which they occur and descriptions of the evidence supporting their connection in the graph. Concepts are optionally multiply connected with colored edges, which are beneficially used to represent different relationships mined from different types of primary data source.

Current graph databases employ a variety of methods for searching paths between nodes in a graph. Broadly, these methods are "depth first" methods or "breadth first" methods. They two types of methods both rely on visiting nodes judged to be adjacent (depth first examines children nodes before neighbors, breadth first neighbors before children) and using back tracking and redundant edge elimination to produce a spanning tree that contains the connectivity paths between the starting and ending nodes. Both types of methods suffer from a characteristic that all the nodes in the graph have to be visited at least once, and potentially need to be visited multiple times. As graphs become denser (namely, the average number of edges per node increases), the computational load increases significantly. Variations of breadth first search are often used to find a shortest path between two nodes, although in larger, more connected graphs this can be a computationally expensive process.

The aforementioned Array System Model, in an embodiment of the present disclosure, is employed to build a representation of a comprehensive life science knowledge graph and to use constraints and object functions to provide very rapid searching capabilities for such large, highly connected graphs. There is thereby generated a semantically normalized knowledge graph that is used to store all of the knowledge mined from the life science literature, genomic, chemical and clinical databases, and related patent filings, regulatory filings, clinical studies and internal R&D projects. Such knowledge graphs have hundreds of millions of nodes with billions of edges and closely related pair of nodes are potentially connected by tens or even hundreds of edges. In addition to those triplet connections mined by techniques such as Natural Language Processing (NLP), Named Entity Recognition (NER) and Relationship/Information Extraction, a deep semantic learning approach is used in an embodiment of the present disclosure to identify a semantic distance between every pair of concepts in a corpus of knowledge. These semantic distances are a measure of a degree of contextual co-occurrence that any two concepts exhibit in terms of appearing always with similar words, or in similar documents. The more contextual similarity two concepts share, the smaller the semantic distance between them. It will be appreciated that such "distance" is not a real physical spatial distance, but an abstract distance that is employable in computations performed in the aforesaid control apparatus for providing technical control of real technical system.

Being able to measure a semantic distance efficiently, even for very large concept spaces with hundreds of millions of concepts, means that every concept in the knowledge graph is connected at least once to every other concept; this occurs in embodiments of the present disclosure; in contradistinction, known types of node-by-node searching tools are impracticable when processing such large amounts of information, unless certain portions of the information are ignored, which in turn negates its benefits in identifying latent connections between nodes.

Using an Array System Model pursuant to the present disclosure to represent the knowledge graph enables very rapid graph traversals that can be defined using constraints, for example when searching for nodes connected by a given edge and/or a specific intermediate node. Object functions are optionally used to reduce, for example to minimize, a cost of a given selected path, based on a summation and/or weighting of its properties.

Drug Reprofiling

Considerable investment is employed in pharmaceutical industries to develop new types of medication, for example using wet laboratories ("wet labs"), chemical analysis apparatus, assay platforms, DNA PCR sequencers (e.g. produced by Illumina Inc, Qiagen Inc. and similar), microscopes, and such like. Approaches that reduce such investment are of considerable importance to pharmaceutical companies.

Embodiments of the present disclosure provide a control apparatus, namely a system, to enable identification of candidate molecules for drug repurposing. This drug repurposing is the identification of opportunities to find new uses for drug compounds that are either already prescribed for a different disease, or which failed to receive marketing approval for reasons other than serious toxicity. Reprofiled or repurposed compounds are significantly cheaper, quicker and less risky to develop, as they have already passed many or all of the very expensive phases of clinical testing. It will be appreciated that methods of manufactured pharmaceutical compounds are the subject of many granted patents in the USA, UK and Europe (EP).

According to the pharmaceutical industry trade body PhRMA, an amount of money spent on biopharmaceutical R&D has increased from $8.4 billion in year 1990 to $186 billion in contemporary times, and yet an approval rate for new molecular entities has remaining essentially static during a period from year 1990 to contemporary times, with year 2016 being the low point with just 15 new molecular entities (small molecule drugs) being approved. This low approval rate translates to an average cost per new drug of £2.7 billion (including biologic drug approvals). An average time to bring a new drug to market is in a range of 10 to 15 years, and the average time for a new mechanism to have market exclusivity has fallen to a few months. This average time and makes the identification of new reprofiling candidates a very attractive option, both from a commercial and a patient care/treatment option perspective. For some rare and orphan diseases which do not attract R&D resources of major pharma companies, reprofiling is often an only practicable approach to find an effective drug solution to an unmet medical need.

Large and diverse datasets exist regarding licensed and/or discontinued drugs and abandoned development drug compounds which provide an opportunity to discover previously unidentified opportunities for drug development. These datasets include clinical, biological, chemical and patent data. Some of the contributing data sources (such as scientific literature and patents) are of a large scale and are semantically complex. In an example embodiment of the present disclosure, the Array System Model is used to build a representation of a comprehensive life science knowledge graph derived from aforementioned data sources and to use constraints and object functions to search for specifically defined properties of existing drug compounds that mark them as good reprofiling opportunities. Such constraints draw upon both symbolic and sub-symbolic aspects of the underlying knowledge graph, with both logical/linguistic relationships, and underlying contextual semantic distances between concepts being represented in the same graph. The Array System Model is used to identify drug molecules originally approved for different disease indications, that share activity against a series of common proteins and receptors, but where the direct activity of one on the specific receptor or pathway of the other, which is known to be a druggable intervention point in a different disease, has not been reported in the literature. The Array System Model's ability to traverse very large scale, highly connected graphs provides a much faster method to identify such latent similarities. The Array System Model is thus employed in combination with known biological drug characterization methods employing biological samples and analytical apparatus for processing and characterizing the samples, to provide an output from the Array System Model that is indicative of alternative uses for the drugs; the Array System Model is therefore to be regarded as a part of a chemical analysis system, wherein chemical analysis systems have earlier been the subject matter of many granted patents in US, UK and Europe (EP).

Precision Agriculture

A further example application of embodiments of the present disclosure is to provide a system to support crop and livestock yield improvement by integrating and exploiting plant and livestock phenotypic and multi-omics data with real-time IoT ("Internet of Things") sensor and imaging data feeds. Yield improvements in agriculture is a strategically important area of unmet need, wherein optimizing a combination of inputs (for example, fertilizer), treatments (for example, herbicides, insecticides), doses (for example, quantities of insecticide administered) and timings (for example, duration between application of insecticides) to apply to specific crop strains or specific livestock breeds at a given point of their growth process in a context of a specific series of environmental conditions is a massively complex computational challenge. The control apparatus of the present disclosure is capable to addressing this computational challenge, wherein output from the control apparatus can be used to control application of fertilizer, herbicides, insecticides, harvesting methods and timing of such technical activities. Moreover, the control apparatus is susceptible to being used in greenhouses, hydroponics facilities and similar, for example for improved production of tomatoes, vegetables, as well as cannabis and tobacco in parts of the World where cannabis and tobacco production is legal.

It is contemporarily appreciated, for example by the United Nations (UN) and other international cultural and humanitarian organizations, as well as governments around the World, that there is a grand societal challenge to intensify the World's food production in a sustainable manner. Moreover, it is also appreciated, that despite efforts to deploy renewable energy systems, that a very major source of energy for industrially developed nations is fossil fuel, namely coal, oil and gas. This fossil fuel is becoming increasingly expensive as a function of passing time, as easy-to-access fossil fuel resources are becoming depleted, for example the Ghawar oil field in the Middle East, North Sea oil, Texan oil, and so forth. Such fossil fuels provide a basis for fertilizer production, irrigation, food transport, food storage and food processing, as well as ensuring clean water and sanitation. The world population is presently circa 7.6 billion people and increasing towards 9.5 billion people by year 2050, despite the aforementioned depletion of energy resources. Ultimately, without new sustainable energy technologies being deployed, human population will eventually fall, potentially in a chaotic manner, as pollution, disease, famine, political instability, and anthropogenically-forced climate change cause diminution of the World's life-supporting capabilities.

Given population growth and demographic change, it is widely accepted that there is a contemporary need at least to double the output of food production by year 2050, using the same basic inputs of land, water, power and chemicals. Food production and distribution already accounts for 30% of all power generated, 50% of the viable land area and 70% of the fresh water abstracted across the planet Earth. Moreover, food production also generates about 33% of the World's greenhouse gas emissions that are linked to aforementioned anthropogenically-forced climate change.

In an embodiment of the present disclosure, the Array System Model employed in a control apparatus is used to build a representation of a semantic knowledge graph of crop strains, traits (both genomic variant and from integrated non-destructive phenotyping technologies), yields, soil conditions and wider growing environment including remote sensing data. This knowledge model can be deployed as a mobile tablet software application (namely, "app") with a simple decision support a user interface (UI) to allow non-IT specialist growers to identify specific combinations of treatments that enable them to optimize crop yields and to reduce, for example to minimize, wastage of inputs to agricultural activities. Alternatively, the Array System Model employed in a control apparatus pursuant to the present disclosure is used to build a representation of a semantic knowledge graph which, for example in livestock management, includes livestock pedigree information, genomic sequencing and continuous phenotypic monitoring data with real-time sensors for sensing animal food and water take up, animal behaviour, animal activity/movement, animal weight, animal disease history, animal medicines usage, environmental factors affecting animals and so forth correlated to output metrics including milk/meat yields, fertility, disease resistance; thus, the control apparatus is susceptible to being used to monitor output of an agricultural growth system, and also to control inputs to the agricultural growth system to enhance its technical performance, namely output yield and/or resource utilization (in other, an operating efficiency of the agricultural growth system). A knowledge model allows a given farmer to plan in real-time best interventions for a particular animal in terms of changes to feed and or animal environment to improve yield, and also the best breeding plan for longer term management of a given herd of animals. Moreover, embodiments of the present disclosure used to optimize conditions of livestock is highly beneficial for animal welfare.

Disease Risk Scoring

The aforesaid control apparatus of the present disclosure is susceptible to being used to provide a system to develop clinical decision support tools that apply complex multi-feature biomarkers clusters based on combinations of genomic, phenotypic and clinical data, to enable stratification of patients for disease risk scoring and personalization of lifestyle and dietary advice on mobile devices. Thus, the control apparatus is capable of being used in combination with other technical apparatus of health care establishments.

According to an example embodiment of the present disclosure, the aforesaid Array System Model employed in an aforementioned control apparatus is capable of providing a clinical decision support and personalized advice platform based on a given patient's specific combinations of biomarkers, to help clinicians to understand and respond better to the given patient's individual disease risks, in real-time at a point of care to the given patient. Moreover, the Array System Model also potentially gives patients tools that they can use themselves in their community to understand and manage their health and to reduce, for example to minimize, one or more avoidable side effects of therapy. Thus, embodiments of the present disclosure provided systems and apparatus for administering health care.

The Array System Model is susceptible to being used to provide patient stratification tools applying previously identified biomarkers clusters that are based on unprecedentedly broad combinations of genomic, phenotypic and clinical factors. Moreover, the Array System Model is further configured to use these clusters to build clinical decision support tools for disease risk scoring and personalization of prescription and dietary advice on mobile devices at a point of care or in a community. These tools enable clinicians to provide personalized advice to healthy individuals to make manageable changes to specific aspects of their lifestyle, for example exercise regimen, screening frequency or sleep patterns, and to diet that will reduce their likelihood of contracting the disease.

The Array System Model is built using data from patient populations enrolled in existing multi-omic studies (for example, a 42,000 asthma mutant population from the UK Biobank study and 17,500 patients from the Project MinE MND/ALS study). The clinical decision support tools use the Array System Model to calculate a cumulative disease risk arising from multiple networks of features previously identified to be associated with higher or lower disease risk in the patient population. This Array System Model exploits the previously identified associations between combinations of multiple (up to 17) multi-omic factors, which are highly predictive of disease risk and disease protective effects, and which are more specific than existing single/twin gene tests, for example BRCAI/2.

For patients at risk of developing a specific disease, embodiments of the present disclosure provide a control apparatus to deliver personal dietary advice to a given user based on an Array System Model that includes specific genomic and pharmacogenetic information of the user coupled with the aforesaid knowledge graph to provide personalized lifestyle and dietary advice. This control apparatus enables, for example, breast cancer patients to ameliorate the impacts of radio-, chemo- and hormone therapy, specifically advising them how to avoid food and lifestyle interactions with their diseases, drugs and their other pharmacogenetic and nutrigenomic predispositions. Moreover, the control apparatus enables patients to check food choices in a supermarket, restaurant or at home for likely interactions, and so reduce, for example minimize, side effects during treatment. Furthermore, such advice will help them maintain compliance with a given prescribed therapeutic regimen, which is known to significantly increase their outcome prospects.

Point of Sale Pricing

The aforementioned control apparatus of the present disclosure is susceptible to being configured to provide a sales system to personalize pricing of products and services, and offering of incentives to individual shoppers in a given store. Recent developments in point-of-purchase (POP) displays have enabled retailers to move away from single pricing for items to adaptive pricing systems, wherein prices are adjusted adaptively throughout a time period of a day or a week, or even offer personalized offers to specific customers as they move through the given store, based upon their previous purchase history. Such an embodiment is not a method of doing business as such, but a retailing system that is capable of providing an improved experience to shoppers.

The aforesaid retailing system beneficially employs electronic shelf displays and price labelling systems coupled with Bluetooth Low Energy (BLE) and RFID technologies for enabling a hyper-localization of goods, services and offers to consumers, as the customers come into a vicinity of the given store, or even as they walk around the given store. Such hyper-localization of goods, services and offers to consumers optionally takes a form of sending a given customer a voucher for an offer with a very time-limited expiry, or printing a discount voucher at the point that the customer selects a given item from a shelf of the given store.

Optimizing the returns from rewards/loyalty programmes and personalized offers in real-time as customers arrive at and move around a retail environment requires a complex decision support system that can intersect a model of the customer's previous purchasing history and their responses to previous offers with knowledge of the store's current stock levels and the margins associated with specific products. The Array System Model of the present disclosure can be used in a control apparatus to build a complex decision support system that optimises the likely yield of an offer or incentive in terms of customer loyalty, short-term spend and overall store margin, using object functions to optimise returns in the knowledge of contextual factors such as potential wastage of short shelf-life products, such as cream cakes, perishable fruit and similar.

Referring next to FIG. 37, there is shown a schematic diagram of a welfare system 4000 that is configured to provide welfare support to a plurality of individuals in an assistive environment; for example, the assistive environment pertains to animals in a farming and veterinary environment, alternatively people within care homes, hospitals and the like, in accordance with an embodiment of the present disclosure. The welfare system 4000 comprises a data processing arrangement 4002, a sensor arrangement 4004 and a decision support knowledge model 4006; the data processing arrangement 4002, the sensor arrangement 4004 and the decision support knowledge model 4006 operate synergistically together to provide an enhanced quality of life for the individuals. As will be described in more detail later, the welfare system 4000 employs the aforesaid PACE engine that is configured to implement methods as described in the foregoing to generate the aforesaid Array System Model (ASM); the PACE engine is configured to receive sensor and measurement signals (for example gene variant information, environmental sensor data, individual food data, individual measurement data) and to provide outputs for controlling the welfare system 4000 to deliver enhanced welfare support. The welfare system 4000 also utilizes a MARKERS model and ANNOTATION model that will be described in greater detail later. Such a PACE engine, a MARKERS model (used interchangeably as "MARKERS engine") and an ANNOTATION model (used interchangeably as "ANNOTATION engine") can form a part of, and operate collaboratively with each other, under a "Precisionlife platform". Consequently, when the ANNOTATION model forms a part of the Precisionlife platform, for example, the ANNOTATION model has been referred to as "Precisionlife Data Annotation Platform".

The MARKERS model and the ANNOTATION model are derived from the aforesaid array system model (ASM) and utilize deduction derived from the array system model. The aforesaid MARKERS engine is used to perform mining within a pre-filtered dataset to find distinct n-combinations of SNP genotypes and/or other types of features found in a given individual animal that can be used as an input to the ASM.

The welfare system 4000 refers to a system that is configured to perform a targeted and contextualized decision support (using the aforesaid PACE engine) for a plurality of individuals under consideration. The welfare system 4000 prepares the targeted decision support based on one or more genotypes of the plurality of individuals under consideration, and any relevant polymorphism determined via Single Nucleotide Polymorphism (SNP) thereof. The welfare system 4000 monitors the growth process of the plurality of individuals under consideration in order to provide the plurality of individuals with improved welfare, for example optimal welfare (for example, adapting support to the plurality of individuals in a customized manner that addresses special needs of each individual within the plurality of individuals under consideration, that may vary from one individual to another (for example, certain individuals may have disease susceptibilities or anatomical features such as weak feet or legs that requires special attention, other conditions causing the certain individuals discomfort and pain, requiring administration of food supplements such as glucosamine)). Furthermore, the welfare system 4000 utilizes methods for (namely methods of) using a knowledge of variants in a given individual to design an optimal therapeutic intervention specifically customized to the given patient individual. The welfare system 4000 includes a high-order combinatorial search (using the aforesaid PACE engine) within the decision support knowledge model 4006 is based upon the plurality of measurands derived from a given individual's variants, for example, using the sensor arrangement 4004. By "high-order" is meant at least an order 3, more optionally at least an order 8, yet more optionally at least an order 20, and yet more optionally at least an order 50 (if input datasets allow for such a high-order as 50). For example, the combinatorial search is performed to find all significantly associated combinations in a hypothesis-free manner. Such a finding of all associated combinations does not relate to pre-selection of specific pathways/genes. A detailed explanation for what is meant by "high-order" is provided herein later. The welfare system 4000 is further configured to evaluate an optimal support regime for each individual in the plurality of individuals under consideration and to plan a support trajectory for each of the individuals in the plurality of individuals under consideration. Furthermore, the plurality of individuals under consideration belong to the assistive environment, namely are hosted in the assistive environment. The assistive environment may be, in a case of animals, a farm with farmhouse and outbuildings, a cattle breeding farm or any area used for keeping and breeding of the plurality of individuals under consideration. In a case of humans, the assistive environment may be a care home, a hospital, a domestic caring home environment, a clinical facility and the like. Optionally, the combinatorial analysis is performed to identify combinations of features that are predictive of specific phenotypes and a combination of features associated with a variety of responses to particular diets and/or environment. Thereafter, the combinations of features are employed to derive combinatorial risk scores and the features as well as the risk scores will form one of the inputs to the PACE engine, alternatively to the aforesaid ANNOTATION engine. Optionally, other constraints and data can be incorporated into the PACE engine as well, such as, IoT and environmental data, in order to further optimize and personalize the predictions and decision support recommendations.

Furthermore, the welfare system 4000 includes the data processing arrangement 4002 (using the aforesaid PACE engine) that is configured to receive sensor signals from the sensor arrangement 4004 that is spatially distributed within the assistive environment. Furthermore, the data processing arrangement 4002 is configured to process (using the aforesaid PACE engine) the received sensor signals. Additionally, optionally, the data processing arrangement 4002 is an arrangement of Internet-compatible devices having data processing capabilities, that are mutually coupled together via a data communication network. Notably, the data processing arrangement 4002 constitutes a powerful computing engine arrangement (for example using the aforesaid PACE engine) that facilitates performing real-time data processing for provision of individualized support (namely, customized support) to individuals in the assistive environment. The data processing arrangement 4002 may be a software, hardware, firmware or a combination thereof, for example custom-designed digital hardware. The data processing arrangement 4002 may include one or more processors connected to each other in any architecture such as parallel or pipelined. In an example, the data processing arrangement 4002 may include a communication module for receiving sensor signals from the plurality of sensors. Furthermore, the sensor arrangement 4004 is configured to sense environmental conditions for each individual, including monitoring a food intake for each individual. Additionally, sensor arrangement 4004 is an arrangement of Internet-compatible devices having sensing capabilities. The sensor arrangement 4004 is configured to sense environmental conditions experienced by each individual, including monitoring a food intake for each individual, spatial movement of each individual, a temperature of each individual, a water intake of each individual. Examples of the environmental conditions include, but are not limited to, temperature within the assistive environment, humidity within the assistive environment, sunlight exposure within the assistive environment, air quality within the assistive environment, and chemical exposure within the assistive environment. In an example, the plurality of sensors include cameras to view the plurality of individuals under consideration (skin, face, manner of movement, sleeping pattern and posture, temperature sensors, humidity sensor, sunlight exposure sensors in individual housings, such as, via wireless tags attached to animals or humans, food intake monitoring sensors (e.g. from mechanized feeding trays), gas sensors (such as Carbon Dioxide $CO_2$, methane $CH_4$, Hydrogen Sulphide HS, and the like) and light exposure monitoring sensors (e.g. individual tags worn on animals or humans). Specifically, humidity sensors are implemented as thin-film polyamide sensors, temperature sensors are implemented as thermistor or integrated-circuit solid-state temperature sensors (for example as temperature sensors housed in injection-moulded plastic tags (namely, animal tags or human tags) that can be attached to each of the plurality of individuals, to food troughs, to water troughs, to barriers between animal pens, to doors and gates of individual pens, suspended from a roof/ceiling). The animal tags, likewise the human tags, have network connectivity with a peer-to-peer network communication around the assistive environment, wherein, due to movement of any of the plurality of animals or humans, the peer-to-peer network is dynamically reconfigurable (for example, by using a calibration routine periodically around the peer-to-peer network based on signal strength to find principal Eigenvector routes of communication). Air-flow sensors in the animal environment are beneficially implemented as heated wire pair transducers or thermistor pair transducers. Optionally, there is employed Internet of Things (IoT) technology, for implementing a data communication network using standard proprietary commercially available communication devices. Moreover, the plurality of sensors in the sensor arrangement 4004 are positioned deterministically or randomly within the assistive environment. Additionally, the plurality of sensors is positioned in a way to achieve maximum coverage of the assistive environment. Moreover, the positioning of the plurality of sensors in the sensor arrangement 4004 is implemented in a way to achieve a maximum connectivity therebetween. At an example, the plurality of sensors may communicate with each other to communicate the sensor signals to the data processing arrangement 4002. In another example embodiment, the plurality of sensors may communicate the sensor signals to a base station that may further aggregate the sensor signals received form the plurality of sensors to the data processing arrangement 4002.

The data processing arrangement 4002 includes the decision support knowledge model 4006 (for example using the aforesaid PACE engine, the MARKERS engine or the ANNOTATION engine) against which the sensor signals are compared. The decision support knowledge model 4006 is populated with at least one of drug characteristics, food supplement characteristics, husbandry strategies depending on individual health complications, disease characteristics of each individual, individual genotype data, and SNP data. Moreover, the decision support knowledge model 4006 includes genotype information, potential diets, potential medications, medication list, food supplement list and the like to be followed for each of the plurality of individuals under consideration. The sensor signals compared with the decision support knowledge model 4006 provide details for targeted precision support for each of the individuals in the plurality of individuals under consideration. Additionally, data gathered for each of the individuals in the plurality of individuals by the sensor arrangement 4006 allows for the decision support knowledge model 4006 to be iteratively updated. Beneficially, the welfare system is capable of learning from past experiences derived from gathered and archived data related to phenotypic data, genotypic data like single nucleotide polymorphism associated with the plurality of individuals under consideration, environmental data, food intake data, drug interventions and so forth. Optionally, the decision support knowledge model 4006 uses artificial intelligence (AI) algorithms for monitoring individual behaviour of each individual and its habits, thereby developing a corresponding model characterizing each individual, and then identifying deviations from the corresponding model characterizing each individual that are potential indicative when each individual is any manner uncomfortable (for example, stressed or unable to achieve expected outcome metrics), distressed or ill. In an event that a given individual has deteriorating wellbeing, the welfare system 4000 initiates care measures to assist the given individual achieve an improved state of wellbeing.

Optionally, the SNP data includes single nucleotide polymorphism characterizing each individual, determined by using microarrays, DNA sequencing, CRISPR tests or Polymerase Chain Reaction (PCR) to read genetic tissue samples derived for each individual. The term "single nucleotide polymorphisms" (SNPs) relates to genetic variations among a given species of the individuals. Notably, such single nucleotide polymorphisms are identified upon analysis of DNA sequences of the given individuals, wherein each single nucleotide polymorphism represents a variation in a single nucleotide within DNA sequences of different members of the given individuals. It will be appreciated that the genetic tissue samples derived for each of the individuals allow for obtaining DNA sequences for each of the individuals, wherefrom, the single nucleotide polymorphisms characterizing each individual (namely, phenotypes of the individuals) are determined by using microarrays, DNA sequencing, CRISPR tests or Polymerase Chain Reaction (PCR). Furthermore, Polymerase Chain Reaction (PCR) is a molecular biology technique that allows for amplification of a segment of a given DNA sequence across several orders of magnitude whilst making multiple copies of the segment of the given DNA sequence. Optionally, such SNP data is obtained in respect of embryos (for example from corresponding blastocysts) for selecting embryos that will give rise to desired phenotype characteristics, wherein selected embryos are subsequently implanted using IVF to generate individuals with preferred phenotype characteristics; such an approach avoids a need to generate individuals with undesirable phenotype characteristics and thus enables the welfare system 4000 to operate more efficiently by needing to support only desired individuals. Alternatively, the SNP data is obtained for identification of elite parents for selective breeding of offspring. For example, the SNP data is obtained for optimized selective breeding, such as, for reducing a generational interval and optimizing for multiple traits simultaneously. Furthermore, the selection criteria can include non-genomic criteria such as epigenetic factors, expression levels, and so forth, as well as diversity in part, as indicated by pedigree of animals.

The welfare system 4000 is configured to develop a personalized identification of one or more active drug combinations for the treatment or prevention of a given individual's specific disease, in accordance with an embodiment of the present disclosure. The welfare system 4000 includes the data processing arrangement 4002 (that employs the aforesaid PACE engine) that receives a plurality of measurands of the given individual from the sensor arrangement 4004 and accesses the decision support model 4006 including a plurality of treatment strategies and genomic data.

The welfare system 4000 is configured to use the patient individual's SNP genotypes and/or one or more other features which synergistically affect traits (such as, disease status associated with humans and animals; yield, food conversion, fertility, milk quality and so forth associated with animals) as a part of the measurands obtained using the sensor arrangement 4004. It will be appreciated that a same disease can be caused due to presence of a plurality of different SNPs. Furthermore, individuals having the disease may share a number of SNPs therebetween. Moreover, such individuals can correspond to one or more common features, such as one or more phenotypic features, clinical features, lifestyle features and so forth. In such an example, the welfare system 4000 is configured to use the patient individual's SNP genotypes and/or one or more other features (such as, epigenetic factors, epidemiologic factors, environmental factors or a combination thereof) which synergistically affect the disease status as part of the measurands. Optionally, the welfare system 4000 comprises a single-nucleotide polymorphism (referred to as "SNP" hereinafter) genotyping device (such as, implemented as part of the sensor arrangement 4004) that is capable of determining SNP genotypes within a population. Such a SNP genotyping device can use one or more SNP genotyping techniques for the determination of the SNP genotypes, including but not limited to, hybridization-based techniques such as SNP microarrays, enzyme-based techniques such as PCR-based techniques, or next generation sequencing (NGS) techniques such as temperature gradient gel electrophoresis (TGGE), which are performed over a wide and non-biased selection of SNP samples. Optionally, the SNP genotyping device is also capable of determining one or more additional features associated with the SNPs within the population. The features associated with the SNPs are obtained from performing DNA base readout from biological samples. In an example, the DNA base readout from the biological samples is performed as part of a Genome-Wide Association Study (referred to as "GWAS" hereinafter).

In another example, SNP-genotyping arrays are used to identify the features associated with a given population of individuals. Such an SNP-genotyping array can perform SNP genotyping for tens of thousands of individuals (patient individuals and healthy individuals). The SNP-genotyping array is used as a part of a canine genomic study, to identify novel clusters (signatures) comprising disease-causing mutations (in developmental as well as adult stages) corresponding to chondrodysplasia within a population of 1,600 canines (120 breeds). The SNP-genotyping array used is a CanineHD array by Illumina® (alternatively, very highly enriched signals can be used for accurate risk scoring and/or diagnosis for individuals, to determine a best intervention strategy), the array corresponding to anonymised 150,000 SNPs. Correspondingly, it can be identified that 90% of cases contain a top 30 signature (representing a total of 985 SNPs) while a 98% of cases contain a top 100 signature (representing a total of 1,500 SNPs). Furthermore, the SNP-genotyping arrays are available in multiplex formats for huge throughput. Moreover, the features of the one or more SNPs are stored in the decision support knowledge model 4006. Furthermore, the biological samples are collected from a plurality of patient individuals suffering from a specific disease or disorder and a plurality of as healthy individuals not suffering from the specific disease or disorder. The measurands obtained from performing the DNA base readout of the biological samples comprise information about SNP genotypes and features associated with the SNPs for the plurality of patient individuals and the plurality of healthy individuals. In one embodiment, the features associated with a given population of individuals are identified using quantitative trait association, outlier comparison, non-diploid genotypes, and so forth.

Furthermore, the data processing arrangement 4002 is configured to generate data (using the aforesaid MARKERS engine) by using the measurands obtained via the sensor arrangement 4004. Such data generated from the measurands is stored in the decision support knowledge model 4006 as data files. In an example, the data files comprise the measurands in a structured format (such as a table), wherein the measurands comprise an individual identifier, a CC vector, SNP genotypes and SNP identifiers (referred to as "SNPid" hereinafter). In one example, the CC vector can have a value of '0' when the individual is the patient individual suffering from the specific disease or disorder, or a value of '1' when the individual is the healthy individual not suffering from the specific disease or disorder. In an example, the SNP genotype can take a value of '0' when the SNP genotype is a homozygous major (or normal) allele, a value of '1' when the SNP genotype is a heterozygous allele, a value of '2' when the SNP genotype is a homozygous minor (or variant) allele, or a value of '3' when the SNP genotype is unknown. In one example, the SNPid can comprise information about the SNP, such as an index or "rs number" of the SNP. In an example, the SNP genotype and the SNPid can be stored together in a form of tuples comprising the index of the SNP and the genotype of the SNP. In such an example, when the index of the SNP is 247 and the SNP is associated with a homozygous major allele genotype, the SNP genotype and the SNPid can be stored together as $247^0$, wherein the index 247 of the SNP can be associated with an rs number such as rs12345678. Thus, the data for each of the plurality of patient individuals and/or healthy individuals can be stored in a structured format as a CC vector of the individual, followed by the tuples comprising the index of the SNP and the genotype of the SNP. In one example, when a patient individual corresponds to an individual identifier of number 27, the data can be expressed as:

Case #27 1 $1^0$ $2^0$ $3^1$ $4^0$ $5^2$ $6^1$ . . . $n^k$

The data processing arrangement 4002 is configured to execute (using the aforesaid PACE engine) a high-order combinatorial search within the decision support knowledge model 4006 based upon the plurality of measurands obtained using the sensor arrangement 4004. The data processing arrangement 4002 is configured to receive the plurality of measurands of the given patient individual and the plurality of treatment strategies and genomic data from the decision support knowledge model 4006 and to perform processing thereon (as described in detail hereinafter).

Optionally, the data processing arrangement 4002 is configured to use a computational engine (namely, the aforesaid "PACE engine") with combinatorial methodology that is used for combinatorial feature analysis. The combinatorial feature analysis may take into account epistatic interactions between various genetic and non-genetic factors. The term "epistatic interaction" as used herein, refers to combinations of multiple features in a gene, such as SNP genotypes, affecting phenotypes in another allele in a reproducible but non-linear additive manner. The term "phenotype" used herein, relates to physical traits, diseases, disease-associated factors, disease risk, therapy response and so forth. In an example, the patient individuals are associated with cancer or mutation. In such an example, a number of patient individuals corresponding to specific phenotypes are selected and high-order combinations of the patient individuals' SNP genotypes are identified. It will be appreciated that such SNP genotypes will be present in a plurality of patient individuals but absent in a plurality of healthy individuals (It will be appreciated that in late-onset diseases, there may be many young controls who share the genotypic features that will increase their eventual disease risk, but who have not encountered sufficient sporadic mutations or environmental factors to cause them to develop the disease). Furthermore, such SNP genotypes are determined to be disease-associated SNP genotypes and thus, such SNP genotypes are considered for further testing and validation by the welfare system 4000.

Optionally, the welfare system 4000 is configured to analyse the patient individual's entire genome and structural variants from a patient individual's disease biopsy provided as measurands to the data processing arrangement 4002. The patient individual's entire genome is analysed using standard techniques comprising at least one of: Sanger sequencing (followed by linkage analysis and autogyzosity mapping), DNA microarrays, next generation sequencing (NGS) techniques, genome-wide association study (GWAS), whole exome sequencing (WES) and analysis and the like. The analysis of the patient individual's entire genome enables to identify measurands within a population, such as SNPs, SNP genotypes, features associated with a phenotype and so forth, for conducting association studies or testing for future disease risk, prevention and treatment. It will be appreciated that exome data may only have a small subset (such as, less than 2%) of features that are disease-associated. Consequently, gene expression control features are more heavily involved than coding region mutations in most complex traits and chronic diseases.

The patient individual's disease-associated SNPs can be obtained by performing a biopsy for the patient individual. Alternatively, the patient individual's disease-associated SNPs can be obtained from a DNA-containing sample, such as blood, skin tissue, amniotic fluid, buccal swab, hair, saliva, faeces and so forth. The term "biopsy" as used herein, refers to a technique of removing a small tissue sample (such as a tumour) using a needle, or by surgical removal of a suspicious lump or nodule from a site of biopsy. Optionally, imaging guidance by employing X-ray, ultrasound, magnetic resonance imaging (MRI), computed tomography (CT or CAT) and so forth, allows for accurate placement of the needle (or other surgical equipment) to locate the site of biopsy. Subsequently, upon location of the site of biopsy, a small incision is made at the skin around the site and the needle is inserted, to remove the tissue sample therefrom. Optionally, the biopsy can be performed by employing a technique such as, fine-needle biopsy, core-needle biopsy, vacuum-assisted biopsy and the like. More optionally, the biopsy is performed automatically by the sensor arrangement 4004. Thereafter, at an end of the biopsy, the site of biopsy is covered with a dressing or bandage. The welfare system 4000 provides the patient individual's biopsy as measurands to the data processing arrangement 4002. Subsequently, the data processing arrangement 4002 determines an outcome by executing computations on the measurands. For example, the data processing arrangement 4002 is given the measurands comprising two or more SNP genotypes and the outcome from computations executed by the data processing arrangement 4002 includes at least one specific phenotype. In such an example, the phenotype can be a disease caused by at least one of the two or more SNP genotypes. Optionally, the data processing arrangement 4002 finds from the specific phenotype, one or more causal SNP genotypes associated with various other genes that may cause the disease.

Optionally, the data processing arrangement 4002 is configured (using the aforementioned PACE engine) to find high-order combinations of SNP genotypes which synergistically affect a disease status of an individual. Furthermore, such SNP genotypes can be stored by the data processing arrangement 4002 within a database (not shown) communicatively coupled with the data processing arrangement 4002, to be used as input measurands at a later time.

The welfare system 4000 is further configured to capture a disease network pertaining to the patient individual's entire genome. It will be appreciated that a large number of genes are associated with disease risk, and identification of the genes along with their association to other related pathways is essential for analysing the patient individual's entire genome. For example, when one or more SNPs result in formation of malignant tumours, the welfare system 4000 identifies the SNPs associated with the formation of the tumours.

Furthermore, apart from the genetic factors (such as SNPs), non-genetic factors influence a patient's disease risk. Such non-genetic factors comprise one or more of: non-coding variants, biological insights, metabolic pathways, lifestyle (such as diet, sleep, physical activity and the like), clinical information (such as existing diseases, diagnostic results like imaging, assays and the like), phenotypic information (such as age, sex, race, weight, comorbidities) and so forth. In such an example, the welfare system 4000 captures the disease network comprising a network of causal genetic factors (such as SNPs) and non-genetic factors (such as lifestyle).

Optionally, the welfare system 4000 configured to identify a treatment for a disease that is selected from a group including: metabolic, cancer, cardiovascular, respiratory, neurodegenerative, neuropsychiatric, autoimmune, immunological, inflammatory and respiratory disease. In an example, the disease is type-II diabetes.

The welfare system 4000 (using the aforesaid PACE engine) is configured to identify a course of treatment to be prescribed to the patient individual. Optionally, the treatment is based upon the patient individual's SNP genotype and at least one non-genomic feature of the patient individual. It will be appreciated that conventional treatments for treating complex diseases such as, metabolic, cancer, cardiovascular, respiratory, neurodegenerative, neuropsychiatric, autoimmune, immunological, inflammatory and respiratory diseases and so forth, include prescribing drugs for the specific disease, without taking into account the combination of the genetic and non-genetic (such as phenotypic) factors that may vary for each patient individual. The welfare system 4000 identifies the course of treatment for such complex diseases by considering the combination of the genetic (SNPs) and non-genetic (such as phenotypic) factors for a given patient individual. It will be appreciated that such a consideration of the combination of the genetic (SNPs) and non-genetic (such as phenotypic) factors enables development of personalized treatment regimens that are specific to individual patient individuals. Such personalized treatment regimens enable improved treatment of diseases, such as, by targeting multiple diseases affecting the patient individuals, by reducing undesired effects (such as side-effects, allergies and so forth) experienced by the patient individuals, by improving an efficacy of a medication for the patient individuals, by prescribing improved treatment schedules for the patient individuals, by prescribing alternative treatments or therapies for the patient individuals and so forth. Furthermore, genes whose expressions are associated with specific SNPs may be good drug targets for treating a disease. Specifically, one or more proteins associated with expression from the gene can be the drug target for treating the disease.

In such an example, the data processing arrangement 4002 is configured to determine a homology of the protein to one or more known drug targets, such as kinases, receptors, proteases, and so forth, or already established experimentally with various level of confidence in vitro, or for existing drugs, through their mechanism of action. Furthermore, the drug targets determined to have homology to the protein can be used for treatment of the disease of the patient individual.

Optionally, the treatment is a combination of active drugs. For example, the treatment of cancer comprises a combination of cancer-related and non-related drugs that target multiple nodes in the tumour-growth network. Furthermore, the data processing arrangement 4002 (using the aforesaid PACE engine) provides output signals that control operation of the assistive environment. The output signals determine action to be taken in order to provide customized welfare to each of the individuals in the plurality of individuals under consideration. In an example, for an input sensor signal indicating digestion problems of a specific individual, an output signal may be generated by the data processing arrangement 4002 directing a required medication and diet as the prescribed treatment for the individual with digestion problems.

The prescribed treatment is administered to the patient individual by the welfare system 4000. The prescribed treatment comprises one or more active drugs, a dosage level of active drugs, a frequency of doses, a mode of delivery (such as injection into muscles, intravenous, intra-arterial, intraperitoneal, topically, orally and so forth) and time period of treatment, and so forth. Furthermore, the prescribed treatment is specific to an individual and is designed based on the genetic factors and/or non-genetic factors associated with the specific disease. For example, the welfare system 4000 determines an ideal frequency of doses, such that, the doses are administered to achieve the desired patient individual care but an interval between successive doses is long enough to reduce a toxicity associated with the doses.

In an embodiment, the treatment prescribed to the individual is optimized in an on-going, such as in an iterative manner, by the welfare system 4000. For example, an optimal treatment for a 2-day old chick will be very different than an optimal treatment for a 30-day old broiler going into final finishing. Furthermore, optimization within an assistive environment involves providing each individual with optimum conditions for healthy growth within constraints of underlying genomic factors, epigenetic factors, microbiomic makeup, environmental factors, diet and husbandry protocol in which the assistive environment is managed. Such conditions will depend on changing combinations of a wide variety of factors at various points during the individual's (such as, an animal's) regular growth cycle and in response to unexpected events such as disease or a failure to thrive. Furthermore, a modern assistive environment (such as, an animal production environment) will include molecular characterization of livestock animals either by direct testing, or pedigree information from elite seedstock parents. Furthermore, additional data is collected from sensor-based equipment that measures a type and amount of food and water consumed by the animals identified using RFID tags on a real-time continuous basis. Such animals are further automatically monitored for weight, activity, gait and other diagnostic behaviors.

It will be appreciated that an optimum strategy for production of animals is to achieve a target weight, composition and conformation consistent with their genetics, with a minimum number of inputs. Such a strategy typically has multiple benefits, including minimization of costs and environmental impact of raising animals (as food efficient individual produce less methane), and improving welfare (as healthier animals are less stressed). Moreover, it is not possible for a human operator (personnel) to monitor and control the amount of food, water and the incorporation of supplements, medicines and other inputs for each individual in real-time. This results in inefficiencies that manifest as sub-optimal economic performance of the animal production environment and reduced welfare of the animals hosted therein.

The data processing arrangement 4002 is capable of using data gathered from equipment in the animal production environment (such as stalls, milking machines, food/drink weigh stations and the like) with pre-existing knowledge of molecular makeup of each animal and behavioral monitoring sensors (including sensors for measuring gait, activity, location and so forth). Consequently, when an animal interacts with a sensor (for example, on a milking machine), data are collected, for example on milk yield and milk quality. These real-time individual specific data are provided with historical baselines as input to the data processing arrangement 4002. The data processing arrangement 4002 identifies the performance of the animal and compares against its personal target and if adjustment in diet is required, sends a signal to the food bins to adjust the volume and ratio of high-low protein/calcium foodstuff to be fed to the animal.

Specifically, the data processing arrangement 4002 executes the software product (using the aforesaid PACE engine) that, when executed on data processing hardware, analyses the sensor signals obtained using the sensor arrangement 4004 in respect of the decision support knowledge model 4006 and generates the output signals. The software product is configured to accept the sensor signals as an input and analyse the sensor signals against the decision support knowledge model 4006. Moreover, the software product (using the aforesaid PACE engine) is configured to take into account various phenotypic factors affecting the plurality of individuals for providing output signals that control welfare of each of the plurality of individuals and conditions in the assistive environment. In an example, as an input to the software product, microbial pathogens found in a farming and veterinary environment are DNA sequenced and an analysis of pathogen type is determined by comparing the DNA sequence of the pathogens with data stored on the decision support knowledge model 4006, including any single nucleotide polymorphism; a suitable approach is employed to change environmental conditions for the plurality animals to reduce or eradicate the pathogens. For example, in an event of fungal or mould growth, the animals that are most susceptible to fungal infections may be temporarily moved to an open field environment whilst animals stalls thereof and indoor accommodation may be fumigated with ozone gas that is effective at killing microbes without leaving any environmentally damaging residues.

As mentioned previously, the welfare system 4000 comprises a software product (using the aforesaid PACE engine) configured to perform a multi-dimensional solution search in the decision support knowledge model 4006, the search being based on at least a subset of the sensor signals and a genotype determination by DNA sequencing of each individual within the assistive environment. Notably, information stored in the decision support knowledge model 4006 acts as an addressable solution space that substantially represents all valid solutions that satisfy all constraints of the welfare system 4000. In other words, the decision support knowledge model 4006 includes valid Cartesian sub-spaces of states or combinations that satisfy a conjunction of all the welfare system 4000 constraints for all interconnected variables such as the subset of the sensor signals and the genotype determination by DNA sequencing of each individual within the assistive environment. Invalid Cartesian sub-spaces are excluded from computations performed in respect of the decision support knowledge model 4006 provide for a high degree of computational efficiency.

Optionally, the system 4000 collects in operation one or more pathogens and/or other microorganisms (for example, neutral, commensal and/or other beneficial microorganisms) present in the assistive environment, genotype sequences the pathogens and/or other microorganisms to characterize the pathogen and/or microorganisms, and employs the characterization thereof as an input parameter to the software product when executed in the data processing arrangement 4002 to use in performing its search.

Referring next to FIG. 38, there is shown a process diagram illustrating steps that are implemented by the welfare system 4000 for enabling the software product (using the aforesaid PACE engine) to perform the multi-dimensional solution search in the decision support knowledge model 4006, in accordance with an embodiment of the present disclosure. At a step 4102, the welfare system 4000 (as shown in FIG. 37) collects in operation one or more pathogens and/or other microorganisms (for example, neutral, commensal and/or other beneficial microorganisms) present in the assistive environment. Additionally, the welfare system 4000 uses one or more mediums for collecting the one or more pathogens and/or other microorganisms from the assistive environment. Specifically, the welfare system 4000 automatically collects the one or more pathogens and/or other microorganisms present in the assistive environment without any human intervention. In an example, the medium for collecting the one or more pathogens are a combination of hardware and software, for example a robotic probe that routinely moves in an autonomous manner around the assistive environment to collect samples. In another example, the medium for collecting the one or more pathogens from the assistive environment may require human intervention. At a step 4104, the welfare system 4000 genotype sequences the one or more pathogens to characterize the pathogen. The genotypes are DNA sequenced and analysis of pathogen type is determined by comparing the DNA sequence of the one or more pathogens, with information stored in the decision support knowledge model 4006. Subsequently, at a step 4106, the welfare system 4000 uses the characterization of the pathogen as an input parameter to the software product when executed in the data processing arrangement 4002 to use in performing its search. The input parameters include features of one or more SNPs obtained from performing DNA base readout from biological samples. In an example, the DNA base readout from biological samples is performed as part of a GWAS (Genome-Wide Association Study). Furthermore, large SNP-genotyping arrays for tens of thousands of individuals (cases and controls) and tens of thousands of SNPs, such as 100,000 individuals and 50,000 SNPs, are available in multiplex formats for huge throughput. In such an example, the features of the one or more SNPs obtained as part of the GWAS are stored in the decision support knowledge model 4006. Furthermore, the biological samples are collected from a plurality of cases, such as the plurality of individuals suffering from a specific disease or disorder and a plurality of controls (such as healthy individuals not suffering from the specific disease or disorder). It will be appreciated that the GWAS datasets can be generated using well-known techniques, including but not limited to, SNP genotyping using SNP microarrays, exome sequencing, genome sequencing and so forth. Furthermore, input parameters obtained from performing the DNA base readout of the biological samples comprise information about SNP genotypes associated with the plurality of cases and the plurality of controls. Alternatively, the data processing arrangement 4002 performs a trait phenotype investigation study. Consequently, individuals are segregated based on high trait performance and low trait performance respectively, to generate the trait phenotype investigation study. Subsequently, individuals with ±2 standard deviations are selected for a specific trait (for example, in case of animals, yield) and compared either directly or as separate sets against a common control. This enables identification of pathways involved in the trait and correspondingly, derivation of predictive markers. For example, in a potato study, top 21 markers were determined to be more predictive of yield than 10,000+ markers that are conventionally used by existing predictive scoring tools (such as, GBLUP).

The data is generated from the input parameters. Such data generated from the plurality of input parameters is stored in the decision support knowledge model 4006 (using the aforesaid PACE engine) as data files. In an example, the data files comprise the input parameter in the structured format (as explained in detail hereinabove).

The data processing arrangement 4002 (using the aforesaid PACE engine) processes the genotype sequences and data from the decision support knowledge model 4006 to generate input parameter to the software product for performing the solution search thereof.

Moreover, the software product (using the aforesaid PACE engine) is used to compute a welfare trajectory for each individual. Specifically, the software product executed by the data processing arrangement 4002 computes (using the aforesaid PACE engine) the welfare trajectory after performing the multi-dimensional solution search in the decision support knowledge model 4006, as will be described herein later.

Notably, a welfare trajectory of a given individual includes at least one constraint and/or at least one environmental condition pertaining to the assistive environment, wherein the at least one constraint and/or the at least one environmental condition is favourable for the given individual. The welfare trajectory is created based upon the information stored in the decision support knowledge model 4006 and results of the multi-dimensional solution search in the decision support knowledge model 4006. Optionally, the welfare trajectory is also based upon the input parameter (namely, the characterization of the one or more pathogens and/or microorganisms collected from an assistive environment). Optionally, the welfare trajectory is based upon a course of treatment identified to be prescribed to a patient individual and administering of the prescribed treatment to the patient individual.

It will be appreciated that the information stored in the decision support knowledge model 4006, the results of the multi-dimensional solution search in the decision support knowledge model 4006, and optionally, the input parameter, constitute a "dataset" (namely, "a corpus of data") on which the software product implements processing operations, to compute the welfare trajectory to be used in providing welfare support for each individual.

Optionally, to compute welfare trajectories for the livestock animals, the software product is operated to:
  (a) perform pre-filtering of the dataset, to reduce a number of inputs that are considered for computing the welfare trajectories;
  (b) perform mining (using the aforesaid MARKERS engine) within the pre-filtered dataset to find distinct n-combinations of SNP genotypes and/or other types of features found in the livestock animals;
  (c) perform (b) repeatedly (using the aforesaid MARKERS engine) for mining a plurality of random permutations of properties using a same set of mining parameters;
  (d) find networks (using the aforesaid MARKERS engine) of distinct n-combinations sharing one or more properties;
  (e) find networks (using the aforesaid MARKERS engine) using the same set of parameters from among the distinct n-combinations and from among the plurality of random permutations, compare null hypothesis and determine one or more p-values with FDR correction to eliminate random observations;
  (f) perform annotation (using the aforesaid ANNOTATION engine) of the networks with a semantically normalised knowledge graph containing information about the shared one or more properties; and
  (g) perform re-clustering of the networks (using the aforesaid ANNOTATION engine), after correlating the networks found at (e) with the semantically normalized knowledge graph of (f) containing information about the shared one or more properties.

Thus, the MARKERS engine is susceptible to being used to identify an association between specific genome variations, for example in a form of one or more SNPs, that give rise to certain diseases and illnesses in individuals or animals.

The data processing arrangement 4002 is configured to perform the pre-filtering from the datasets, comprising tens of thousands of individuals and/or pathogens (and/or microorganisms) and tens of thousands of SNPs or even more (for example 59 million), to reduce a number of the SNPs that are considered for generating the outputs. According to one example implementation, the pre-filtering of the specific datasets includes at least one of removing SNPs where a minor allele frequency associated therewith is below a threshold at which it can satisfy a minimum prevalence criterion for a population; optionally removing SNPs which are approximately co-located and within linkage disequilibrium regions using linkage disequilibrium based clumping; removing SNPs where a major:minor allele distribution is close to 50:50; and including or selecting SNPs that are relevant to a hypothesis or other analytical strategy. In one example embodiment, the pre-filtering of the specific datasets includes removing SNPs which are approximately co-located and within linkage disequilibrium regions, using linkage disequilibrium-based clumping.

In another example implementation, the pre-filtering of the specific datasets includes removing SNPs where a major:minor allele distribution is close to 50:50, such as, where the major:minor allele distribution is 52:48.

The data processing arrangement 4002 is further configured (using the aforesaid MARKERS engine) to perform mining to find all, or a substantial majority of, distinct n-combinations of SNP genotypes and/or other types of features found in the input parameter of the plurality of individuals provided in the decision support knowledge model 4006. In an example implementation, the mining includes finding combinations of SNP genotypes which occur in a plurality of cases (≥MinCases) and with a minimum odds ratio (≥MinOR), analysing in ascending levels of order, in an n number of layers, one layer at a time and storing the n-combinations as N-states in an output data structure. Optionally, during mining of the input parameter (for example, input parameters) and data by the data processing arrangement 4002, a new data-type such as epigenetics data (a series of new elements) can be incorporated as features into the input parameter in addition to the SNP genotypes.

Optionally, the data processing arrangement 4002 (using the aforesaid MARKERS engine) is configured to find high-order combinations of SNP genotypes which synergistically affect a disease status of an individual represented in the input parameters. More optionally, the data processing arrangement 4002 (using the aforesaid PACE engine) is configured to identify a course of treatment to be prescribed to the individual patient, and recommends the administration of the prescribed treatment to the individual patient.

Furthermore, the data processing arrangement 4002 is configured (using the aforesaid MARKERS engine) to perform the mining in ascending levels of order, in an n number of layers, one layer at a time and storing the n-combinations in an output data structure. The n-combinations are stored by odds ratios in descending order. For example, the data processing arrangement 4002 analyses SNPs at a layer 1, wherein SNPs associated with all cases and controls within the population are analysed. At an instance, the data processing arrangement 4002 terminates the determination of combinations (namely, "order") of n-SNPs (or n-combinations) in successive layers. In one embodiment, the data processing arrangement 4002 is configured to determine n-combinations in 20 or more layers.

Optionally, upon successful determination of n-combinations of SNPs in one layer that satisfy the ≥MinCases and the ≥MinOR criteria, the MinCases and MinOR parameters are incremented by the data processing arrangement 4002 to analysis a successive layer. The new parameter settings are defined by the cut-off values of the last n-combination meeting with MaxNStates threshold. Such incrementing of the MinCases and MinOR criteria upon successful determination of n-combinations of SNPs in previous layers, enables the data processing arrangement 4002 to determine largest possible subgroups of cases that are associated with the n-combination of SNPs within the population. In an example, the data processing arrangement 4002 comprises at least one multicore GPU. The filtering of SNP genotypes using the MinCases and MinOR thresholds is computed in parallel on all SNPs on more of GPU's, each GPU core representing one or more SNPs. The data processing arrangement 4002 is operable to employ the GPU and/or the FPGA for the determination of the n-combination of SNPs in the n number of layers. More optionally, the Graphics Processing Unit (GPU) and/or the Field Programmable Gate Array (FPGA) comprise a memory associated therewith. In one example, the memory is implemented as a random-access memory (RAM).

Furthermore, as mentioned hereinbefore, the data processing arrangement 4002 is configured to store the n-combinations of SNPs determined in each layer, as well as individual identifiers for the cases. For example, the data processing arrangement 4002 is configured to assigns a binary vector (indicated by BV hereinafter) to each case, subsequent to determining the n-combinations of SNPs within a layer. The binary vector can take a value of '0' that indicates a specific case not being associated with the n-combination of SNPs for the layer, and a value of '1' that indicates the specific case being associated with the n-combination of SNPs for the layer. The BV is updated by the data processing arrangement 4002 for each layer and is employed for determining n-combinations of SNPs for subsequent layers (whereas the individual identifiers for each of the plurality of individuals in the assistive environment are input to the GPU of the data processing arrangement 4002 prior to initiation of operation thereof). Moreover, the data processing arrangement 4002 is configured to store the n-combinations of SNPs determined in each layer and the BV values associated with the cases, such as, within the memory (such as a random access memory or RAM) associated with the GPU. For example, the data processing arrangement 4002 is configured to store the n-combinations of SNPs and the BV values associated with the cases in the output, such as an output represented by N-states. Furthermore, the data processing arrangement 4002 is configured to perform execution of permutations or repeating when mining a plurality of random permutations of the genotype sequences and pathogens (and/or microorganisms) using a same set of mining parameters. The data processing arrangement 4002 is configured to repeat the mining (as explained in detail hereinabove) a predefined number of times of the plurality of individuals in the assistive environment, with the plurality of random permutations thereof. It will be appreciated that the execution of the permutations by the data processing arrangement 4002 provides statistical significance to the n-states determined by the data processing arrangement 4002 and enables to increase a confidence associated therewith.

The data processing arrangement 4002 is configured (using the aforesaid MARKERS engine) to perform execution of a network analysis or finding networks of distinct n-combinations sharing one or more properties. For example, the networks of distinct n-combinations can be different N-states that have at least one common SNP. In a first example, N-states determined by the data processing arrangement 4002 in a third layer comprise 6-states A to F, such as, A $[3^1\ 5^2\ 247^0]$, B $[3^1\ 218^1\ 775^1]$, C $[3^1\ 5^2\ 842^1]$, D $[3^1\ 247^0\ 264^1]$, E $[218^1\ 264^1\ 511^2]$ and F $[511^2\ 775^1\ 842^1]$.

In such an example, the data processing arrangement 4002 is configured to find networks from the N-states corresponding to each SNP common to one or more N-states, such as, $3^1$ [A, B, C, D], $5^2$ [A, C], $247^0$ [A, D], $264^1$ [D, E], $218^1$ [B, E], $842^1$ [C, F], $775^1$ [B, F] and $511^2$ [E, F].

Optionally, the data processing arrangement 4002 is configured (using the aforesaid MARKERS engine) to merge identical networks, such as, networks having all identical properties. Optionally, the data processing arrangement 4002 is configured to determine a p-value for each network, against a network having higher NC and density than the network. The "p-value" indicates a probability that a SNP is associated with a particular phenotype, wherein the phenotype is any one of: a physical trait, a disease and so forth. Furthermore, p-value represents the significance of a genetic difference between two populations (case and control) at a particular locus on a gene. Furthermore, the data processing arrangement 4002 is configured to perform execution of network validation or finding networks from the n-combinations and from all random permutations using the same set of parameters, comparing null hypothesis and determining one or more p-values with false discovery rate (FDR) correction to eliminate random observations. In one example, the data processing arrangement 4002 is configured to compare a number of pseudo-cases within the network associated with permutations, against a number of cases within the network before performing the permutations. In such an example, if the number of pseudo-cases within the network is more than the number of cases within the network before performing the permutations for more than 50 networks out of 1,000 networks (or the p-value is more than 0.05), the null hypothesis is validated.

Optionally, the data processing arrangement 4002 (using the aforesaid MARKERS engine) is configured to perform false discovery rate (FDR) correction during multiple testing of the networks to compare the null hypothesis. In one example, the data processing arrangement 4002 is configured to employ a technique such as a Benjamini-Hochberg procedure or a Benjamini-Hochberg-Yekutieli procedure to correct for the multiple testing on the networks. For example, the data processing arrangement 4002 is configured to use a FDR of 1% for comparing a null hypothesis. It will be appreciated that comparing the null hypothesis for the networks enables the data processing arrangement 4002 substantially to eliminate random n-combinations that may have been determined by the data processing arrangement 4002.

Optionally, the data processing arrangement 4002 (using the aforesaid MARKERS engine) is configured to determine a penetrance of the networks, such that the penetrance is associated with an amount of population that corresponds to the network. In an example, the penetrance is expressed as a percentage value.

Furthermore, the data processing arrangement 4002 (using the aforesaid ANNOTATION engine) is configured to perform execution of network annotation or annotating networks with a semantically normalized knowledge graph containing information about the shared one or more properties. The ANNOTATION engine enables use of biological knowledge and understanding of mechanisms and functions (the one or more properties) into an analysis. The ANNOTATION engine also enables interpretation of results, such as, by allowing generation of the semantically normalized knowledge graph. The semantically normalized knowledge graph is used, for example, for identification of genes and potential drug discovery and/or repurposing opportunities.

The semantically normalized knowledge graph contains information about the shared one or more properties including but not limited to, SNPs, genes, pathways, targets, drugs, diseases, pharmacogenetics, drug interaction and so forth. In one embodiment, the data processing arrangement 4002 is configured to select one or more properties from the SNPs, genes, pathways, targets, drugs, diseases, pharmacogenetics and drug interaction in the semantically normalized knowledge graph. Subsequently, the one or more properties selected by the data processing arrangement 4002 are correlated with the network of SNPs determined by the data processing arrangement 4002, to determine information about the SNPs, such as, if the SNPs are in a coding, non-coding or eQTL (expression quantitative trait loci) region; the genes or pathways that are affected by the SNPs; diseases or phenotypes associated with the SNPs; a location within the genome where the SNPs are occurring; known phenotypic associations of the SNPs within the networks; if the diseases or phenotypes associated with the SNPs are druggable, and so forth.

Furthermore, the data processing arrangement 4002 (using the aforesaid ANNOTATION engine) is configured to perform re-clustering of the networks, after correlating the validated networks with the semantically normalized knowledge graph containing information about the shared one or more properties. The data processing arrangement 4002 (using the aforesaid ANNOTATION engine) is configured to perform the re-clustering of the networks by merging networks comprising at least one common SNP therein. In the first example, the networks comprising the SNPs $3^1$, $5^2$ and $247^0$ share the N-states A, C, D therebetween. Thus, the networks corresponding to the $3^1$, $5^2$ and $247^0$ can be merged into a cluster, such that the merged network has a connection between the N-states. In such an example, the data processing arrangement 4002 is configured to merge the cases corresponding to the N-states into the cluster. Furthermore, hypothesis driven criteria based on biological insights, role of specific metabolic pathways, phenotypic factors, veterinary factors, and the like, may be applied and tested in the re-clustering stage by re-segmenting the case and control populations based on specific conditions.

According to an embodiment, the re-clustering is used to correlate validated networks with extended phenotypic and veterinary data to find biological explanations for observed associations. The data processing arrangement 4002 is configured to correlate phenotypic and veterinary data (such as, in case of animals hosted within the farming and veterinary environment) to find the biological explanations for the observed associations of the SNPs within the cluster. In one example, the phenotypic and veterinary data is stored in the decision support knowledge model 4006, for example, as semantically normalized knowledge graphs. In another example, the phenotypic and veterinary data can be associated with merged networks corresponding to various other populations. In yet another example, the data processing arrangement 4002 is configured to correlate hypothesis-driven criteria comprising biological insights, role of metabolic pathways, lifestyle data and so forth, find the biological explanations for the observed associations of the SNPs within the cluster.

In one embodiment, the data retrieved from the decision support knowledge model 4006 by the data processing arrangement 4002 comprises epigenetic data. However, the epigenetic data may correspond to continuous variables. In such an example, the data processing arrangement 4002 converts the epigenetic data from the continuous variables into finite domains.

According to an embodiment, the data processing arrangement 4002 is configured to find at least one other feature that is selected from omics, or non-genetic factors. As mentioned hereinabove, the data processing arrangement 4002 correlates phenotypic and veterinary data to find the biological explanations for the observed associations of the SNPs within the cluster. Furthermore, such phenotypic and veterinary data associated with the cases can be used to determine the at least one other feature from epidemiological, environmental, or other non-genetic factors. In one example, the data processing arrangement 4002 is configured to find cases and controls that share at least one non-genetic factor, such as a phenotypic, veterinary, environmental and/or husbandry factor.

Furthermore, the data processing arrangement 4002 (using the aforesaid MARKERS engine) performs high-order (for example, of an order 3 or higher, more optionally of an order 8 or higher, yet more optionally of a 20 or higher, and yet more optionally of an order 50 or higher) combinatorial association of the non-genetic factors and genetic factors, such as, presence and absence of SNPs in the cases and controls respectively, to identify disease protective effects associated with the controls. Moreover, in order to produce the output signals the software considers not only genotype of each of the plurality of individuals, observations and tests carried out on each of the plurality of individuals, detailed information of various medication and drugs that are given to each of the plurality of individuals, on-going observations as the medications are applied to each of the plurality of individuals as well as various data obtained by the plurality of sensors in the sensor arrangement 4004 (such as, food intake, sun time, and so forth).

Optionally, the output signals are used to control at least one of: type and/or quantity of food provided to the individuals; a time when food is provided to the individuals; additional food supplements, probiotics and/or one or more drugs to be administered to the individuals; selective heating or cooling to be supplied to the individuals; pathogen reducing processes to be applied to the assistive environment. The output signals indicate actions required to be taken in order provide the plurality of individuals with optimal welfare. The required actions may relate to different constraints related to feeding provided to the individuals. In an example, the output signals may indicate that a specific individual is deficient in a specific nutrient. Consequently, the output signal may indicate to introduce ingredients/supplements rich in the specific nutrient in food provided to the individuals. In another example, the output signals may indicate a frequent and increased quantity of food to be provided to the individuals. Furthermore, the output signals may be generated based on analysing an increase in number of pathogens associated with a specific disease in the assistive environment. Consequently, effective measures may be taken to eradicate the pathogens from the assistive environment. Furthermore, the sensor signals may indicate abnormal health conditions of a specific individual in the assistive environment. Consequently, the output signals generated by the software product may direct additional food supplements and/or one or more drugs to be administered to the individuals.

Additionally, the output signals may indicate need of providing selective heating or cooling to the individuals. Beneficially, this may provide the individuals a more personalized and dedicated welfare. Optionally, the data processing arrangement 4002 is configured to find single disease case sub-populations that share high-order disease-associated combinatorial features. Notably, many diseases are caused by a combination of genetic as well as non-genetic (such as phenotypic and environmental) factors. Furthermore, a same disease can be caused due to presence of a plurality of different genetic factors, such as SNPs, in different cases within a population. Moreover, the plurality of different case sub-populations may not share any common SNPs or may share a minimal number of SNPs therebetween. In such an example, identification of disease riskfactors, determination of treatment for each individual within the population and so forth, requires identification of the case sub-populations that share SNPs therebetween. The data processing arrangement 4002 finds such single disease case sub-populations that share high-order disease-associated combinatorial features (such as SNPs).

Optionally, the data processing arrangement 4002 (using the aforesaid PACE engine) is configured to design a course of treatment that is customized for the given individual, wherein the treatment is based upon the individual's SNP genotype and at least one non-genomic feature of the individual. As aforementioned, complex diseases are caused by a combination of genetic (such as SNPs) as well as non-genetic (such as phenotypic) factors. Furthermore, conventional treatments for treating such complex diseases (such as, for drug discovery) include prescribing drugs for a specific disease, without taking into account the combination of the genetic and non-genetic (such as phenotypic) factors that may vary among the individuals. Therefore, there is a requirement to design treatments for such complex diseases by considering combinations of genetic (SNPs) and non-genetic (such as phenotypic) factors for specific individuals. The data processing arrangement 4002 is configured to design a course of treatment that is customized for the given individual, wherein the treatment is based upon the individual's SNP genotype and at least one non-genomic feature (such as phenotypic) of the case. In one example, micro-biopsies of the given individual are conducted to obtain a cellular assay platform. Subsequently, organoids associated with one or more organs affected by disease are developed for the given individual. Thereafter, SNP genotypes associated with the organoids for the given individual is determined. Alternatively, SNP sequencing techniques are employed to determine SNPs genotypes associated with the disease for the given individual.

More optionally, the data processing arrangement 4002 (using the aforesaid PACE engine) selects, when in operation, at least one of the one or more features from clinical observations, tests carried out on the given individual and information of medications and drugs. For example, the data processing arrangement 4002 receives information associated with the disease of the given individual from clinical observations, tests carried out on the given individual and/or medications and drugs used by the given individual for treatment of the disease. In another embodiment, the data processing arrangement 4002 employs in operation ongoing observations, as the medications that are used for treating the given individual, that are added as features (input drivers) to the input parameters used by the data processing arrangement 4002. For example, the data processing arrangement 4002 receives information of medications used for treating the given individual and determines an efficacy associated therewith. In such an example, the data processing arrangement 4002 can perform the drug discovery iteratively, to suggest improved drugs for treating the given individual with each iteration.

Referring next to FIG. 39, there is shown an illustration of steps of a method 4400 of operating a welfare system, for example the welfare system 4000 of FIG. 37; the welfare system is configured to provide welfare support to a plurality of individuals in an assistive environment, in accordance with an embodiment of the present disclosure. The method 4400 makes use of a system that includes a data processing arrangement that is configured to receive sensor signals from a plurality of sensors that are spatially distributed within the assistive environment, wherein the data processing arrangement includes a decision support knowledge model against which the sensor signals are compared, wherein the data processing arrangement provides output signals that control operation of the assistive environment, and wherein the data processing arrangement executes a software product that in execution analyses the sensor signals in respect of the decision support knowledge model and generates the output signals. At a step 4402, the software product when executed performs a multi-dimensional solution search in the decision support knowledge model, the search being based on at least a subset of the sensor signals and a genotype determination by DNA sequencing of each individual within the assistive environment. At a step 4404, the sensor arrangement is used to sense in operation environmental conditions for each individual, including monitoring a food intake for each individual. At a step 4406, the decision support knowledge model is populated with at least one of drug characteristics, food supplement characteristics, husbandry strategies (such as, when the individual is an animal hosted within a farming and veterinary environment) depending on individual health complications, disease characteristics of each individual, individual genotype data, and SNP polymorphism data. At a step 4408, the software product is used to compute a welfare trajectory for an individualized customized husbandry of each individual.

Optionally, the method includes arranging for the SNP data to include single nucleotide polymorphisms characterizing each individual, determined by using microarrays, DNA sequencing, CRISPR or Polymerase Chain Reaction (PCR) to read genetic tissue samples derived for each individual. Beneficially, the method is used to select preferred embryos having desired phenotype characteristics, wherein selected embryos are implemented using IVF techniques to enable individuals to be realised having the desired phenotype characteristics.

Optionally, the method includes arranging for the sensor arrangement to include a plurality of sensors that are spatially distributed within the assistive environment and are coupled in communication with the data processing arrangement by using a wireless dynamically reconfigurable communication network.

Optionally, the method includes arranging for the wireless dynamically reconfigurable communication network to be implemented as a peer-to-peer (P2P) network.

Optionally, the method includes arranging for the system to collect in operation one or more pathogens and/or microorganisms (for example, neutral, commensal and/or other beneficial microorganisms) present in the assistive environment or within the individual, perform genotype sequencing of the one or more pathogens and/or microorganisms to characterise the one or more pathogens and/or microorganisms, and use the characterisation of the one or more pathogens and/or microorganisms as an input parameter to the software product when executed in the data processing arrangement to use in performing its search.

Optionally, the method includes employing the output signals to control one or more of:
  (i) a type and/or a quantity of food provided to the individuals;
  (ii) a time when food is provided to the individuals;
  (iii) additional food supplements, probiotics and/or one or more drugs to be administered to the individuals;
  (iv) changes to husbandry practices (such as, when the individual is an animal hosted within a farming and veterinary environment) including selective heating or cooling to be supplied to the individuals; and
  (v) pathogen reducing processes to be applied to the assistive environment.

Optionally, the method includes arranging for the data processing arrangement to find high-order combinations of SNP genotypes which synergistically affect a disease status of an individual represented in the input parameters.

Optionally, the method includes arranging for the data processing arrangement to find single disease case subpopulations that share high-order disease-associated combinatorial features.

Optionally, the method includes arranging for the data processing arrangement to design (namely, to devise) a course of treatment that is customized for a given individual, wherein the treatment is based upon the individual's SNP genotype and at least one non-genomic feature of the individual.

Optionally, the method includes arranging for the data processing arrangement to select at least one of the one or more features from clinical observations, tests carried out on the given individual and information of medications and drugs.

Optionally, the method includes arranging for the data processing arrangement to employ ongoing observations, as the medications are used for treating the individual, that are added as features to the input parameters used by the data processing arrangement.

Referring next to FIG. 40, there are illustrated therein steps of a method 4500 of operating the system 4000, for example when treating an individual in need thereof, in accordance with an embodiment of the present disclosure. At a step 4502, high-order combinations of SNP genotypes and/or one or more other features which synergistically affect disease status are identified, using the welfare system and/or the method of (namely, the method for) operating a welfare system; "high-order" is as defined in the foregoing. At a step 4504, a course of treatment to be prescribed to the individual is designed (namely, devised), the treatment being based upon the individual's genotype (SNPs) and/or at least one or more non-genomic feature. At a step 4506, the prescribed treatment of the individual is administered.

Optionally, the method includes:
  (a) identifying (using the aforesaid PACE engine) high-order combinations of the individual's SNP genotypes and/or one or more other features which synergistically affect disease status; and
  (b) administering the prescribed treatment to the individual.

Optionally, the method includes implementing a treatment using a combination of drugs, for example using repurposed drugs.

Optionally, the method includes designing (namely, devising) a course of treatment to be prescribed to an individual, characterized in that the method comprises:
  (a) identifying (using the aforesaid PACE engine) high-order combinations of SNP genotypes and/or one or more other features which synergistically affect disease status, using the method or the welfare system; and
  (b) designing (using the aforesaid PACE engine) a course of treatment based upon the case's genotype (SNPs) and/or at least one more non-genomic feature.

Referring next to FIG. 41, there are illustrated therein steps of a method 4600 of identifying a course of treatment to be prescribed to a given individual, in accordance with an embodiment of the present disclosure. The method 4600 relates to using the welfare system 4000 of FIG. 37 that, when in operation, develops a personalized identification of one or more active drug combinations for the treatment or prevention of a given patient individual's specific disease The welfare system 4000 includes the data processing arrangement 4002 of FIG. 37 that receives a plurality of measurands of the given patient individual and accesses the decision support knowledge model 4006 of FIG. 37 including a plurality of treatment strategies and genomic data. At a step 4602, the data processing arrangement 4002 (using the aforesaid PACE engine) is configure to identify high-order combinations of the individual's SNP genotypes and/or one or more other features which synergistically affect disease status, using a computational engine (namely the PACE engine) with a combinatorial methodology for combinatorial feature analysis executed in the data processing arrangement 4002; "high-order" is to be construed as, for example more than a two-element combinatorial search, for example a three element combinatorial search. Typically, the high-order combinatorial searches are performed for higher orders. For example, in case of a given gene, the high-order combinatorial search ranges from about 5 to about 20, more preferably circa 6 to circa 17 orders. In another example, in case of a given gene, the high-order combinatorial search ranges from about 3 to about 15 and more preferably circa 5 to circa 13 orders.

The steps 4602 to 4608 are only illustrative and other alternatives can also be provided where one or more steps are added, one or more steps are removed, or one or more steps are provided in a different sequence without departing from the scope of the claims herein. In an example, there is a form of control apparatus (using the aforementioned PACE engine) referred to as a "discovery apparatus" for processing one or more data inputs in a computing arrangement to provide one or more control outputs (such as, for controlling the aforesaid assistive environment) and/or one or more analysis output and/or one or more recommendation outputs (such as, for prescribing a course of treatment for a given individual within the assistive environment), characterized in that the control apparatus includes a user interface for interacting with a user of control apparatus for controlling operation of the control apparatus, a data processing arrangement that is operable to receive the one or more data inputs and to output the one or more control outputs and/or one or more analysis output and/or one or more recommendation outputs, wherein the computing arrangement is operable to execute a software product for implementing the method. In an example, the SNPs are selected from SNPs found present in non-coding regions of genes, in the intergenic regions or in coding regions of genes. In another example, the drug or combination of drugs for use in therapy comprises the drug or combination of drugs to be administered to the patient individual identified using the method of the present disclosure. Beneficially, MARKERS can be considered as being a discovery apparatus (population scale), whereas PACE can be considered as being a control apparatus (individual scale).

Referring to FIG. 42, there is shown an illustration of a cycle of continuous welfare to be provided to animals, in accordance with an embodiment of the present disclosure. The welfare to be provided to the animals is guided by multiple dimensions and combinations of data predictive of one or more outcome phenotypes, such as, the data comprising genomic data, veterinary records, microbiomic data, epigenetic data, data acquired from real-time monitoring of the animals, data related to pathogens and/or other microorganisms collected from a farming and veterinary environment that the animals are hosted therein, data related to dietary and water intake of the animals, and data acquired by performing veterinary analysis of the animals. Such combinations of data are analyzed to determine a best course of treatment to be prescribed to the animals for improving welfare of the animals and a performance of the animals is evaluated on an on-going basis (and in an iterative manner). Subsequently, the course of treatment to be prescribed to the animals is optimized, based on the performance of the animals.

It will be appreciated from the above disclosure that the welfare system 4000 is susceptible to being employed for:
(i) providing improved selective breeding of animals, such as, for optimization of complex traits such as yield, food conversion, fertility, fit to environment and so forth;
(ii) providing one or more of: improved selective breeding of animals, improved selection of therapy for individuals (humans or animals);
(iii) determining risk scores; and
(iv) implementing decision support tools for precision medicine, implementing precision agriculture, providing recommendations for optimizing food and diet.

Moreover, the welfare system 4000 can be employed for improved selection of therapy for individuals (for animals as well as human patients) based on genomic, phenotypic, clinical and/or veterinary data. The welfare system 4000 can be employed for providing improved welfare to individuals, such as, better fit of individuals to diet, environment and the like. The welfare system 4000 also enables better risk scoring using combinations of features and integration of such data into decision support models (for example, for prediction of range of phenotypes including disease risk, rate of disease progression, therapy response, opportunities for repurposing drugs). Moreover, the welfare system 4000 can be employed for development of decision support tools including precision medicine, precision agriculture and the like, to make real-time fully contextualized responses and recommendations for optimizing food, management, husbandry and so forth of animals, based on combinations of data associated with genomics, epigenetics, environmental, acquired using sensors, acquired from IoT apparatuses, acquired using satellites, and the like.

Building Decision Support Systems

The construction of the Array System Model and Decision Support Application is a multi-stage process involving the following steps:
Step 1—Mining of Source Data and Semantic Normalization (using the aforesaid MARKERS engine);
Step 2—Compilation and Validation of Array System Model; and
Step 3—Accessing Array System Model on mobile/wearable device via Runtime API using the User's Input State Vector.

The array system model is converted by the Array System Model compiler into a verified and normalized structure, that can be represented in a very compact format (usually a few kilobytes), which is an amount of memory the model consumes when loaded into an Array Runtime API on a given user's mobile device, for example a smart phone or a smart watch. A significant proportion of this memory (namely, over 60% thereof) is simply used for storing names of drugs being considered in the computation, as well as diseases and foods; such data is potentially further optimized, if necessary, so that the Array System Model requires even less computing resources in operation. The Array System Model provides an analytical and predictive substrate to power a personalized decision support app (namely, application software) on the given user's mobile device. This substrate enables the Runtime API running directly on the user's mobile device (smart watch, phone, or tablet) to use the Array System Model to perform logical inferences on the data and deduce all the consequences of a given parameter for a selected data set. Embodiments of the present disclosure are operable to provide a decision support system for performing aforementioned analyses within a predictable and very short time; for example, a proprietary Google Nexus Apple® or Microsoft® tablet computer running an Android software platform is capable of implementing analyses within five to ten milliseconds. Such computational performance is provided with a constant and low memory footprint (namely, around 430 kB in practice), and is guaranteed to find all the potential adverse consequences given by constraints imposed by a given user's input state vector.

Optionally, the computing arrangement includes at least one of: a computing device and a distributed arrangement including a plurality of computing devices.

Optionally, the sub-models are distributed over a plurality of computing devices that are mutually coupled together in operation via a data communication network.

Optionally, the method includes generating and storing, in a data memory or data storage medium of the computing arrangement, an addressable solution space defining all valid transitions between all valid states.

Optionally, the method includes computing the state of the entire system model in real-time by consulting one or more sub-systems and/or relations at a time by deducing possible states of each variable and propagating one or more bound link variables to connected one or more relations until no further constraints can be added to the state vectors.

Optionally, the control apparatus is configured to be employable for controlling one or more of:
(i) industrial production facilities;
(ii) agricultural production facilities;
(iii) healthcare providing facilities;
(iv) drug discovery systems;
(v) smart metering arrangements;
(vi) autonomous and self-drive vehicle driving arrangements;
(vii) in intelligent drones for surveillance use;
(viii) in airborne radar systems; and
(ix) in intelligent apparatus for assisting veterinary surgery and/or treatment.

Markers Engine

The MARKERS engine employs combinatorial methodology to perform combinatorial feature analysis, wherein the computational engine works on GWAS datasets. The combinatorial feature analysis takes into account epistatic interactions between various genetic and non-genetic factors leading to pleiotropic effects on phenotype. The epistatic interaction refers to combinations of multiple features, such as single-nucleotide polymorphisms (SNPs) genotypes and other features associated with a phenotype exerting non-linear additive effects, that in a specific combination are found in individuals associated with a disease (namely, cases) but not in healthy population (namely, controls). Thus, each SNP (with genotypes 0, 1, 2) is to be considered as a state variable with 3 states (bins). In general, the mining can be carried out on features with more than 3 states. The pleiotropic interaction refers to the same combination of features associated with different diseases or phenotypes. The computational engine employs GWAS datasets that may be stored in a database arrangement. Furthermore, the GWAS datasets can be generated using well-known techniques, including but not limited to, SNP genotyping using SNP microarrays, exome sequencing, genome sequencing, and so forth. Furthermore, a pre-filtering of specific datasets to be analyzed is employed. The pre-filtering step is performed to reduce the number of SNPs to be considered, wherein the pre-filtering includes at least one of removing SNPs that are in linkage disequilibrium; removing SNPs and/or other features that are irrelevant to or not likely to be of sufficient statistical significance for the analysis; and selecting specific SNPs and features. It will be appreciated that the SNPs that are within linkage disequilibrium have non-random associations with each other and thus, a likelihood of determining a random association therebetween that may lead to generation of outputs of medical products or methods is low. The pre-filtering includes removing SNPs and/or other features that are irrelevant to or not likely to be of sufficient statistical significance for the analysis. Such pre-filtering of the irrelevant SNPs or SNPs having a less likelihood of having sufficient statistical significance, enables removal of SNPs that will have a negligible effect on the generated output. In yet another example, the pre-filtering is performed, such that the pre-filtering includes selecting specific SNPs and features, such as, SNPs or features corresponding to one or more hypotheses. In such an example, the hypothesis can correspond to variations (or polymorphisms) due to non-coding variants, biological insights, metabolic pathways, lifestyle (such as diet, smoking, drinking, sleep, exercise, and the like), clinical information (such as existing prescriptions, diagnostic results like imaging, assays, and the like), phenotypic information (such as age, sex, race, weight, comorbidities), and so forth.

The MARKERS engine performs mining to find all or a substantial majority of distinct n-combinations of SNP genotypes and/or other types of features found in the input measurands of many cases and a few controls provided in the database arrangement. Such mining is performed in ascending levels of order, in an n number of layers, one layer at a time and the n-combinations are stored in an output data structure. For example, 20 SNPs are analyzed at a layer 1, wherein SNPs associated with all cases and controls within the population are analyzed. Alternatively, a specific set of cases and controls are analyzed at the layer 1, wherein such a specific set can be predefined by a user (for example, based on a hypothesis). Subsequently, combinations of 2 SNPs occurring in the cases and controls in a layer 2 are determined from the set of SNPs determined in the layer 1. All reported n-combinations (or n-states) are sorted by odds ratio in descending order (with a minimum OR depending on the maximum number of reported n-states). Thus, the reported n-states must satisfy 1) >=minCases to ensure a minimum penetrance and 2) OR>=minOR). Thereafter, combinations of 3 SNPs occurring in the cases and controls in a layer 3 are determined from the set of SNPs determined in the layer 1. Similarly, incremental (n+1) combinations of SNPs are determined in successive layers, until no valid combinations of SNPs are found at a particular layer. In such an instance, the determination of combinations of n-SNPs (or n-combinations) is terminated in successive layers. In one example, the n-combinations are determined in 20 or more layers.

Furthermore, a penetrance of the networks is determined, such that the penetrance is associated with an amount of population that corresponds to the network. In an example, the penetrance is expressed as a percentage value. Moreover, the MARKERS engine performs, in operation, execution of network annotation or annotating networks with a semantically normalized knowledge graph containing information about the shared one or more properties. The semantically normalized knowledge graph contains information about the shared one or more properties including but not limited to, SNPs, genes, pathways, targets, drugs, diseases, pharmacogenetics and drug interactions and so forth. In one embodiment, one or more properties from the SNPs, genes, pathways, targets, drugs, diseases, pharmacogenetics and drug interactions are selected in the semantically normalized knowledge graph. Subsequently, the one or more properties selected is correlated with the network of SNPs to determine information about the SNPs, such as, if the SNPs are in a coding, non-coding or eQTL (expression quantitative trait loci) region; the genes or pathways that are affected by the SNPs; diseases or phenotypes associated with the SNPs; a location within the genome where the SNPs are occurring; known phenotypic associations of the SNPs within the networks; if the diseases or phenotypes associated with the SNPs are druggable, and so forth.

Moreover, the MARKERS engine, in operation, performs re-clustering of the networks, after correlating the validated networks with the semantically normalized knowledge graph containing information about the shared one or more properties. The re-clustering of the networks is performed by merging networks comprising at least one common SNP therein. Furthermore, hypothesis driven criteria based on biological insights, role of specific metabolic pathways, lifestyle factors, clinical factors, and the like, may be applied and tested in the re-clustering stage by re-segmenting the case and control populations based on specific conditions.

The re-clustering is used to correlate validated networks with extended phenotypic and clinical data to find biological explanations for observed associations. The correlation of phenotypic and clinical data is performed to find the biological explanations for observed associations of the SNPs within the cluster. In an example, the phenotypic and clinical data can be associated with merged networks corresponding to various other populations. In another example, hypothesis-driven criteria comprising biological insights, role of metabolic pathways, lifestyle data and so forth, are correlated to find the biological explanations for the observed associations of the SNPs within the cluster.

In exemplary operation, a data processing arrangement implementing the MARKERS engine finds at least one other feature that is selected from phenotypic, or non-genetic factors. As mentioned hereinabove, the data processing arrangement correlates phenotypic and clinical data to find the biological explanations for observed associations of the SNPs within a cluster. Furthermore, such phenotypic and clinical data associated with the cases can be used to determine the at least one other feature from phenotypic, or non-genetic factors. In one example, the data processing arrangement in operation finds cases and controls that share at least one non-genetic factor, such as a phenotypic, clinical and/or lifestyle factor. Furthermore, the data processing arrangement performs high-order combinatorial association of the non-genetic factors and genetic factors, such as, presence and absence of SNPs in the cases and controls respectively, to identify disease protective effects associated with the controls. In an example, the controls comprise individuals of a population that had not developed breast cancer by an age of 55 years (1,458) and the cases comprise individuals of the population that had developed breast cancer before an age of 40 years (1,576). In such an example, the data processing arrangement identifies high-order non-disease-associated combinatorial features in 451 individuals of 1,458 controls, using a false discovery rate (FDR) of 5%, within the population used that can be used to identify disease protective effects within the population. These are also prime candidate for novel drug discovery or repurposing, because they offer an opportunity to increase functioning of those pathways.

Referring to FIG. 43, there is shown an illustration of a data flow associated with MARKERS implemented with respect of the Array System Model of FIG. 1 generated by the aforesaid PACE computing engine pursuant to the present disclosure, wherein an input data file includes all samples (cases and controls) with associated feature states, for example SNP genotypes. An output data file includes a list of validated m-states (and associated networks), wherein each validated n-state (combined with the input data file) is used to build one or more relations of the Array System Model (ASM). In other words, the PACE computing engine generates a PACE model (namely ASM) that can be derived directly from MARKERS without there arising a need to employ colligation.

In FIG. 44, there is shown an illustration of contents of the input data file used for MARKERS as well as for deriving ASM relations; features, for example SNP's, are considered as state variables and associated corresponding outcomes (namely, phenotypes) as object functions.

Referring next to FIG. 45, there is shown an illustration of an ASM relation on selected features (defined by a validated n-state) representing all possible n-combinations of the states (for example, genotype combinations). Thus, the validated n-state is just one of all combinations, wherein such processing can be considered as a lossless dimensionality reduction on all other features.

In FIG. 46, there is shown an illustration of an ASM relation derived from a potato dataset with associated yield; the aforesaid MARKERS is run to compare high yield (cases) versus low yield (controls), wherein one of the validated n-states is found in layer 8; the state variables of the ASM relation are thus 8 SNPs from the validated n-state, and the relation now contains all possible 8-combinations (including the validated one) defined in an input dataset and an output yield (object function); the ASM relation is susceptible to being used to optimize the outcome, for example by analyzing an impact of changes in genotypes of one or more SNPs in combination.

Referring to FIG. 47, there is shown an illustration of an example of an ASM relation derived from a disease study, wherein the study included 607 patients with bipolar disorder and 1355 healthy control. Deriving the ASM relation includes using a case-control split to calculate object functions (namely, a sum of cases, a sum of controls and a derived odds ratio). Using MARKERS, it feasible to identified a 3-combination with high penetrance (sumCases) and high odds ratio (OR), wherein the ASM relation represents all 3×3×3 genotype combinations of 3 SNPs. Similarly, it is feasible to add combinatorial risk scores (CRS) as another object function. Each validated n-state will define a unique ASM relation with all combinations defined. An example system for clinical decision support, it is feasible to have a large number of validated n-states, wherein each of which defines a compact ASM relation. An input state vector is a genomic signature of an individual given patient, and an output state vector include calculated combinatorial risk scores, based on an accumulated contribution from all relations.

In FIG. 48, there is shown an illustration of steps of a method for building ASM relations directly from MARKERS. It will be appreciated here that the aforesaid PACE computing engine and its associated compiler is not needed in the method of FIG. 48, since there is no colligation of relations required in the method of FIG. 48.

Modifications to embodiments of the present disclosure described in the foregoing are possible without departing from the scope of the present disclosure as defined by the accompanying claims. Expressions such as "including", "comprising", "incorporating", "consisting of", "have", "is" used to describe and claim embodiments of the present disclosure are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

We claim:

1. A welfare system that is configured to provide welfare support to a plurality of individuals in an assistive environment, wherein the welfare system includes a control apparatus that is configured to receive a plurality of measurands of a given individual within the assistive environment, wherein the control apparatus is configured to process one or more data inputs in a computing arrangement to provide one or more outputs comprising at least one of control outputs, analysis outputs, or recommendation outputs, wherein the control apparatus is configured to execute real-time computing for a multidimensional system model spanned by state variables on one or more of finite domains or intervals, wherein the one or more data inputs include one or more physical measurands of a system, and the one or more outputs provide a technical modification of the system, wherein:
the control apparatus comprises a system model in which all valid combinations and associated properties or object functions are stored as interconnected relations distributed on one or more computers; and
the control apparatus is configured to deduce one or more of:
(i) any sub-space, corresponding to an input statement of states or combinations spanned by one or more state variable or associated properties or object functions, by deriving consequences of the input statement by applying constraints defined by the input statement to the system model; or
(ii) any sub-space, corresponding to a query, of states or combinations spanned by one or more state variables or associated properties or object functions, by deriving consequences of the query by applying constraints defined by the query to the system model,
wherein the control apparatus includes a decision support knowledge model including a plurality of treatment strategies and at least one of: drug characteristics, food supplement characteristics, husbandry strategies depending on individual health complications, disease characteristics of each individual, individual genotype data, and SNP data, wherein the control apparatus provides output signals for developing a personalized identification of one or more active drug combinations for the treatment or prevention of a given individual's specific disease, and wherein the control apparatus executes a software product that in execution performs a high-order combinatorial search within the decision support knowledge model based upon the plurality of measurands and generates the output signals, characterized in that:
(a) the welfare system is configured to use the given individual's SNP genotypes and/or one or more other features which synergistically affect disease status as a part of the measurands; and
(b) the software product is configured to perform a multi-dimensional solution search in the decision support knowledge model to identify high-order combinations of the given individual's SNP genotypes, using the computational engine, implemented as a PACE engine, with combinatorial methodology for combinatorial feature analysis executed in the data processing arrangement, for each individual within the assistive environment; and
(c) the software product is used to compute a welfare trajectory for an individualized welfare of each individual, wherein the welfare trajectory comprises a course of treatment to be prescribed to the given individual.

2. The welfare system of claim 1, wherein the system further comprises a sensor arrangement spatially distributed within the assistive environment, wherein the control apparatus receives sensor signals from the sensor arrangement that is configured to sense environmental conditions for each individual, including monitoring a food intake for each individual, and wherein the control apparatus executes the software product that analyses the sensor signals in respect of the decision support knowledge model by performing a multi-dimensional solution search in the decision support knowledge model based on at least a subset of the sensor signals and a genotype determination by DNA sequencing of each individual within the assistive environment.

3. The welfare system of claim 1, wherein the control apparatus is configured to execute the high-order combinatorial search, wherein the genomic data is associated with a given gene of the given individual.

4. The welfare system of claim 1, wherein the SNP data includes single nucleotide polymorphisms characterizing each individual and a case or control specification of each individual.

5. The welfare system of claim 1, wherein the welfare system is configured to collect one or more pathogens present and/or other microorganisms in the assistive environment, to genotype sequence the pathogens and/or other microorganisms to characterize the pathogens and/or other microorganisms, and to use the characterization of the pathogens and/or other microorganisms as an input parameter to the software product when executed in the control apparatus to use in performing its search for computing the welfare trajectory for the individualized welfare of each individual.

6. The welfare system of claim 1, wherein the output signals are used to control at least one of:
(i) type and/or quantity of food provided to the individuals;
(ii) a time when food is provided to the individuals;
(iii) additional food supplements and/or one or more drugs to be administered to the individuals;
(iv) changes to husbandry practices including selective heating or cooling to be supplied to the individuals; and
(v) pathogen reducing processes to be applied to the assistive environment.

7. The welfare system of claim 1, wherein the welfare system is configured to analyze the given individual's entire genome from the given individual's sample provided as measurands to the control apparatus, to capture a disease network pertaining to the given individual's entire genome.

8. The welfare system of claim 1, wherein the control apparatus is configured to find high-order combinations of states which synergistically affect a disease status of the given individual represented in the input parameters.

9. The welfare system of claim 8, wherein the control apparatus is configured to process state variables including SNP genotypes.

10. The welfare system of claim 8, wherein the welfare system is configured to identify a treatment for the disease that is selected from a group including: metabolic, cancer, cardiovascular, respiratory, neurodegenerative, neuropsychiatric, autoimmune, immunological, inflammatory and respiratory diseases.

11. The welfare system of claim 10, wherein the control apparatus data is configured to devise a course of treatment for the given individual, wherein the treatment is based upon the patient individual's SNP genotype and at least one nongenomic feature of the given individual.

12. A method for using a welfare system to provide welfare support to a plurality of individuals in an assistive environment, wherein the welfare system includes the control apparatus of claim 1 that is configured to receive a plurality of measurands of a given individual within the assistive environment, wherein the control apparatus includes a decision support knowledge model including a plurality of treatment strategies and at least one of: drug characteristics, food supplement characteristics, husbandry strategies depending on individual health complications, disease characteristics of each individual, individual genotype data, and SNP data, wherein the control apparatus is configured to provide output signals for developing a personalized identification of one or more active drug combinations for the treatment or prevention of a given individual's specific disease, and wherein the control apparatus is configured to execute a software product to perform a high-order combinatorial search within the decision support knowledge model based upon the plurality of measurands and to generate the output signals, characterized in that the method includes:
- (a) employing the given individual's SNP genotypes and/or one or more other features which synergistically affect disease status as a part of the measurands;
- (b) arranging for the software product to perform a multi-dimensional solution search in the decision support knowledge model to identify high-order combinations of the given individual's SNP genotypes, using a computational engine, with combinatorial methodology for combinatorial feature analysis executed in the control apparatus, for each individual within the assistive environment; and
- (c) using the software product to compute a welfare trajectory for an individualized welfare of each individual, wherein the welfare trajectory comprises a course of treatment to be prescribed to the given individual.

13. The method of claim 12, wherein the welfare system further comprises a sensor arrangement spatially distributed within the assistive environment, wherein the method comprises arranging for the control apparatus to:
- (a) receive sensor signals from the sensor arrangement that is configured to sense environmental conditions for each individual, including monitoring a food intake for each individual, and
- (b) execute the software product that analyses the sensor signals in respect of the decision support knowledge model by performing a multi-dimensional solution search in the decision support knowledge model based on at least a subset of the sensor signals and a genotype determination by DNA sequencing of each individual hosted within the assistive environment.

14. A computer program product comprising a non-transitory computer readable storage medium having computer-readable instructions stored thereon, the computer-readable instructions being executable by a computerized device comprising processing hardware to execute the method of claim 12.

* * * * *